(12) United States Patent
Ebden et al.

(10) Patent No.: US 8,106,063 B2
(45) Date of Patent: *Jan. 31, 2012

(54) PYRIMIDYL SULPHONE AMIDE DERIVATIVES AS CHEMOKINE RECEPTOR MODULATORS

(75) Inventors: Mark Ebden, Loughborough (GB); Premji Meghani, Loughborough (GB); Colin Bennion, Loughborough (GB); Anthony Ronald Cook, Loughborough (GB); Roger Victor Bonnert, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/508,934

(22) Filed: Jul. 24, 2009

(65) Prior Publication Data

US 2010/0063079 A1    Mar. 11, 2010

Related U.S. Application Data

(63) Continuation of application No. 10/522,871, filed as application No. PCT/GB2003/003175 on Jul. 23, 2003, now Pat. No. 7,582,644.

(30) Foreign Application Priority Data

Jul. 27, 2002  (GB) .................................... 0217431.6

(51) Int. Cl.
| | |
|---|---|
| A61K 31/505 | (2006.01) |
| A61K 31/506 | (2006.01) |
| A61P 11/06 | (2006.01) |
| A61P 17/06 | (2006.01) |
| A61P 19/02 | (2006.01) |
| A61P 35/00 | (2006.01) |
| C07D 239/46 | (2006.01) |
| C07D 403/12 | (2006.01) |
| C07D 403/14 | (2006.01) |
| C07D 413/12 | (2006.01) |
| C07D 413/14 | (2006.01) |
| C07D 407/12 | (2006.01) |
| C07D 407/14 | (2006.01) |
| C07D 409/12 | (2006.01) |
| C07D 409/14 | (2006.01) |
| C07D 405/12 | (2006.01) |
| C07D 405/14 | (2006.01) |

(52) U.S. Cl. .................. 514/269; 514/275; 544/317
(58) Field of Classification Search .............. 544/317; 514/275, 269

See application file for complete search history.

(56) References Cited

U.S. PATENT DOCUMENTS

| | | | |
|---|---|---|---|
| 2,540,356 | A | 2/1951 | Sprague |
| 3,082,206 | A | 3/1963 | Langley |
| 3,132,139 | A | 5/1964 | Bretschneider et al. |
| 3,328,395 | A | 6/1967 | Nitta et al. |
| 3,452,018 | A | 6/1969 | Santilli et al. |
| 3,457,278 | A | 7/1969 | Zimmermann |
| 3,673,184 | A | 6/1972 | Minami et al. |
| 7,482,355 | B2 | 1/2009 | Ebden et al. |
| 7,582,644 | B2 * | 9/2009 | Ebden et al. .................. 514/269 |
| 7,838,675 | B2 | 11/2010 | Cheshire et al. |
| 2008/0096860 | A1 | 4/2008 | Cheshire et al. |
| 2010/0063079 | A1 | 3/2010 | Ebden et al. |
| 2011/0124619 | A1 | 5/2011 | Cheshire et al. |

FOREIGN PATENT DOCUMENTS

| | | |
|---|---|---|
| GB | 1042295 | 9/1966 |
| JP | 61-118372 | 5/1986 |
| JP | 03-197467 | 8/1991 |
| WO | WO 91/15209 | 10/1991 |
| WO | WO 97/22596 | 6/1997 |
| WO | WO 97/30035 | 8/1997 |
| WO | WO 97/32856 | 9/1997 |
| WO | WO 98/13354 | 4/1998 |
| WO | WO 99/02166 | 1/1999 |
| WO | WO 99/41253 | 8/1999 |
| WO | WO 00/09511 | 2/2000 |
| WO | WO 00/40529 | 7/2000 |
| WO | WO 00/41669 | 7/2000 |
| WO | WO 00/76980 | 12/2000 |
| WO | WO 01/25242 | 4/2001 |
| WO | WO 01/58902 | 8/2001 |
| WO | WO 01/58906 | 8/2001 |
| WO | WO 01/92224 | 12/2001 |
| WO | WO 02/04434 | 1/2002 |
| WO | WO 02/08213 | 1/2002 |
| WO | WO 02/24665 | 3/2002 |

(Continued)

OTHER PUBLICATIONS

Banker et al., "Prodrugs", Modern Pharmaceutics, 3rd ed., Marcel Dekker, New York, pp. 451 & 596 (1996).

(Continued)

*Primary Examiner* — Venkataraman Balasubramanian
(74) *Attorney, Agent, or Firm* — Fish & Richardson P.C.

(57) ABSTRACT

A compound of formula (I), pharmaceutically acceptable salt, solvate or in vivo hydrolysable ester thereof for the treatment of asthma, allergic rhinitis, COPD, inflammatory bowel disease, irritable bowel syndrome, osteoarthritis, osteoporosis, rheumatoid arthritis, psoriasis or cancer.

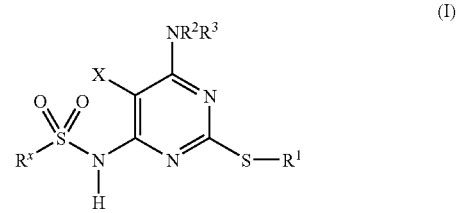

(I)

11 Claims, No Drawings

FOREIGN PATENT DOCUMENTS

| WO | WO 02/064096 | 8/2002 |
|----|--------------|--------|
| WO | WO 03/059893 | 7/2003 |
| WO | WO 2004/011143 | 2/2004 |
| WO | WO 2004/018435 | 3/2004 |
| WO | WO 2006/024823 | 3/2006 |

OTHER PUBLICATIONS

Bremner et al., "Therapy of Crohn's Disease in childhood", *Expert Opin. Pharmacother.* 3(7):809-825 (2002).
Bundgaard, Design of prodrugs, p. 1 (1985).
Cobo et al., "Reactivity of 6-Aminopyrimidin-4-(3H)-ones Towards Dimethyl Acetylenedicarboxylate (DMAD). Tandem Diels-Alder/Retro Diels-Alder (DA/RDA) Reaction in the Synthesis of 2-Aminopyridines", *Tetrahedron* 50(34):10345-10358 (1994).
Havlioglu et al., "Slit proteins, potential endogenous modulators of inflammation", *J NeuroVirology* 8:486-495 (2002).
Hübsch and Pfleiderer, "Synthesis and Properties of 8-Substituted 2-Thiolumazines", *Helvetica Chimica Acta* 71:1379-1391 (1988).
Inoue et al., "Preparation of 2-(alkylthio)-6-amino-5-(trifluoromethyl)-4(3H)-pyrimidinone derivatives as insecticides, acaricides, or agrochemical fungicides", CAPLUS Abstract 115:280054 (1991).
Inoue et al., "2-(Alkylthio)-6-amino-3(2H)-pyrimidinones", CAPLUS Abstract 106:18604 (1987).
Lee et al., "Characterization of Two High Affinity Human Interleukin-8 Receptors", *J. Biol. Chem.* 267(23):16283-16287 (1992).
Merritt et al., "Use of fluo-3 to measure cytosolic $Ca^{2+}$ in platelets and neutrophils. Loading cells with the dye, calibration of traces, measurements in the presence of plasma, and buffering of cytosolic $Ca^{2+}$", *Biochem. J.* 269:513-519 (1990).
Noell and Robins, "Aromaticity in Heterocyclic Systems. II. The Application of N.M.R. in a Study of the Synthesis and Structure of Certain Imidazo[1,2-c]Pyrimidines and Related Pyrrolo[2,3-d]Pyrimidines", Department of Chemistry, Arizona State University vol. 1: 34-41 (1964).
Nogimori et al., "Synthesis of 6-Anilino-2-thiouracils and Their Inhibition of Human Placenta Iodothyronine Deiodinase", *J. Med. Chem.* 28:1692-1694 (1985).
Raman et al., "Role of chemokines in tumor growth", *Cancer Letters* 256:137-165 (2007).
Robinson, "Medical Therapy of Inflammatory Bowel Disease for the 21st Century", *Eur J Surg Suppl* 582:90-98 (1998).
Rodríguez et al., "Aminopyrimidines and Derivatives.20. on the Acetylations of 5-Amino-4-Gly-cosylamino Pyrimidines", *Nucleosides & Nucleotides* 6(5):887-899 (1987).
Rostène et al., "Chemokines: a new class of neuromodulator?", *Nature Reviews Neuroscience* 8:895-904 (2007).
Simone, Oncology: Introduction, Cecil Textbook of Medicine, edited by Bennet, J.C., and Plum F., 20th ed., vol. 1, pp. 1004-1010 (1996).
Singh et al., "Immune therapy in inflammatory bowel disease and models of colitis", *British Journal of Surgery* 88:1558-1569 (2001).
Ulrich, Crystallization: 4. Crystal Characteristics, Kirk-Othmer Encyclopedia of Chemical Technology, Aug. 2002.
Vinkers et al., "SYNOPSIS: SYNthesize and OPtimize System in Silico", *J. Med. Chem.* 46:2765-2773 (2003).
Vippagunta et al., "Crystalline solids", *Advanced Drug Delivery Reviews* 48:3-26 (2001).
West, "Solid State Chemistry and its Applications", Wiley, New York, pp. 358 & 365 (1988).
Wolff, "Some considerations for prodrug design", Burger's Medicinal Chemistry and Drug Discovery, 5th ed., vol. I: Principles and Practice, John Wiley & Sons, pp. 975-977 (1995).
Zambeli and Kolbah, "Acetylation of some 2-(alkyl)thio-4-amino-6-hydroxy-pyrimidines", *Acta Pharm. Jug.* 21:91-96 (1971).
Budesinsky et al., "Sulfonamides with protracted antibacterial activity. II. Alkoxy- and Alkylthio-4-sulfanilamidopyrimidines", CS 159015; CA 84:105637, 1976. CAPLUS abstract.
Budesinsky et al., "4-Sulfanilamidopyrimidines", Cesko-Slovenska Farmacie (1961) 10:241-7; CA 55:137544, 1961. CAPLUS abstract.
Domori et al., "Synthesis and antibacterial activity of fluorine-containing pyrimidinylsulfanilamide derivatives", Yakugaku Zasshi (1967), 87(4):419-29; CA 67:90760, 1967. CAPLUS abstract.
Grigoryan et al., "Arylsulfonic acid derivatives. XV. Synthesis and antibacterial activity of some 4-amino-4-sulfonamidopyrimidines", Armyanskii Khimicheskii Zhurnal (1987), 40(7):443-7; CA 108:131739, 1988. CAPLUS abstract.
Spiteller et al., "Preparation of 2,6-disubstituted 4-sulfanilamidopyrimidines", Monatshefte fuer Chemie (1961) 92:183-92, CA 55:131336, 1961. CAPLUS abstract.
Ueda et al., "Sulfanilamide pyrimidine derivatives", JP 37004894, CA 59:85806, 1963. CAPLUS abstract.
USPTO Office Action in U.S. Appl. No. 11/574,340, mailed Jan. 4, 2010, 30 pages.
Fish & Richardson P.C., Amendment in Reply to Action of Jan. 4, 2010 in U.S. Appl. No. 11/574,340, filed Mar. 31, 2010, 11 pages.
USPTO Office Action in U.S. Appl. No. 11/574,340, mailed Apr. 29, 2010, 5 pages.
Fish & Richardson P.C., Amendment in Reply to Action of Apr. 29, 2010 in U.S. Appl. No. 11/574,340, filed Jun. 29, 2010, 6 pages.
USPTO Notice of Allowance in U.S. Appl. No. 11/574,340, mailed Jul. 13, 2010, 4 pages.
Nitta et al., "Pyrimidine Derivatives. I. Synthesis of a New Series of Sulthnilamides having Dialkylamino Groups in the Pyrimidine Nucleus", *Chem. Pharm. Bull.* 13(5):557-567 (1965).
USPTO Office Action in U.S. Appl. No. 12/947,916, mailed Apr. 11, 2011, 34 pages.
Fish & Richardson P.C., Terminal Disclaimer and Amendment in Reply to Action of Apr. 11, 2011 in U.S. Appl. No. 12/947,916, filed Jul. 11, 2011, 29 pages.

\* cited by examiner

PYRIMIDYL SULPHONE AMIDE DERIVATIVES AS CHEMOKINE RECEPTOR MODULATORS

CROSS-REFERENCE TO RELATED APPLICATIONS

This application is a continuation of U.S. application Ser. No. 10/522,871 filed on Aug. 18, 2005, now U.S. Pat. No. 7,582,644, which has a mail date of Jan. 26, 2005 and a 35 U.S.C. §371(c) date of Aug. 18, 2005 and is the National Stage of International Application No. PCT/GB2003/003175, filed Jul. 23, 2003, which in turn claims the benefit of Great Britain Application Serial No. 0217431.6, filed Jul. 27, 2002; each of these prior applications is incorporated herein by reference in its entirety.

The present invention relates to certain heterocyclic compounds, processes and intermediates used in their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved cysteine motif. At the present time, the chemokine superfamily comprises three groups exhibiting characteristic structural motifs, the C—X—C, C—C and C—X$_3$—C families. The C—X—C and C—C families have sequence similarity and are distinguished from one another on the basis of a single amino acid insertion between the NH-proximal pair of cysteine residues. The C—X$_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—X$_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family. These receptors represent good targets for drug development since agents which modulate these receptors would be useful in the treatment of disorders and diseases such as those mentioned above.

The present invention provides compounds of formula (1), a pharmaceutically acceptable salt, solvate or in vivo hydrolysable ester thereof:

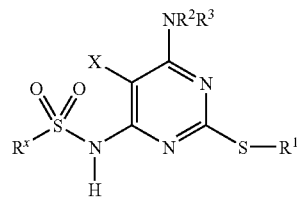

(1)

wherein $R^1$ is a group selected from $C_{3-7}$carbocyclyl, $C_{1-8}$alkyl, $C_{2-6}$alkenyl and $C_{2-6}$alkynyl; wherein the group is optionally substituted by 1, 2 or 3 substituents independently selected from fluoro, nitrile, —OR$^4$, —NR$^5$R$^6$, —CONR$^5$R$^6$, —COOR$^7$, —NR$^8$COR$^9$, —SO$_2$R$^9$, —SO$_2$NR$^5$R$^6$, —NR$^8$SO$_2$R$^9$, phenyl or heteroaryl; wherein phenyl and heteroaryl are optionally substituted by 1, 2 or 3 substituents independently selected from halo, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, $C_{1-6}$alkyl and trifluoromethyl;

wherein $R^2$ is $C_{3-7}$carbocyclyl, optionally substituted by 1, 2 or 3 substituents independently selected from:

(a) fluoro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$;

(b) a 3-8 membered ring optionally containing 1, 2 or 3 atoms selected from O, S, —NR$^8$ and whereby the ring is optionally substituted by $C_{1-3}$alkyl or fluoro; or (c) phenyl or heteroaryl, each of which is optionally substituted by 1, 2 or 3 substituents independently selected from halo, cyano, nitro, —OR$^4$, —NR$^5$R$^6$, —CONR$^5$R$^6$, —NR$^8$COR$^9$, —SO$_2$NR$^5$R$^6$, —NR$^8$SO$_2$R$^9$, $C_{1-6}$alkyl and trifluoromethyl;

or $R^2$ is a group selected from $C_{1-8}$alkyl, $C_{2-6}$alkenyl or $C_{2-6}$alkynyl wherein the group is substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-(phenyl)amino, N—$C_{1-6}$alkylcarbamoyl, N,N-di($C_{1-6}$alkyl)carbamoyl, N—($C_{1-6}$alkyl)-N-(phenyl)carbamoyl, carboxy, phenoxycarbonyl, —NR$^8$COR$^9$, —SO$_2$R$^{10}$, —SO$_2$NR$^5$R$^6$ and —NR$^8$SO$_2$R$^9$;

wherein $R^3$ is hydrogen or independently $R^2$;

$R^4$ is hydrogen or a group selected from $C_{1-6}$alkyl and phenyl, wherein the group is optionally substituted by 1 or 2 substituents independently selected from halo, phenyl, —OR$^{11}$ and —NR$^{12}$R$^{13}$;

$R^5$ and $R^6$ are independently hydrogen or a group selected from $C_{1-6}$alkyl and phenyl wherein the group is optionally substituted by 1, 2 or 3 substituents independently selected from halo, phenyl, —OR$^{14}$, —NR$^{15}$R$^{16}$, —COOR$^{14}$, —CONR$^{15}$R$^{16}$, —NR$^{15}$COR$^{16}$, —SO$_2$R$^{10}$, —SONR$^{15}$R$^{16}$ and NR$^{15}$SO$_2$R$^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring is optionally substituted by 1, 2 or 3 substituents independently selected from phenyl, —OR$^{14}$, —COOR$^{14}$, —NR$^{15}$R$^{16}$, —NR$^{15}$COR$^{16}$, —NR$^{15}$COR$^{16}$, —SO$_2$R$^{10}$, —SONR$^{15}$R$^{16}$, NR$^{15}$SO$_2$R$^{16}$ or $C_{1-6}$alkyl (optionally substituted by 1 or 2 substituents independently selected from halo, —NR$^{15}$R$^{16}$ and —OR$^{17}$ groups);

$R^{10}$ is hydrogen or a group selected from $C_{1-6}$alkyl or phenyl, wherein the group is optionally substituted by 1, 2 or 3 substituents independently selected from halo, phenyl, —OR$^{17}$ and —NR$^{15}$R$^{16}$; and each of R$^7$, R$^8$, R$^9$, R$^{11}$, R$^{12}$, R$^{13}$, R$^{14}$, R$^{15}$, R$^{16}$, R$^{17}$ is independently hydrogen, C$_{1-6}$alkyl or phenyl;

X is hydrogen, halo, cyano, nitro, hydroxy, C$_{1-6}$ alkoxy (optionally substituted by 1 or 2 substituents selected from halo, —OR$^{11}$ and —NR$^{12}$R$^{13}$), —NR$^5$R$^6$, —COOR$^7$, —NR$^8$COR$^9$, thio, C$_{1-6}$alkylthio (optionally substituted by 1 or 2 substituents selected from halo, —OR$^{17}$, —NR$^{15}$R$^{16}$), —SO$_2$R$^{10}$ or a group selected from C$_{3-7}$-carbocyclyl, C$_{1-8}$alkyl, C$_{2-6}$alkenyl or C$_{2-6}$alkynyl, wherein the group is optionally substituted by 1, 2 or 3 substituents independently selected from halo, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$ and —NR$^8$SO$_2$R$^9$;

R$^x$ is trifluoromethyl, —NR$^5$R$^6$, phenyl, napthyl, monocyclic or bicyclic heteroaryl wherein a heterorering may be partially or fully saturated and one or more ring carbon atoms may form a carbonyl group, and wherein each phenyl or heteroaryl group is optionally substituted by 1, 2 or 3 substituents independently selected from halo, cyano, nitro, —OR$^4$, —NR$^5$R$^6$, —CONR$^5$R$^6$, —COR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, C$_{1-6}$alkyl or trifluoromethyl;

or R$^x$ is a group selected from C$_{3-7}$-carbocyclyl, C$_{1-8}$alkyl, C$_{2-6}$alkenyl and C$_{2-6}$alkynyl whereby the group is optionally substituted by 1, 2 or 3 substituents independently selected from halo, —OR$^4$, —NR$^5$R$^6$, —CONR$^5$R$^6$, —COR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, phenyl or heteroaryl; and wherein each phenyl or heteroaryl group is optionally substituted by 1, 2 or 3 substituents independently selected from halo, cyano, nitro, —OR$^4$, —NR$^5$R$^6$, —CONR$^5$R$^6$, —COR$^7$, —COOR$^7$, —NR$^8$COR$^9$, —SR$^{10}$, —SO$_2$R$^{10}$, —SO$_2$NR$^5$R$^6$, —NR$^8$SO$_2$R$^9$, C$_{1-6}$alkyl or trifluoromethyl;

or R$^x$ and X together form a 4 to 8-membered sulfonamide ring optionally substituted by 1, 2 or 3 substituents independently selected from halo, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, phenyl or heteroaryl; wherein phenyl and heteroaryl are optionally substituted by 1, 2 or 3 substituents independently selected from halo, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, C$_{1-6}$alkyl and trifluoromethyl.

Certain compounds of formula (1) are capable of existing in stereoisomeric forms. It will be understood that the invention encompasses all geometric and optical isomers of the compounds of formula (1) and mixtures thereof including racemates.

The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of formula (1) or a salt, solvate or in vivo hydrolysable ester thereof may exhibit the phenomenon of tautomerism and that the formulae drawings within this specification can represent only one of the possible tautomeric forms. It is to be understood that the invention encompasses any tautomeric form and mixtures thereof and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of formula (1) and salts thereof can exist in solvated as well as unsolvated forms such as, for example, hydrated forms. It is to be understood that the invention encompasses all such solvated forms.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates, tartrates, oxalates, methanesulphonates or p-toluenesulphonates. Pharmaceutically acceptable salts of the invention may also include basic addition salts of the compounds of formula (1) as hereinbefore defined which are sufficiently acidic to form such salts. Such salts may be formed with an inorganic or organic base which affords a pharmaceutically acceptable cation. Such salts with inorganic or organic bases include for example an alkali metal salt, such as a lithium, sodium or potassium salt, an alkaline earth metal salt such as a calcium or magnesium salt, an ammonium salt or an organic amine salt, for example a salt with methylamine, dimethylamine, trimethylamine, triethylamine, piperidine, morpholine or tris-(2-hydroxyethyl) amine. Other basic addition salts include aluminium, zinc, benzathine, chloroprocaine, choline, diethanolamine, ethanolamine, ethyldiamine, meglumine, tromethamine or procaine.

The present invention further relates to an in vivo hydrolysable ester of a compound of formula (1). An in vivo hydrolysable ester of a compound of formula (1) which contains carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include C$_{1-6}$alkoxymethyl esters for example methoxymethyl, C$_{1-6}$alkanoyloxymethyl esters for example pivaloyloxymethyl, phthalidyl esters, C$_{3-8}$cycloalkoxycarbonyloxyC$_{1-6}$alkyl esters for example 1-cyclohexylcarbonyloxyethyl; 1,3-dioxolen-2-onylmethyl esters for example 5-methyl-1,3-dioxolen-2-onylmethyl; and C$_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s.

Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-($C_{1-4}$)alkylcarbamoyl and N-(di-($C_{1-4}$)alkylaminoethyl)-N—($C_{1-4}$)alkylcarbamoyl (to give carbamates); di-($C_{1-4}$)alkylaminoacetyl and carboxyacetyl. Examples of ring substituents on phenylacetyl and benzoyl include aminomethyl, ($C_{1-4}$)allylaminomethyl and di-(($C_{1-4}$)alkyl)aminomethyl, and morpholino or piperazino linked from a ring nitrogen atom via a methylene linking group to the 3- or 4-position of the benzoyl ring. Other interesting in-vivo hyrolysable esters include, for example, $R^4C(O)O(C_{1-6})$alkyl-CO—, wherein $R^4$ is for example, benzyloxy-($C_{1-4}$)alkyl, or phenyl). Suitable substituents on a phenyl group in such esters include, for example, 4-($C_{1-4}$)piperazino-($C_{1-4}$)alkyl, piperazino-($C_{1-4}$)alkyl and morpholino-($C_{1-4}$)alkyl.

In this specification the term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-3}$alkyl" includes methyl, ethyl, propyl and isopropyl and examples of "$C_{1-6}$alkyl" include the examples of "$C_{1-3}$alkyl" and additionally t-butyl, pentyl, 2,3-dimethylpropyl, 3-methylbutyl and hexyl. Examples of "$C_{1-8}$alkyl" include the examples of "$C_{1-6}$alkyl" and additionally heptyl, 2,3-dimethylpentyl, 1-propylbutyl and octyl. An analogous convention applies to other terms, for example "$C_{2-6}$alkenyl" includes vinyl, allyl, 1-propenyl, 2-butenyl, 3-butenyl, 3-methylbut-1-enyl, 1-pentenyl and 4-hexenyl and examples of "$C_{2-6}$alkynyl" includes ethynyl, 1-propynyl, 3-butyryl, 2-pentynyl and 1-methyl-pent-2-ynyl.

"$C_{3-7}$-carbocyclyl" is a saturated, partially saturated or unsaturated, monocyclic ring containing 3 to 7 carbon ring atoms wherein a —$CH_2$— group can optionally be replaced by a —C(O)—. Suitable examples of "carbocyclyl" are cyclopropyl, cyclopentyl, cyclobutyl, cyclohexyl, cyclohexenyl, 4-oxocyclohex-1-yl and 3-oxocyclohept-5-en-1-yl.

The term "halo" refers to fluoro, chloro, bromo and iodo.

Examples of "$C_{1-6}$alkoxy" include methoxy, ethoxy, propoxy, isopropoxy, butyloxy, pentyloxy, 1-ethylpropoxy and hexyloxy. Examples of "$C_{1-6}$alkylamino" include methylamino, ethylamino, propylamino, butylamino and 2-methylpropylmino. Examples of "di($C_{1-6}$alkyl)amino" include dimethylamino, N-methyl-N-ethylamino, diethylamino, N-propyl-N-3-methylbutylamino. Examples of "N—($C_{1-6}$alkyl)-N-(phenyl)amino" include N-methyl-N-phenylamino, N-propyl-N-phenylamino and N-(2-methylbutyl)-N-phenylamino. Examples of "N—($C_{1-6}$alkyl)carbamoyl" are N-methylcarbamoyl, N-ethylcarbamoyl and N-(2-ethylbutylcarbamoyl. Examples of "N—($C_{1-6}$alkyl)-N-(phenyl)carbamoyl" include N-methyl-N-phenylcarbamoyl, N-butyl-N-phenylcarbamoyl and N-(3-methylpentyl)-N-(phenyl)carbamoyl. Examples of "N,N-di($C_{1-6}$alkyl)carbamoyl" include N,N-dimethylcarbamoyl, N-methyl-N-ethylcarbamoyl and N-propyl-N-(2-methylbutyl)carbamoyl. Examples of "$C_{1-6}$alkylthio" include methylthio, ethylthio, propylthio, butylthio and 2-methylbutylthio.

"Heteroaryl" is a monocyclic or bicyclic aryl ring containing 5 to 10 ring atoms of which 1, 2, 3 or 4 ring atoms are chosen from nitrogen, sulphur or oxygen. Examples of heteroaryl include pyrrolyl, furanyl, thienyl, thiazolyl, isothiazolyl, oxazolyl, isoxazolyl, imidazolyl, pyrazolyl, triazolyl, tetrazolyl, pyridyl, pyrimidinyl, pyrazinyl, pyridazinyl, triazinyl, benzfuranyl, benzthieno, indolyl, benzimidazolyl, benzoxazolyl, benzthiazolyl, indazolyl, benzisoxazolyl, benzisothiazolyl, benztriazolyl, quinolinyl, isoquinolinyl and naphthiridinyl. Conveniently heteroaryl is selected from imidazolyl, pyrazolyl, thiazolyl, isoxazolyl, furanyl, thienyl, isoxazolyl, or indazolyl.

Examples of "a 3-8 membered ring optionally containing 1, 2 or 3 atoms selected from O, S and $NR^8$" include oxetanyl, azetidinyl, benzodiazolyl, pyrrolidinyl, tetrahydrofuranyl, tetrahydrothiophenyl, tetrahydropyranyl, piperidinyl, piperazinyl, morpholinyl, homopiperidinyl and homopiperazinyl tetrahydrodioxanyl., such as oxetanyl, azetidinyl, pyrrolidinyl, tetrahydrofuranyl, tetrahydropyranyl, piperidinyl, piperazinyl, morpholinyl, homopiperidinyl and homopiperazinyl, further such as pyrrolidinyl, tetrahydropyridinyl, piperidinyl, piperazinyl, and morpholinyl.

Examples of "a 4- to 7-membered saturated heterocyclic ring system" include azetidinyl, pyrrolidinyl, piperidinyl, piperazinyl, homopiperazinyl and morpholinyl.

Where optional substituents are chosen from "1, 2 or 3" groups it is to be understood that this definition includes all substituents being chosen from one of the specified groups or the substituents being chosen from two or more of the specified groups. An analogous convention applies to substituents chosen from "1 or 2" groups.

Preferred values of $R^1$, $R^2$, $R^3$, X and $R^x$ are as follows. Such values may be used where appropriate with any of the definitions, claims or embodiments defined hereinbefore or hereinafter.

In one aspect of the present invention there is provided a compound of formula (1) as depicted above wherein $R^1$ is $C_{1-8}$alkyl optionally substituted by 1, 2 or 3 substituents independently selected from nitrile, phenyl or heteroaryl, wherein phenyl and heteroaryl are optionally substituted by 1, 2 or 3 substituents independently selected from halo, cyano, —$OR^4$, —$SR^{10}$, $C_{1-6}$alkyl and trifluoromethyl.

In another aspect of the invention $R^1$ is benzyl optionally substituted by 1, 2, or 3, such as 1 or 2 substituents independently selected from fluoro, chloro, bromo, methoxy, methyl and trifluoromethyl. A further aspect $R^1$ is benzyl.

In a further aspect $R^1$ is monofluorobenzyl such as 2-fluorobenzyl, monochlorobenzyl such as 3-chlorobenzyl, difluorobenzyl such as 2,3-difluorobenzyl, fluorochlorobenzyl such as 3-chloro-2-fluorobenzyl, trifluorobenzyl such as 2,3,4-trifluorobenzyl.

In one aspect of the invention $R^2$ is $C_{1-8}$alkyl substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N(phenyl)amino, N—$C_{1-6}$alkylcarbamoyl, N,N-di($C_{1-6}$alkyl)carbamoyl, N—($C_{1-6}$alkyl)-N-(phenyl)carbamoyl, carboxy, phenoxycarbonyl, —$NR^8COR^9$, —$SO_2R^{10}$, —$SO_2NR^5R^6$ and —$NR^8SO_2R^9$.

In another aspect $R^2$ is $C_{1-4}$alkyl substituted by 1 or 2 hydroxy groups, conveniently 1 hydroxy group.

In a further aspect $R^2$ is 2-hydroxy-1-methylethyl, 1-(hydroxymethyl)propyl, 2-hydroxy-1-(hydroxymethyl)ethyl, or 2-hydroxy-1,1-dimethylethyl, especially 2-hydroxy-1-methylethyl In one aspect of the invention $R^3$ is hydrogen.

In one aspect of the invention $R^4$ is hydrogen, $C_{1-4}$alkyl for example methyl, or phenyl.

In one aspect of the invention $R^5$ is hydrogen, $C_{1-4}$alkyl or phenyl.

In one aspect of the invention $R^6$ is hydrogen, $C_{1-4}$alkyl or phenyl.

In one aspect of the invention $R^{10}$ is hydrogen, $C_{1-4}$alkyl or phenyl.

In one aspect of the invention X is hydrogen, halo, cyano, nitro, hydroxy, thio, $C_{1-6}$alkylthio (optionally substituted by 1 or 2 substituents selected from halo, —$OR^{17}$, —$NR^{15}R^{16}$), $C_{1-8}$alkyl (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$).

In another aspect X is hydrogen, halo, cyano, nitro, hydroxy, thio, $C_{1-4}$ alkyl or $C_{1-4}$ alkoxy (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$), $C_{1-4}$ alkylthio or $C_{1-4}$ alkylamino (optionally substituted by 1 or 2 substituents selected from halo, —$OR^{17}$, —$NR^{15}R^{16}$), In another aspect X is hydrogen, halo or $C_{1-4}$ alkyl (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$), In another aspect X is hydrogen.

In one aspect of the invention $R^x$ is trifluoromethyl, —$NR^5R^6$, phenyl, napthyl, monocyclic or bicyclic heteroaryl wherein a heteroring may be partially or fully saturated and one or more ring carbon atoms may form a carbonyl group, and wherein each phenyl or heteroaryl group is optionally substituted by 1, 2 or 3 substituents independently selected from halo, cyano, nitro, —$OR^4$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl;

or $R^x$ is a group selected from $C_{3-7}$-carbocyclyl, $C_{1-8}$alkyl, $C_{2-6}$alkenyl and $C_{2-6}$alkynyl whereby the group is optionally substituted by 1, 2 or 3 substituents independently selected from halo, —$OR^4$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, phenyl or heteroaryl; and wherein each phenyl or heteroaryl group is optionally substituted by 1, 2 or 3 substituents independently selected from halo, cyano, nitro, —$OR^4$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl;

In a further aspect of the invention $R^x$ is phenyl, heteroaryl, —$NR^5R^6$ or a group selected from $C_{1-8}$alkyl whereby the group is optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, phenyl or heteroaryl; and wherein each phenyl or heteroaryl group is optionally substituted by 1, 2 or 3 substituents independently selected from halo, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl.

In a further aspect $R^x$ is methyl, phenyl, 1-methylimidazolyl, 1,2-dimethylimidazolyl, or isoxazolyl.

In a further aspect $R^x$ is methyl, phenyl or 1-methylimidazolyl or 1,2-dimethylimidazolyl.

In a further aspect $R^x$ is —$NR^5R^6$ such as azetidinyl, pyrrolidinyl, piperazinyl or morpholinyl.

A preferred class of compound is of formula (1) wherein;
$R^1$ is $C_{1-8}$alkyl optionally substituted by 1, 2 or 3 substituents independently selected from nitrile, phenyl or heteroaryl, wherein phenyl and heteroaryl are optionally substituted by 1, 2 or 3 substituents independently selected from halo, cyano, —$OR^4$, —$SR^{10}$, $C_{1-6}$alkyl and trifluoromethyl;

$R^2$ is $C_{1-8}$alkyl substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-(phenyl)amino, N—$C_{1-6}$ alkylcarbamoyl, N,N-di($C_{1-6}$alkyl)carbamoyl, N—($C_{1-6}$alkyl)-N-(phenyl)carbamoyl, carboxy, phenoxycarbonyl, —$NR^8COR^9$, —$SO_2R^{10}$, —$SO_2NR^5R^6$ and —$NR^8SO_2R^9$;

$R^3$ is hydrogen;

$R^4, R^5, R^6, R^7, R^8, R^9, R^{10}, R^{11}, R^{12}, R^{13}, R^{14}, R^{15}, R^{16}$ and $R^{17}$ are independently hydrogen, $C_{1-4}$alkyl or phenyl; and X is hydrogen, halo, cyano, nitro, hydroxy, thio, $C_{1-6}$alkylthio (optionally substituted by 1 or 2 substituents selected from halo, —$OR^{17}$, —$NR^{15}R^{16}$), $C_{1-8}$alkyl (optionally substituted by 1, 2 or 3 substituents independently selected from halo, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$ and —$NR^8SO_2R^9$);

$R^x$ is —$NR^5R^6$, phenyl, napthyl, monocyclic or bicyclic heteroaryl wherein a heteroring may be partially or fully saturated and one or more ring carbon atoms may form a carbonyl group, and wherein each phenyl or heteroaryl group is optionally substituted by 1, 2 or 3 substituents independently selected from halo, cyano, nitro, —$OR^4$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl;

or $R^x$ is $C_{1-8}$alkyl optionally substituted by 1, 2 or 3 substituents independently selected from halo, —$OR^4$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, phenyl or heteroaryl; and wherein each phenyl or heteroaryl group is optionally substituted by 1, 2 or 3 substituents independently selected from halo, cyano, nitro, —$OR^4$, —$NR^5R^6$, —$CONR^5R^6$, —$COR^7$, —$COOR^7$, —$NR^8COR^9$, —$SR^{10}$, —$SO_2R^{10}$, —$SO_2NR^5R^6$, —$NR^8SO_2R^9$, $C_{1-6}$alkyl or trifluoromethyl;

Another preferred class of compound is of formula (1) wherein;

$R^1$ is benzyl optionally substituted by 1, 2 or 3, such as 2, substituents independently selected from fluoro, chloro, bromo, methoxy, methyl and trifluoromethyl;

$R^2$ is $C_{1-4}$alkyl substituted by 1 or 2 hydroxy groups;

$R^3$ is hydrogen;

X is hydrogen; and $R^x$ is methyl, phenyl, 1-methylimidazolyl, 1,2-dimethylimidazolyl, isoxazolyl or N,N-dimethylamino. Alternatively $R^x$ is —$NR^5R^6$-such as azetidinyl, pyrrolidinyl piperazinyl, piperidinyl or morpholinyl In another class $R^1$ is benzyl optionally substituted by 3-chloro-2-fluoro, 2,3-difluoro or 2,3,4-trifluoro $R^2$ is 2-hydroxy-1-methylethyl $R^3$ is hydrogen X is hydrogen $R^x$ is azetidinyl, pyrrolidinyl or morpholinyl, N,N-dimethylamino, piperidinyl, methyl, 1-methylimidazolyl and 1,2-dimethylimidazolyl.

Convenient compounds of the invention include each exemplified compound, each selected independently and pharmaceutically acceptable salts, in vivo hydrolysable esters thereof.

Particular compounds of the invention include:

N-(2-[(3-Chloro-2-fluorobenzyl)thio]-6-{[(1R)-2-hydroxy-1-methyl ethyl]amino}-pyrimidin-4-yl)methanesulfonamide N-[2-[(3-Chloro-2-fluorobenzyl)thio]-6-[(2-hydroxy-1-methylethyl)amino]-4-pyrimidinyl]-4-morpholinesulfonamide N-[2-[[(3-Chloro-2-fluorophenyl)methyl]thio]-6-[(2-hydroxy-1-methylethyl)amino]-4-pyrimidinyl]-1,2-dimethyl-1H-imidazole-4-sulfonamide N-(2-[(2,3-Difluorobenzyl)thio]-6-{[(1R)-2-hydroxy-1-methylethyl]amino}pyrimidin-4-yl)piperidine-1-sulfonamide N-(2-[(2,3-Difluorobenzyl)thio]-6-{[(1R)-2-hydroxy-1-methylethyl]amino}pyrimidin-4-yl)pyrrolidine-1-sulfonamide N-(2-[(2,3-Difluorobenzyl)thio]-6-{[(1R)-2-hydroxy-1-methyl ethyl]amino}pyrimidin-4-yl)azetidine-1-sulfonamide N-{6-{[(1R)-2-Hydroxy-1-methylethyl]amino}-2-[(2,3,4-trifluorobenzyl)thio]-pyrimidin-4-yl}morpholine-4-sulfonamide N-(2-[(2,3-Difluorobenzyl)thio]-6-{[(1R)-2-hydroxy-1-methyl ethyl]amino}pyrimidin-4-yl)morpholine-4-sulfonamide N-(2-[(3-Chloro-2-fluorobenzyl)thio]-6-{[(1R)-2-hydroxy-1-methylethyl]amino}-pyrimidin-4-yl)azetidine-1-sulfonamide N-{6-{[(1R)-2-Hydroxy-1-methylethyl]amino}-2-[(2,3,4-trifluorobenzyl)thio]-pyrimidin-4-yl}azetidine-1-sulfonamide N'-(2-[(3-Chloro-2-fluorobenzyl)thio]-6-{[(1R)-2-hydroxy-1-methylethyl]amino}-pyrimidin-4-yl)-N,N-dimethylsulfamide, and N-[2-[[(3-Chloro-2-fluorophenyl)methyl]thio]-6-[(R)-(2-hydroxy-1-methylethyl)amino]-4-pyrimidinyl]-1-methyl-1H-imidazole-4-sulfonamide and pharmaceutically acceptable salts, solvates or in vivo hydrolysable esters thereof. Each of the above mentioned compound and the pharmaceutically acceptable salt, solvate or in vivo hydrolysable ester thereof, individually is a preferred aspect of the invention.

Further particular compounds of the invention include:

N-(2-[(2,3-difluorobenzyl)thio]-6-{[(1R)-2-hydroxy-1-methylethyl]amino}pyrimidin-4-yl)methanesulfonamide;

N-(2-[(2,3-difluorobenzyl)thio]-6-{[(1R)-2-hydroxy-1-methylethyl]amino}pyrimidin-4-yl)-1-methyl-1H-imidazole-4-sulfonamide;

N-(2-(benzylthio)-6-{[(1R)-2-hydroxy-1-methylethyl]amino}pyrimidin-4-yl)-methanesulfonamide; and N-(2-(benzylthio)-6-{[(1R)-2-hydroxy-1-methylethyl]amino}pyrimidin-4-yl)benzenesulfonamide;

and pharmaceutically acceptable salts, solvates or in vivo hydrolysable esters thereof. Each of the above mentioned compound and the pharmaceutically acceptable salt, solvate or in vivo hydrolysable ester thereof, individually is a preferred aspect of the invention.

The present invention further provides processes for the preparation of compounds of formula (1) as defined above which comprise:

Process 1
(a) Treating a Compound of Formula (2):

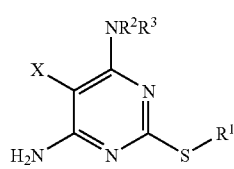

(2)

wherein $R^1$, $R^2$ and $R^3$ are as defined in formula (1) and X is hydrogen with sulfonyl chlorides ($R^xSO_2Cl$) where $R^x$ is as defined in formula (1).

and optionally thereafter (i), (ii), (iii), (iv), or (v) in any order.
i) removing any protecting groups;
ii) converting the compound of formula (1) into a further compound of formula (1)
iii) forming a salt
iv) forming a prodrug
v) forming an in vivo hydrolysable ester.

Reaction of compounds of formula (2) wherein $R^1$, $R^2$ and $R^3$ are as defined in formula (1) and X is hydrogen with sulfonyl chlorides ($R^xSO_2Cl$) can be carried out in the presence of a suitable base and solvent. Examples of suitable bases include trialkylamines, such as triethylamine or N,N-diisopropylethylamine or pyridine (optionally in the presence of a catalyst such as 4-dimethylaminopyridine). Suitable solvents include dichloromethane, pyridine, N,N-dimethylamides, 1-methyl-2-pyrolidone, and ethers such as tetrahydrofuran, 1,4-dioxane, glyme and diglyme. Preferably N,N-dimethylformamide is used. The temperature of the reaction can be performed between −10° C. and 100° C. Preferably N,N-diisopropylethylamine in dichloromethane or pyridine with 4-dimethylaminopyridine both at ambient temperature are used.

Compounds of formula (2) wherein $R^1$, $R^2$ and $R^3$ and X are as defined in formula (1), can be prepared from compounds of formula (3) wherein $R^1$ and X are as defined in formula (1) and L is halogen by treatment with nucleophilic amines $NR^2R^3$ as defined in formula (1) in the presence of a suitable base and solvent.

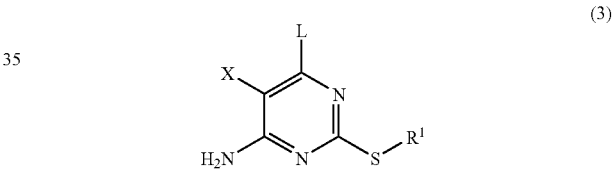

(3)

Examples of suitable bases include trialkylamines, such as triethylamine or N,N-diisopropylethylamine. Suitable solvents include N,N-dimethylamides, 1-methyl-2-pyrolidone, and ethers such as tetrahydrofuran, 1,4-dioxane, glyme and diglyme. The temperature of the reaction can be performed between 0° C. and 150° C. Preferably N,N-diisopropylethylamine in 1-methyl-2-pyrrolidinone at 120° C. is used. Compounds of formula (3) wherein $R^1$ and X are as defined in formula (1) and L is halogen may be prepared by treating a compound of formula (3) wherein $R^1$ and X are as defined in formula (1) and L is OH with a halogenating agent such as phosphorous oxychloride. The reaction may be carried out in the presence of an N,N-dialkylaniline, such as N,N-dimethylaniline at reflux.

Compounds of formula (3) wherein $R^1$ and X are as defined in formula (1) and L is OH;

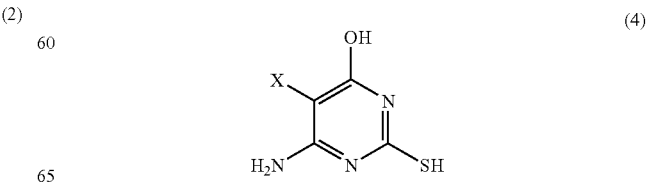

(4)

may be prepared from compounds of formula (4) wherein X is as defined in formula (1) by reaction with alkylhalides ($R_1A$) where $R_1$ is as defined in formula (1) and A is halogen in the presence of a suitable base and solvent.

Examples of suitable bases include the alkali metal hydroxides such as Li, Na, or K, or metal carbonates such as Li, Na, K or Cs, or metal acetates such as Li, Na, K or Cs, or metal alkoxides such as Li, Na, K-tert-butoxide. Suitable solvents include N,N-dimethylamides, 1-methyl-2-pyrrolidinone, ethers such as tetrahydrofuran, 1,4-dioxane, glyme and diglyme and alcohols such as methanol, ethanol and tert-butanol. Preferably potassium hydroxide in N,N-dimethylformamide at ambient temperature is used.

Compounds of formula (3) wherein $R^1$ and X are as defined in formula (1) and L is halogen;

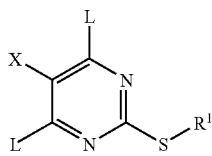

(5)

may also be prepared from compounds of formula (5) wherein X and $R^1$ are as defined in formula (1) and L is halogen by reaction with concentrated ammonium hydroxide solution in the presence of a suitable solvent. Suitable solvents include N-methyl-2-pyrolidone, acetonitrile and ethers such as tetrahydrofuran, 1,4-dioxane, glyme and diglyme. The temperature of the reaction can be performed between 0° C. and 150° C. Preferably acetonitrile at 60° C. is used.

Compounds of formula (5) wherein $R^1$ and X are as defined in formula (1) and L is halogen may be prepared from compounds of formula (5) wherein $R^1$ and X are as defined in formula (1) and L is OH by reaction with a halogenating agent such as phosphorous oxychloride. The reaction may be carried out in the presence of N,N-dimethylaniline at reflux.

Compounds of formula (5) wherein $R^1$ and X are as defined in formula (1) and L is OH;

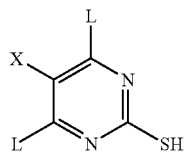

(6)

may be prepared from compounds of formula (6) wherein X are as defined in formula (1) and L is OH by reaction with alkylhalides ($R_1A$) where $R_1$ is as defined in formula (1) and A is halogen in the presence of a suitable base and solvent.

Examples of suitable bases include the alkali metal hydroxides such as Li, Na, or K, or metal carbonates such as Li, Na, K or Cs, or metal acetates such as Li, Na, K or Cs, or metal alkoxides such as Li, Na, K tert-butoxide. Suitable solvents include N,N-dimethylamides, 1-methyl-2-pyrolidone, ethers such as tetrahydrofuran, 1,4-dioxane, glyme and diglyme and alcohols such as methanol, ethanol and tert-butanol. Preferably potassium hydroxide in N,N-dimethylformamide at ambient temperature is used.

Compounds of formulae (4) and (6) are either commercially available, are well known in the literature or may be easily prepared using known techniques.

Process 2
(b) treating a compound of formula (7):

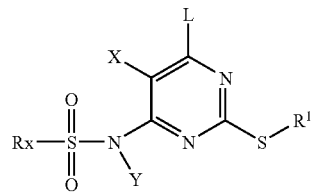

(7)

wherein $R^1$, $R^x$ and X are as defined in formula (1), L is a halogen and Y is either hydrogen or a protecting group with nucleophilic amines of the type $NR^2R^3$ as defined in formula (1) in the presence or absence of a suitable base and solvent.

and optionally thereafter (i), (ii), (iii), (iv) or (v) in any order:
i) removing any protecting groups;
ii) converting the compound of formula (1) into a further compound of formula (1)
iii) forming a salt
iv) forming a prodrug
v) forming an in vivo hydrolysable ester.

Examples of suitable bases include trialkylamines, such as triethylamine or N,N-diisopropylethylamine. Suitable solvents include N,N-dimethylamides, 1-methyl-2-pyrolidone, and ethers such as tetrahydrofuran, 1,4-dioxane, glyme and diglyme. The temperature of the reaction can be performed between 0° C. and 150° C. Preferably 1-methyl-2-pyrrolidinone at 80° C. is used.

Compounds of formula (7) wherein $R^1$, $R^x$ and X are as defined in formula (1) and L is halogen and Y is a protecting group or hydrogen;

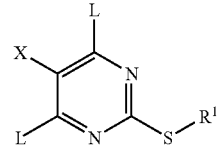

(5)

may be prepared from compounds of formula (5) wherein X and $R^1$ are as defined in formula (1) and L is a halogen by reaction with sulfonamides or sulfamides of formula $R^xSO_2NH_2$ where $R^x$ is as defined in formula (1) in the presence of a suitable base and solvent.

Examples of suitable bases include the alkali metal hydrides such as Na or K. Suitable solvents include N,N-dimethylamides, 1-methyl-2-pyrrolidinone, ethers such as tetrahydrofuran, 1,4-dioxane, glyme and diglyme. The temperature of the reaction may be performed between 0° C. and 100° C. Preferably sodium hydride in N,N-dimethylformamide at ambient temperature is employed.

Compounds of formula (5) can be prepared as described in process (1).

Compounds of formula $R^xSO_2NH_2$ where $R^x$ is $NR^5R^6$ may be prepared from sulfamide in the presence of a suitable solvent. Suitable solvents include N,N-dimethylamides, 1-methyl-2-pyrrolidinone, dichloromethane, chloroform, ethers such as tetrahydrofuran, 1,4-dioxane, glyme and diglyme and alcohols such as methanol, ethanol and tert-butanol. Preferably 1,4-dioxane is used at 110° C.

Process 3
(c) treating a compound of formula (8):

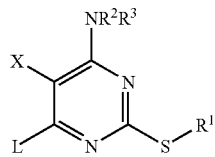

wherein R¹, R², R³, $R^x$ and X are as defined in formula (1) and L is halogen, with sulfonamides of formula $R^xSO_2NH_2$ where $R^x$ is as defined in formula (1) except $NR^5R^6$ in the presence of a suitable base and solvent.
and optionally thereafter (i), (ii), (iv) or (v) in any order:
i) removing any protecting groups;
ii) converting the compound of formula (1) into a further compound of formula (1)
iii) forming a salt
iv) forming a prodrug
v) forming an in vivo hydrolysable ester.

Examples of suitable bases include the alkali metal hydrides such as Na or K, or metal alkoxides such as Li, Na or K-tert-butoxide, or metal carbonates such as Na, K, Cs. Suitable solvents include N,N-dimethylamides, 1-methyl-2-pyrrolidinone, ethers such as tetrahydrofuran, 1,4-dioxane, glyme and diglyme. Preferably sodium hydride in N,N-dimethylformamide at ambient temperature is employed.

Compounds of formula (8) wherein R¹, R², R³ and X are as defined in formula (1) and L is halogen;

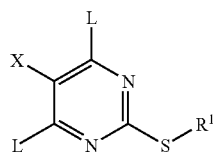

may be prepared from compounds of formula (5) wherein X and R¹ are as defined in formula (1) and L is a halogen by reaction with nucleophilic amines $NR^2R^3$ as defined in formula (1) in the presence a suitable base and solvent. Examples of suitable bases include trialkylamines, such as triethylamine or N,N-diisopropylethylamine Suitable solvents include N,N-dimethylamides, 1-methyl-2-pyrolidone, and ethers such as tetrahydrofuran, 1,4-dioxane, glyme and diglyme. The temperature of the reaction can be performed between 0° C. and 150° C. Preferably N,N-diisopropylethylamine in N-methylpyrrolidinone is used at room temperature.

Compounds of formula (5) can be prepared as described in process (1).

Compounds of formula $R^xSO_2NH_2$ where $R^x$ is as defined in formula (1), except $NR^5R^6$, are either commercially available or well known in the literature or may be prepared from the corresponding commercially available or well known in the literature sulfonyl chlorides $R^xSO_2Cl$.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (1) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Compounds of formulae (2), (3), (4) and (5), (6), (7), and (8) are either commercially available, are well known in the literature or may be easily prepared using known techniques.

A compound of formula (1) may be prepared from another compound of formula (1) by chemical modification. Examples of chemical modifications include standard alkylation, arylation, heteroarylation, acylation, sulphonylation, phosphorylation, aromatic halogenation and coupling reactions. These reactions may be used to add new substituents or to modify existing substituents. Alternatively, existing substituents in compounds of formula (1) may be modified by, for example, oxidation, reduction, elimination, hydrolysis or other cleavage reactions to yield other compounds of formula (1).

Novel intermediate compounds form a further aspect of the invention.

The compounds of formula (1) above may be converted to a pharmaceutically acceptable salt, solvate or in vivo hydrolysable ester thereof, as discussed above. The salt is preferably a basic addition salt.

The compounds of formula (1) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines. Examples of such conditions/diseases include (each taken independently):

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behchet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;

(4) (gastrointestinal tract) Coeliac disease, proctitis, eosinopilic gastro-enteritis, mastocytosis, Crohn's disease, ulcerative colitis, indeterminate colitis, microscopic colitis, inflammatory bowel disease, irritable bowel syndrome, non-inflammatory diarrhea, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft rejection) acute and chronic following, for example, transplantation of kidney, heart, liver, lung, bone marrow, skin and cornea; and chronic graft versus host disease;

(8) Cancers, especially non-small cell lung cancer (NSCLC), malignant melanoma, prostate cancer and squamous sarcoma, and tumour metastasis, non melanoma skin cancer and chemoprevention metastases;

(9) Diseases in which angiogenesis is associated with raised CXCR2 chemokine levels (e.g. NSCLC, diabetic retinopathy);

(10) Cystic fibrosis;

(11) Burn wounds & chronic skin ulcers;

(12) Reproductive Diseases (e.g. Disorders of ovulation, menstruation and implantation, Pre-term labour, Endometriosis);

(13) Re-perfusion injury in the heart, brain, peripheral limbs and other organs, inhibition of atherosclerosis.

Thus, the present invention provides a compound of formula (1), or a pharmaceutically-acceptable salt, solvate or an in vivo hydrolysable ester thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor.

Particular conditions which can be treated with the compounds of the invention are cancer, diseases in which angiogenesis is associated with raised CXCR2 chemokine levels, and inflammatory diseases such as asthma, allergic rhinitis, COPD, rheumatoid arthritis, psoriasis, inflammatory bowel diseases, osteoarthritis or osteoporosis.

As a further aspect of the present invention, certain compounds of formula (1) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides a compound of formula (1), or a pharmaceutically acceptable salt, solvate or in vivo hydrolysable ester thereof, as hereinbefore defined for use as a medicament.

In a still further aspect, the present invention provides the use of a compound of formula (1), or a pharmaceutically acceptable salt, solvate or in vivo hydrolysable ester thereof, as hereinbefore defined for use as a medicament for the treatment of human diseases or conditions in which modulation of chemokine receptor activity is beneficial.

In a still further aspect, the present invention provides the use of a compound of formula (1), or a pharmaceutically acceptable salt, solvate or in vivo hydrolysable ester thereof, as hereinbefore defined for use as a medicament for the treatment of asthma, allergic rhinitis, cancer, COPD, rheumatoid arthritis, psoriasis, inflammatory bowel diseases, osteoarthritis or osteoporosis.

In a further aspect, the present invention provides the use of a compound of formula (1), or a pharmaceutically acceptable salt, solvate or in vivo hydrolysable ester thereof, as hereinbefore defined in the manufacture of a medicament for use in therapy.

In a still further aspect, the present invention provides the use of a compound of formula (1), or a pharmaceutically acceptable salt, solvate or in vivo hydrolysable ester thereof, as hereinbefore defined in the manufacture of a medicament for the treatment of human diseases or conditions in which modulation of chemokine receptor activity is beneficial.

In a still further aspect, the present invention provides the use of a compound of formula (1), or a pharmaceutically acceptable salt, solvate or in vivo hydrolysable ester thereof, as hereinbefore defined in the manufacture of a medicament for the treatment of asthma, allergic rhinitis, cancer, COPD, rheumatoid arthritis, psoriasis, inflammatory bowel diseases, osteoarthritis or osteoporosis.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula, or a pharmaceutically acceptable salt, solvate or in vivo hydrolysable ester, as hereinbefore defined.

The invention also provides a method of treating an inflammatory disease, especially asthma, allergic rhinitis, COPD, rheumatoid arthritis, psoriasis, inflammatory bowel diseases, osteoarthritis or osteoporosis, in a patient suffering from, or at risk of, said disease, which comprises administering to the patient a therapeutically effective amount of a compound of formula (1), or a pharmaceutically acceptable salt, solvate or in vivo hydrolysable ester thereof, as hereinbefore defined.

For the above-mentioned therapeutic uses the dosage administered will, of course, vary with the compound employed, the mode of administration, the treatment desired and the disorder indicated.

The compounds of formula (1) and pharmaceutically acceptable salts, solvates or in vivo hydrolysable esters thereof may be used on their own but will generally be administered in the form of a pharmaceutical composition in which formula (1) compound/salt/solvate/ester (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (1), or a pharmaceutically acceptable salt, solvate or in vivo hydrolysable ester thereof, as hereinbefore defined, in association with a pharmaceutically acceptable adjuvant, diluent or carrier.

The invention further provides a process for the preparation of a pharmaceutical composition of the invention which comprises mixing a compound of formula (1), or a pharmaceutically acceptable salt, solvate or in vivo hydrolysable ester thereof, as hereinbefore defined, with a pharmaceutically acceptable adjuvant, diluent or carrier. The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

In addition to their use as therapeutic medicines, the compounds of formula (1) and their pharmaceutically acceptable salts, solvate or in vivo hydrolysable esters are also useful as pharmacological tools in the development and standardisation of in vitro and in vivo test systems for the evaluation of the effect of chemokine modulation activity in laboratory animals such as cats, dogs, rabbits, monkeys, rats and mice, as part of the search for new therapeutic agents.

The invention further relates to combination therapies wherein a compound of formula (1) or a pharmaceutically acceptable salts, solvate or in vivo hydrolysable ester thereof, or a pharmaceutical composition or formulation comprising a compound of formula (1) is administered concurrently or sequentially with therapy and/or an agent for the treatment of any one of asthma, allergic rhinitis, cancer, COPD, rheumatoid arthritis, psoriasis, inflammatory bowel disease, irritable bowel syndrome, osteoarthritis or osteoporosis.

In particular, for the treatment of the inflammatory diseases rheumatoid arthritis, psoriasis, inflammatory bowel disease, irritable bowel syndrome, COPD, asthma and allergic rhinitis the compounds of the invention may be combined with agents such as TNF-α inhibitors such as anti-TNF monoclonal antibodies (such as Remicade, CDP-870 and D.sub2.E.sub7.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold. For inflammatory bowel disease and irritable bowel disorder further convenient agents include sulphasalazine and 5-ASAs, topical and systemic steroids, immunomodulators and immunosuppressants, antibiotics, probiotics and anti-integrins.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY×1005.

The present invention still further relates to the combination of a compound of the invention together with a receptor antagonist for leukotrienes LTB.sub4., LTC.sub4., LTD.sub4., and LTE.sub4. selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention together with a PDE4 inhibitor including inhibitors of the isoform PDE4D.

The present invention still further relates to the combination of a compound of the invention together with a antihistaminic H.sub1. receptor antagonists such as cetirizine, loratadine, desloratadine, fexofenadine, astemizole, azelastine, and chlorpheniramine.

The present invention still further relates to the combination of a compound of the invention together with a gastroprotective H.sub2. receptor antagonist.

The present invention still further relates to the combination of a compound of the invention together with an α.sub1.- and α.sub2.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents such as ipratropium bromide; tiotropium bromide; oxitropium bromide; pirenzepine; and telenzepine.

The present invention still further relates to the combination of a compound of the invention together with a β.sub1.- to β.sub4.-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and CX$_3$CR1 for the C—X$_3$—C family.

The present invention still further relates to the combination of a compound of the invention together with antiviral agents such as Viracept, AZT, aciclovir and famciclovir, and antisepsis compounds such as Valant.

The present invention still further relates to the combination of a compound of the invention together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-B$_1$.- and B$_2$.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK$_1$. and NK$_3$. receptor antagonists selected from the group consisting of NKP-608C; SB-233412 (talnetant); and D-4418; (xx) elastase inhibitors selected from the group consisting of UT-77 and ZD-0892; (xxi) TNFδ converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate;

The compounds of the invention may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Pharmacological Data

Ligand Binding Assay $[^{125}I]$IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283-16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into FMK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 µg/ml soybean trypsin inhibitor, 3 mM benzamidine, 0.5 µg/ml leupeptin and 100 µg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM $NaH_2PO_4$), 0.1% (w/v) gelatin and 10% (v/v) glycerol.

All assays were performed in a 96-well MultiScreen 0.45 µm filtration plates (Millipore, U.K.). Each assay contained ~50 pM $[^{125}I]$IL-8 and membranes (equivalent to ~200,000 cells) in assay buffer [Tyrode's salt solution supplemented with 10 mM HEPES (pH 7.4), 1.8 mM $CaCl_2$, 1 mM $MgCl_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra □-counter.

The compounds of formula (1) according to the Examples 1-138 were found to have $pIC_{50}$ values of greater than (>) 5.0. For example, Examples 3, 4 and 116 were found to have $pIC_{50}$ values of 7.10, 7.10 and 6.80 respectively.

Intracellular Calcium Mobilisation Assay

Human neutrophils were prepared from EDTA-treated peripheral blood, as previously described (Baly et al. (1997) Methods in Enzymology 287 pp 70-72), in storage buffer [Tyrode's salt solution (137 mM NaCl, 2.7 mM KCl, 0.4 mM $NaH_2PO_4$) supplemented with 5.7 mM glucose and 10 mM HEPES (pH 7.4)].

The chemokine GROδ (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp 513-519). Cells were loaded for 1 hour at 37° C. in loading buffer (storage buffer with 0.1% (w/v) gelatin) containing 5 µM fluo-3 AM ester, washed with loading buffer and then resuspended in Tyrode's salt solution supplemented with 5.7 mM glucose, 0.1% (w/v) bovine serum albumin (BSA), 1.8 mM $CaCl_2$ and 1 mM $MgCl_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an $A_{50}$ concentration of GROδ and the transient increase in fluo-3 fluorescence ($\delta_{Ex}$=490 nm and $\delta_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophile.

The invention will now be illustrated by the following non-limiting Examples in which, unless stated otherwise:

(i) when given Nuclear Magnetic Resonance (NMR) spectra were measured on a Varian Unity Inova 300 or 400 MHz spectrometer. $^1$H NMR data is quoted in the form of delta values for major diagnostic protons, given in parts per million (ppm) relative to tetramethylsilane (TMS) as an internal standard.

(ii) Mass Spectrometry (MS) spectra were measured on a Finnigan Mat SSQ7000 or Micromass Platform spectrometer.

(iii) the title and sub-titled compounds of the Examples and methods were named using the ACD/Name program (version 4.55) from Advanced Chemical Development Inc, Canada.

(iv) Normal phase column chromatography and normal phase HPLC was conducted using a silica column. Reverse phase High Pressure Liquid Chromatography (HPLC) purification was performed using either a Waters Micromass LCZ with a Waters 600 pump controller, Waters 2487 detector and Gilson FC024 fraction collector or a Waters Delta Prep 4000 or a Gilson Auto Purification System, using a Symmetry, NovaPak or Ex-Terra reverse phase silica column.

(v) The following abbreviations are used:
AcOH acetic acid
$CHCl_3$ chloroform
DCM dichloromethane
DMF N,N-dimethylformamide
DMSO dimethylsulfoxide
$Et_2O$ diethyl ether
EtOAc ethyl acetate
$MgSO_4$ magnesium sulfate
NMP 1-methylpyrrolidin-2-one
THF tetrahydrofuran
$H_2O$ water

EXAMPLE 1

N-(2-[(2,3-difluorobenzyl)thio]-6-{[(1R)-2-hydroxy-1-methylethyl]amino}pyrimidin-4-yl)methane-sulfonamide

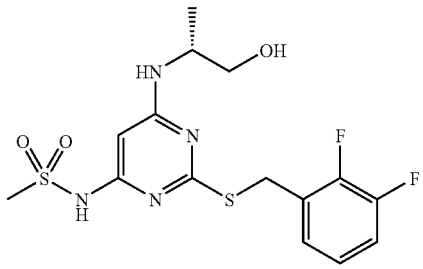

Methanesulfonyl chloride (0.16 ml) was added to a solution of the subtitle product of step iv) (0.40 g) and N,N-diisosopropylethylamine (0.5 ml) in DCM (15 ml) and stirring maintained for 2 h. The reaction solution was extracted with $H_2O$ (2×20 ml) and the organics combined, dried ($MgSO_4$) and concentrated to yield a brown oil. The residue was diluted in THF (10 ml) and treated with 1M tetrabutylammonium fluoride in TIE (2 ml) for 30 min at room temperature. The volatiles were removed in vacuo and the residue partitioned between EtOAc (30 ml) and saturated ammonium chloride solution (30 ml). The aqueous layer was further extracted with EtOAc (2×20 ml), the organics combined, dried ($MgSO_4$) and concentrated to yield a white solid. This material was further purified by silica gel chromatography and then reverse phase HPLC (acetonitrile/0.02M ammonium hydroxide (90% to 5% aqueous phase) to yield the title compound as a white solid. Yield: 25 mg.

MS APCI(+ve) 405 $[M+H]^+$ $^1H$ NMR $\delta_{(DMSO)}$ 7.41-7.12 (3H, m), 5.79 (1H, s), 4.70 (1H, br, s), 4.38 (2H, s), 3.41-3.25 (2H, m), 3.22 (3H, s), 1.05 (3H, d).

The intermediates for this compound were prepared as follows:

i) 6-Amino-2-[(2,3-difluorobenzyl)thio]pyrimidin-4(3H)-one

An aqueous solution of potassium hydroxide (4.61 g) in $H_2O$ (25 ml) was added to a suspension of 4-amino-6-hydroxy-2-mercaptopyrimidine monohydrate (11.26 g) in DMF (50 ml). Stirring was maintained for 30 min during which time a solution was obtained, before the dropwise addition of a solution of 2,3-difluorobenzyl bromide (14.46 g) in THF (10 ml). After stirring for 20 h the slurry was diluted with $H_2O$ (500 ml) and stirred for 30 min before filtering. The filtrate was washed with $H_2O$ (4×100 ml) and iso-hexane (4×100 ml) before drying in vacuo for 24 h to afford the subtitle compound as a white solid. Yield: 14.1 g.

MS APCI(+ve) 309 $[M+CH_3COO^-]^+$ ii) 6-Chloro-2-[(2,3-difluorobenzyl)thio]pyrimidin-4-amine

N,N-Dimethylaniline (5 ml) was added to a solution of the subtitle product of step i) in phosphorus oxychloride (50 ml) and heated at reflux for 2 h. The reaction was allowed to cool before pouring into hot $H_2O$ (500 ml) and stirring the mixture for 2 h. This mixture was extracted with DCM (3×250 ml) and the organics combined, dried ($MgSO_4$) and concentrated in vacuo to afford the subtitle compound as a green foam. This crude product was used directly in step iii). Yield: 12.3 g.

MS: APCI(+ve) 329 $[M+CH_3COO^-]^+$ iii) (2R)-2-({6-Amino-2-[(2,3-difluorobenzyl)thio]pyrimidin-4-yl}amino)propan-1-ol N,N-Diisopropylethylamine (1.92 ml) was added to a solution of R-alaninol (2.0 ml) and the subtitle product of step (1.9 g) in NMP (10 ml) and stirred at 100° C. for five days before pouring into $H_2O$ (200 ml) and filtration of the precipitate. This solid was dried in vacuo to afford the subtitle compound as a yellow solid. Yield: 1.80 g.

MS: APCI(+ve) 327 $[M+H]^+$ iv) N-((1R)-2-{[tert-Butyl(dimethyl)silyl]oxy}-1-methylethyl)-2-[(2,3-difluorobenzyl)-thio]pyrimidine-4,6-diamine Imidazole (1.2 g) was added to a solution of tert-butyldimethylsilyl chloride (2.83 g) and the subtitle product of step iii) (1.8 g) in DMF (10 ml). The reaction was stirred for 20 h before partitioning between EtOAc (100 ml) and $H_2O$ (200 ml). The aqueous was extracted further with EtOAc (2×100 ml), the organics combined, washed with $H_2O$ (100 ml), brine (100 ml), dried ($MgSO_4$) and concentrated in vacuo to a crude solid. This material was purified by column chromatography (50% $Et_2O$/iso-hexane) to afford the subtitle compound as a yellow oil. Yield: 1.80 g.

MS: APCI(+ve) 441 $[M+H]^+$

EXAMPLE 2

N-(2-[(2,3-Difluorobenzyl)thio]-6-{[(1R)-2-hydroxy-1-methylethyl]amino}pyrimidin-4-yl)-1-methyl-1H-imidazole-4-sulfonamide

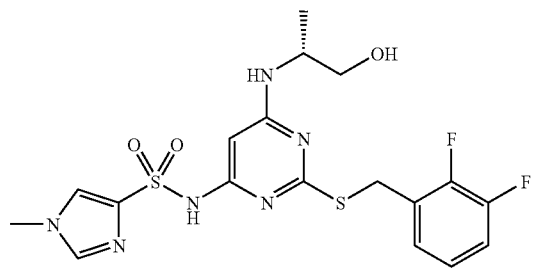

1-Methyl-1H-imidazole-4-sulfonyl chloride was added to a solution of the subtitle product of Example 1 step iv) (0.40 g) and 4-dimethylaminopyridine (0.12 g) in pyridine (10 ml) at room temperature and stirred for 20 h. The reaction mixture was partitioned between DCM (50 ml) and copper (II) sulfate solution (60 ml). The aqueous was extracted further with DCM, the organics combined, dried ($MgSO_4$) and concentrated in vacuo. The resulting oil was diluted in THF (10 ml) and treated with tetrabutylammonium fluoride (1M in THF, 2 ml) for 30 min at room temperature. The volatiles were removed in vacuo and the residue partitioned between EtOAc (20 ml) and saturated ammonium chloride solution (20 ml). The aqueous was further extracted with EtOAc (2×20 ml), the organics combined, dried ($MgSO_4$) and concentrated to yield a crude white solid. This material was further purified by reverse phase HPLC (acetonitrile/0.02M ammonium hydroxide (90% to 5% aqueous phase)) to yield the title compound as a white solid. Yield: 60 mg.

MS APCI(+ve) 471 [M+H]$^+$ $^1$H NMR δ$_{(DMSO)}$ 7.83 (m, 1H), 7.75 (s, 1H), 7.33 (m, 3H), 7.11 (m, 2H), 5.92 (s, 1H), 4.69 (s, 1H), 4.32 (s, 2H), 3.96 (s, 1H), 3.66 (s, 3H), 3.40-3.20 (m, 2H), 1.03 (d, 3H)

EXAMPLE 3

N-(2-(Benzylthio)-6-{[(1R)-2-hydroxy-1-methylethyl]amino}pyrimidin-4-yl)-methanesulfonamide

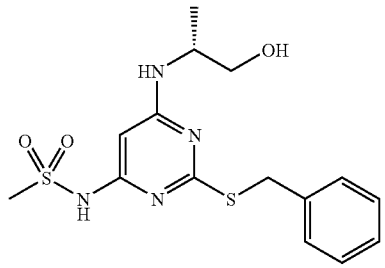

A solution of the subtitle product of step (0.18 g) in THF (10 ml) was treated with tetrabutylammonium fluoride (1M in THF, 2 ml) for 2 h at room temperature. The volatiles were removed in vacuo and the residue partitioned between EtOAc (20 ml) and saturated ammonium chloride solution (20 ml). The aqueous was further extracted with EtOAc (2×20 ml), the organics combined, dried (MgSO$_4$) and concentrated to yield a crude white solid. This material was further purified by reverse phase HPLC (acetonitrile/0.02M ammonium hydroxide (90% to 5% aqueous phase)) to yield the title compound as a white solid. Yield: 25 mg.

MS APCI(+ve) 369 [M+H]$^+$ $^1$H NMR δ$_{(DMSO)}$ 7.41 (d, 2H), 7.30 (t, 2H), 7.23 (t, 2H), 5.78 (s, 1H), 4.71 (t, 1H), 4.32 (s, 2H), 3.40 (dt, 1H), 3.29 (m, 1H), 3.18 (s, 3H), 1.07 (d, 3H).

The intermediates for this compound were prepared as follows:

i) (2R)-2-{[6-Amino-2-(benzylthio)pyrimidin-4-yl]amino}propan-1-ol

N,N-Diisopropylethylamine (6.0 ml) was added to a solution of R-alaninol (12.0 ml) and 2-(benzylthio)-6-chloropyrimidin-4-amine (1.9 g) (Nugent, R. A., et al. PCT Int. Appl. 1996. 252 pp. WO9635678-A1) in NMP (6 ml) and stirred at 100° C. for three days before pouring into H$_2$O (200 ml) and filtration of the precipitate. This solid was dried in vacuo to afford the subtitle compound as a pale sandy yellow solid. Yield: 4.1 g.

MS: APCI(+ve) 291 [M+H]$^+$ ii) 2-(Benzylthio)-N-((1R)-2-{[tert-butyl(dimethyl)silyl]oxy}-1-methylethyl)pyrimidine-4,6-diamine Imidazole (0.29 g) was added to a solution of tert-butyldimethylsilyl chloride (0.34 g) and the subtitle product of step i) (0.6 g) in DMF (10 ml). The reaction was stirred for 24 h before addition of a further equivalent of tert-butyldimethylsilyl chloride and imidazole. After stirring for an additional 24 h the reaction mixture was partitioned between EtOAc (100 ml) and H$_2$O (200 ml). The aqueous was extracted further with EtOAc (3×100 ml), the organics combined, washed with H$_2$O (100 ml), brine (100 ml), dried (MgSO$_4$) and concentrated to a crude solid. This material was purified by column chromatography (1:1 Et$_2$O/iso-hexane) to afford the subtitle compound as a yellow oil. Yield: 0.50 g.

MS: APCI(+ve) 405 [M+H]$^+$ iii) N-{2-(Benzylthio)-6-[((1R)-2-{[tert-butyl(dimethyl)silyl]oxy}-1-methylethyl)amino]-pyrimidin-4-yl}methanesulfonamide Methanesulfonyl chloride (85 µl) was added to a solution of the subtitle product of step (0.20 g) and N,N-diiosopropylethylamine (0.26 ml) in DCM (10 ml) at 0° C. The ice-bath was removed and stirring maintained for 2 h. The reaction solution was extracted with H$_2$O (2×20 ml) and the organics dried (MgSO$_4$) and concentrated to yield a brown oil. The residue was diluted in methanol (10 ml) and treated with potassium carbonate (0.15 g) for 2 h at room temperature. The volatiles were removed in vacuo and the residue partitioned between EtOAc (20 ml) and H$_2$O (20 ml). The aqueous was further extracted with EtOAc (2×20 ml), the organics combined, dried (MgSO$_4$) and concentrated to yield the subtitle compound as a crude white solid. This material was used directly in the next step. Yield: 0.23 g.

MS APCI(+ve) 483 [M+H]$^+$

EXAMPLE 4

N-(2-(Benzylthio)-6-{[(1R)-2-hydroxy-1-methylethyl]amino}pyrimidin-4-yl)benzenesulfonamide

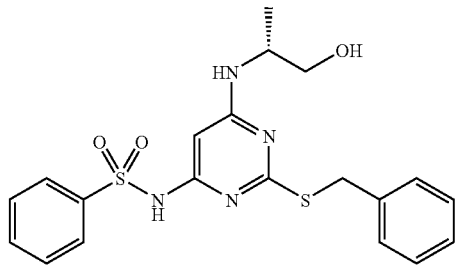

Phenylsulfonyl chloride (0.20 g) was added to a solution of the subtitle product of Example 3 step ii) (0.40 g) and 4-dimethylamino pyridine (0.17 g) in pyridine (10 ml) was stirred for 24 h at room temperature. The reaction was quenched with 10% potassium carbonate solution (10 ml) and the aqueous extracted with EtOAc (2×20 ml). The crude material was dissolved in THF (10 ml) and treated with tetrabutylammonium fluoride (1M in THF, 5 ml) for 15 min at room temperature. The reaction was quenched with 1M hydrochloric acid (10 ml) and the aqueous extracted with EtOAc (2×20 ml). The organics were then combined, washed with brine (50 ml), dried (MgSO$_4$) and concentrated to yield a crude gum which was purified by column chromatography (2% methanol/DCM) to afford a gum. This material was treated with ethanol (25 ml) and H$_2$O (5 ml) and the volatiles removed under reduced pressure to yield the title compound as a white solid. Yield: 0.39 g.

MS APCI(+ve) 431 [M+H]+

$^1$H NMR $\delta_{(DMSO)}$ 7.87 (d, 2H), 7.60 (m, 3H), 7.35 (d, 2H), 7.28 (t, 2H), 7.22 (m, 1H), 5.89 (s, 1H), 4.70 (s, 1H), 4.21 (s, 2H), 4.01 (s, 1H), 3.40-3.21 (m, 2H), 1.04 (d, 3H).

EXAMPLE 5

N-(2-(Benzylthio)-6-{[(1R)-1-methylpropyl]amino}pyrimidin-4-yl)-3,5-dimethylisoxazole-4-sulfonamide

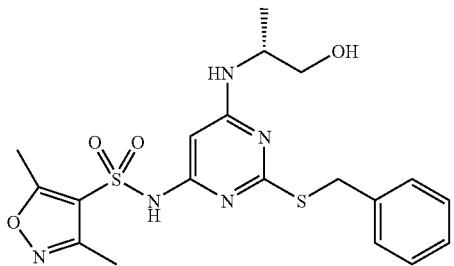

3,5-Dimethylisoxazole-4-sulfonyl chloride (0.60 g) was added to a solution of the subtitle product of Example 3 step ii) (50 mg) in pyridine (0.5 ml) and N,N-dimethylaminopyridine (16 mg). The reaction mixture was stirred overnight. To this reaction was added excess aqueous hydrochloric acid (1M) and stirred for 1 h. The solvent was evaporated and the residue diluted in EtOAc (100 ml). This was washed with H$_2$O (2×20 ml) and brine (10 ml). The organic layer was dried (MgSO$_4$) and concentrated to yield a white solid. This material was purified by reverse phase HPLC (gradient 90% to 5% 0.02M ammonium hydroxide/acetonitrile) to yield the title compound as a solid. Yield: 24 mg.

MS APCI(+ve) 450 [M+H]+

$^1$H NMR $\delta_{(DMSO)}$ 7.26-7.30 (5H, m), 5.73 (1H, s), 5.30 (1H, bs), 4.30 (2H, s), 4.0 (1H, br, s), 3.66 (1H, m), 3.54-3.59 (1H, m), 2.65 (3H, s), 2.39 (3H, s), 1.21 (3H, d).

EXAMPLE 6

N-(2-(Benzylthio)-6-{[(1R)-1-methylpropyl]amino}pyrimidin-4-yl)-1-phenylmethanesulfonamide

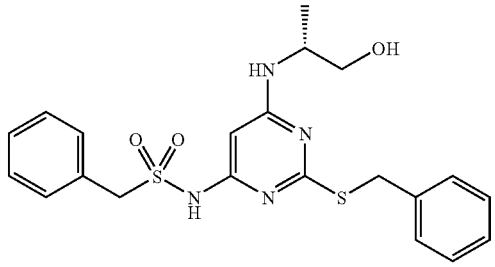

Phenylmethanesulfonyl chloride (0.28 g) was added to a solution of the subtitle product of Example 3 step ii) (0.1 g) in pyridine (1 ml) and N,N-dimethylaminopyridine (30 mg). The reaction mixture was stirred for 6 h. To the reaction mixture was added tetrabutylammonium fluoride (7 ml, 1M in THF) and stirred for 16 h. The solvent was evaporated and the residue diluted in EtOAc (100 ml) and hydrochloric acid (1M). This was washed with H$_2$O (2×20 ml) and brine (10 ml). The organics were dried (MgSO$_4$) and concentrated to yield a solid. This material was purified by reverse phase HPLC (90% to 5% 0.02M ammonium hydroxide/acetonitrile) to yield the title compound as a solid. Yield: 30 mg.

MS APCI(+ve) 445 [M+H]+

$^1$H NMR $\delta_{(CDCl3)}$ 7.24-7.40 (10H, m), 5.76 (1H, s), 5.02 (1H, bs), 4.43 (2H, s), 4.31 (2H, s) 4.02 (1H, br, s), 3.65-3.70 (1H, m), 3.51-3.56 (1H, m), 1.21 (3H, d).

EXAMPLE 7

N-(2-(Benzylthio)-6-{[(1R)-1-methylpropyl]amino}pyrimidin-4-yl)-2-chlorobenzenesulfonamide

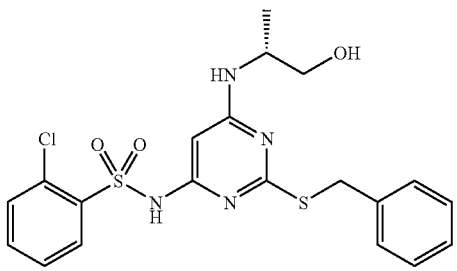

The title compound was synthesised according to the procedure of Example 6 using 2-chlorobenzenesulfonyl chloride (0.31 g), the subtitle product of Example 3 step ii) (0.1 g), N,N-dimethylaminopyridine (30 mg) and tetrabutylammonium fluoride (4 ml, 1M in THF) to yield the title compound as a white solid. Yield: 30 mg.

MS APCI(+ve) 465 [M+H]+

$^1$H NMR $\delta_{(CDCl3)}$ 8.14 (1H, d), 7.48 (2H, bs), 7.22-7.35 (6H, m), 5.84 (1H, s), 5.03 (1H, bs), 4.25 (2H, s), 3.98 (1H, bs) 3.54-3.66 (1H, m), 3.49-3.54 (1H, m), 1.21 (3H, d).

EXAMPLE 8

N-(2-(Benzylthio)-6-{[(1R)-1-methylpropyl]amino}pyrimidin-4-yl)-4-cyanobenzenesulfonamide

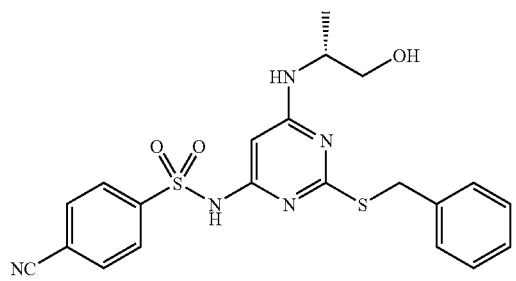

The title compound was synthesised according to the procedure of Example 6 using 4-cyanobenzenesulfonyl chloride (0.30 g), the subtitle product of Example 3 step ii) (0.1 g), N,N-dimethylaminopyridine (30 mg) and tetrabutylammonium fluoride (4 ml, 1M in THF) to yield the title compound as a white solid. Yield: 45 mg.

MS APCI(+ve) 456 [M+H]⁺

$^1$H NMR δ$_{(CDCl3)}$ 8.05 (2H, d), 7.74 (2H, d), 7.19-7.34 (5H, m), 5.85 (1H, s), 5.44 (1H, d), 4.13 (2H, s), 4.00 (1H, bs), 3.68-3.73 (1H, m), 3.54-3.59 (1H, m), 1.21 (3H, d).

EXAMPLE 9

N-(2-(Benzylthio)-6-{[(1R)-1-methylpropyl]amino}pyrimidin-4-yl)-4-chlorobenzenesulfonamide

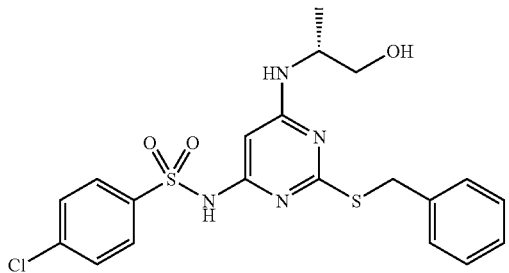

The title compound was synthesised according to the procedure of Example 6 using 4-chlorobenzenesulfonyl chloride (0.31 g), the subtitle product of Example 3 step ii) (0.1 g), N,N-dimethylaminopyridine (30 mg) and tetrabutylammonium fluoride (4 ml, 1M in THF) to yield the title compound as a white solid. Yield: 18 mg.

MS APCI(+ve) 465 [M+H]⁺

$^1$H NMR δ$_{(CDCl3)}$ 7.80 (2H, d), 7.40 (2H, d), 7.20-7.40 (5H, m), 5.90 (1H, s), 5.15 (1H, bs), 4.20 (2H, s), 4.00 (1H, bs) 3.60-3.80 (1H, m), 3.42-3.60 (1H, m), 1.21 (3H, d).

EXAMPLE 10

N-(2-(Benzylthio)-6-{[(1R)-1-methylpropyl]amino}pyrimidin-4-yl)-2-cyanobenzenesulfonamide

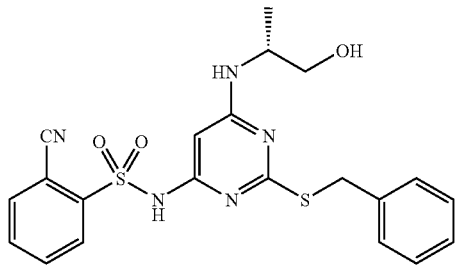

2-Cyanobenzenesulfonyl chloride (0.30 g) was added to the solution of the subtitle product of Example 3 step (0.1 g) in pyridine (1 ml) and N,N-dimethylaminopyridine (30 mg). The reaction mixture was stirred for 4 h. To the reaction mixture was added tetrabutylammonium fluoride (4 ml, 1M in THF) and stirred for 16 h. To this reaction was added aqueous hydrochloric acid (1M, 30 ml). The solvent was evaporated and the residue diluted in EtOAc (100 ml). This was washed with H₂O (3×20 ml) and brine (10 ml). The organic layer was dried (MgSO₄) and concentrated to yield a solid. The residue was purified by column chromatography (EtOAc/iso-hexane 7:3) followed by column chromatography (EtOAc) to yield the title compound. Yield: 30 mg.

MS APCI(+ve) 456 [M+H]⁺

$^1$H NMR δ (CDCl₃) 8.20 (1H, d), 7.58-7.62 (1H, m), 7.62-7.78 (1H, m), 7.78-8.00 (1H, m), 7.19-7.35 (5H, m), 5.80 (1H, s), 5.48 (1H, bs), 4.25 (2H, s), 3.50-3.80 (2H, m), 1.21 (3H, d).

EXAMPLE 11

N-(2-(Benzylthio)-6-{[(1R)-1-methylpropyl]amino}pyrimidin-4-yl)-3-cyanobenzenesulfonamide

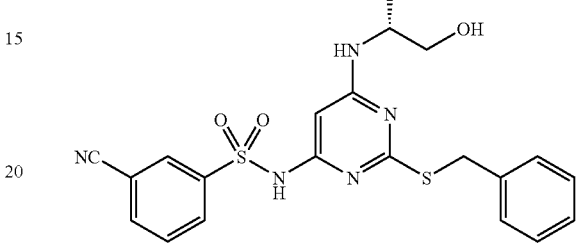

3-Cyanobenzenesulfonyl chloride (0.30 g) was added to the solution of the subtitle product of Example 3 step ii) (0.1 g) in pyridine (1 ml) and N,N-dimethylaminopyridine (30 mg). The reaction mixture was stirred for 4 h. To the reaction mixture was added tetrabutylammonium fluoride (4 ml, 1M in THF) and stirred for 16 h. To this reaction was added aqueous hydrochloric acid (1M, 30 ml). The solvent was evaporated and the residue diluted in EtOAc (100 ml). This was washed with H₂O (3×20 ml) and brine (10 ml). The organic layer was dried (MgSO₄) and concentrated to yield a solid. The residue was purified by column chromatography (EtOAc/iso-hexane 7:3 to 1:1) to yield the title compound as a white solid. Yield: 45 mg.

MS APCI(+ve) 456 [M+H]⁺

$^1$H NMR δ$_{(CDCl3)}$ 8.20 (1H, s), 8.15 (1H, d), 7.80 (1H, d), 7.60 (1H, t), 7.20-7.40 (6H, m), 5.90 (1H, s), 5.50 (1H, d), 4.32 (2H, s), 3.50-3.80 (2H, m), 1.21 (3H, d).

EXAMPLE 12

N-(2-(Benzylthio)-6-{[(1R)-1-methylpropyl]amino}pyrimidin-4-yl)-3-chlorobenzenesulfonamide

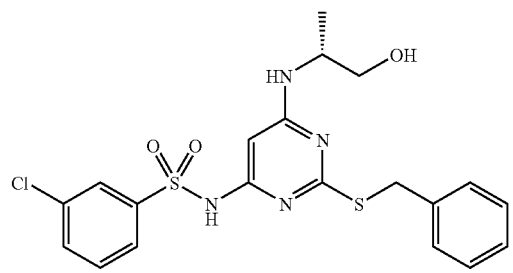

3-Chlorobenzenesulfonyl chloride (0.30 g) was added to the solution of the subtitle product of Example 3 step ii) (0.1 g) in pyridine (1 ml) and N,N-dimethylaminopyridine (30 mg). The reaction mixture was stirred for 4 h. To the reaction mixture was added tetrabutylammonium fluoride (4 ml, 1M in THF) and stirred for 16 h. To this reaction was added aqueous hydrochloric acid (1M, 30 ml). The solvent was evaporated and the residue diluted in EtOAc (100 ml). This was washed with H₂O (3×20 ml) and brine (10 ml). The organic layer was dried (MgSO₄) and concentrated to yield a solid. This material was purified by reverse phase HPLC (90% to 5% 0.02M ammonium hydroxide/acetonitrile) to yield the title compound as a solid. Yield: 30 mg.

MS APCI(+ve) 465 [M+H]³⁰

¹H NMR δ$_{(CDCl3)}$ 7.93 (1H, m), 7.80 (1H, d), 7.55 (1H, m), 7.45 (1H, t), 7.20-7.40 (5H, m), 5.90 (1H, s), 5.20 (1H, bd), 4.32 (2H, s), 4.00 (1H, bs), 3.60-3.70 (1H, m), 3.45-3.60 (1H, m), 1.21 (3H, d).

EXAMPLE 13

N-(5-{[(2-(Benzylthio)-6-{[(1R)-1-methylpropyl]amino}pyrimidin-4-yl)amino]sulfonyl}-4-methyl-1,3-thiazol-2-yl)acetamide

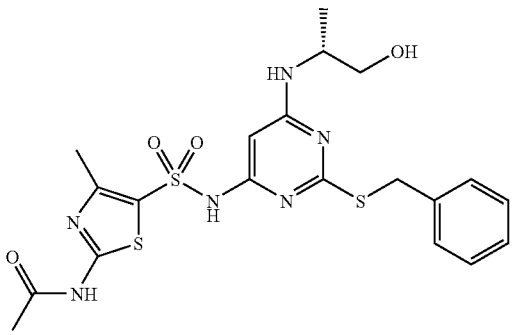

2-(Acetylamino)-1,3-thiazole-4-sulfonyl chloride (0.19 g) was added to a solution of the subtitle product of Example 3 step (0.2 g) in pyridine (4 ml) and N,N-dimethylaminopyridine (60 mg). The reaction mixture was stirred for 4 days. To this reaction more sulfonyl chloride (0.75 g) was added and stirred for 2 days. To this reaction was added aqueous hydrochloric acid (1M, 20 ml) and THF (20 ml). This was stirred for 18 h before the solvent was evaporated and the residue diluted in EtOAc (100 ml). This was washed with H₂O (3×20 ml) and brine (10 ml). The organic layer was dried (MgSO₄) and concentrated to yield a solid. This material was purified by reverse phase HPLC (90% to 5% 0.02M ammonium hydroxide/acetonitrile) to yield the title compound as a solid. Yield: 20 mg.

MS APCI(+ve) 509 [M+H]⁺

¹H NMR δ$_{(DMSO)}$ 7.20-7.37 (5H, m), 5.75 (1H, bs), 4.69 (1H, bs), 4.27 (2H, bs), 3.31-3.39 (2H, m), 2.50 (3H, s), 2.12 (3H, s), 1.21 (3H, d).

EXAMPLE 14

N-(2-(Benzylthio)-6-{[(1R)-1-methylpropyl]amino}pyrimidin-4-yl)-2-(methylsulfonyl)benzenesulfonamide

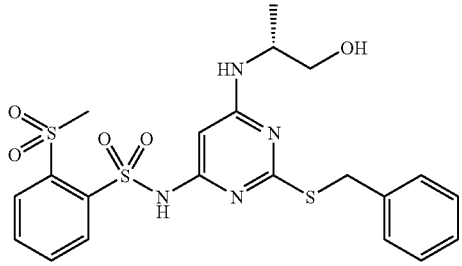

2-(Methylsulfonyl)benzenesulfonyl chloride (0.19 g) was added to a solution of the subtitle product of Example 3 step ii) (0.2 g) in pyridine (4 ml) and N,N-dimethylaminopyridine (59 mg). The reaction mixture was stirred for 4 days at room temperature. The solvent was removed, THF (2 ml) and sodium hydroxide (10%, 3 ml) added and stirring maintained for 2 h. The volatiles were removed in vacuo and the aqueous residue extracted with EtOAc (2×20 ml) and evaporated. To this residue was added aqueous hydrochloric acid (1M, 30 ml) and THF (10 ml). This was stirred at room temperature for 1 h. The mixture was extracted with EtOAc (2×30 ml). This was washed with H₂O (2×20 ml) and brine (20 ml). The organic layer was dried (MgSO₄) and concentrated to yield a solid. This material was purified by reverse phase HPLC (90% to 5% 0.02M ammonium hydroxide/acetonitrile) to yield the title compound as a solid. Yield: 30 mg.

MS APCI(+ve) 510 [M+H]⁺

¹H NMR δ$_{(CDCl3)}$ 8.31-8.34 (1H, dd), 8.23-8.26 (1H, dd), 7.30-7.40 (2H, d), 7.18-7.30 (3H, m), 6.18 (1H, s), 4.90 (1H, d), 4.20 (2H, s), 4.00 (1H, bs), 3.61-3.65 (1H, m), 3.45-3.60 (1H, m), 3.45 (3H, s), 1.21 (3H, d).

EXAMPLE 15

N-(2-(Benzylthio)-6-{[(1R)-1-methylpropyl]amino}pyrimidin-4-yl)-4-(methylsulfonyl)benzenesulfonamide

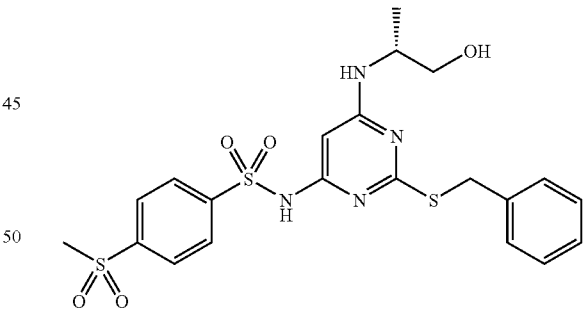

The title compound was synthesised according to the procedure of Example 14 using 4-methylsulfonylbenzenesulfonylchloride (0.19 g), the subtitle product of Example 3 step ii) (0.2 g) and N,N-dimethylaminopyridine (60 mg) to yield the title compound as a white solid. Yield: 60 mg.

MS APCI(+ve) 510 [M+H]⁺

¹H NMR δ$_{(CDCl3)}$ 8.09-8.12 (1H, d), 7.97-8.00 (2H, d), 7.20-7.30 (5H, m), 5.90 (1H, s), 5.65 (1H, bs), 4.28 (2H, s), 4.00 (1H, bs), 3.69-3.71 (1H, m), 3.49-3.60 (1H, m), 3.05 (3H, s), 1.17-1.19 (3H, d).

EXAMPLE 16

N-(2-(Benzylthio)-6-{[(1R)-1-methylpropyl]amino}pyrimidin-4-yl)propane-1-sulfonamide

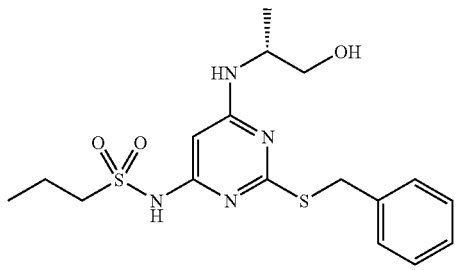

Propane-1-sulfonyl chloride (0.14 g) in DCM (1 ml) was added to a solution of the subtitle product of Example 3 step (0.2 g) in DCM (3 ml) and N,N-diisopropylethylamine (0.14 g) at 0° C. The reaction mixture was stirred for 24 h at room temperature. To the reaction mixture more N,N-diisopropylethylamine (0.14 g) was added and the reaction mixture was stirred for an additional 24 h. The DCM was removed under reduced pressure and the residue dissolved in THF (2 ml). To this mixture sodium hydroxide (10%, 2 ml) was added and stirred overnight. The reaction mixture was diluted with EtOAc (50 ml). The organic layer was separated from the aqueous layer and evaporated to dryness. To the residue was added aqueous hydrochloric acid (1M, 30 ml) and THF (10 ml). This was stirred at room temperature for 3 h. The mixture was extracted with EtOAc (2×50 ml). The organics were washed with brine (30 ml). The combined organic layers were dried (MgSO₄) and concentrated. This material was purified by reverse phase HPLC (90% to 5% 0.02M ammonium hydroxide/acetonitrile) to yield the title compound as a white solid. Yield: 30 mg.

MS APCI(+ve) 397 [M+H]$^+$ $^1$H NMR $\delta_{(CDCl_3)}$ 7.21-7.41 (5H, m), 5.94 (1H, s), 5.05 (1H, d) 4.30 (2H, s), 4.10 (1H, bs), 3.68-3.73 (1H, m), 3.53-3.60 (1H, m), 3.16-3.21 (2H, t), 1.77-1.90 (2H, m), 1.21 (3H, d). 1.00 (3H, t).

EXAMPLE 17

N-(2-(Benzylthio)-6-{[(1R)-1-methylpropyl]amino}pyrimidin-4-yl)-5-chloro-1,3-dimethyl-1H-pyrazole-4-sulfonamide

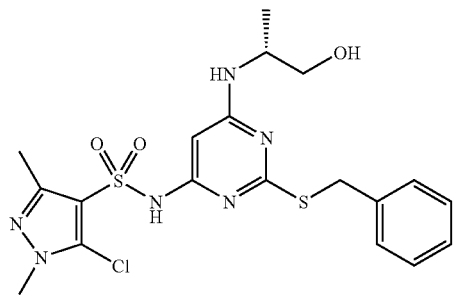

3-Chloro-1,5-dimethyl-1H-pyrazole-4-sulfonyl chloride (0.34 g) was added to the subtitle product of Example 3 step ii) (0.1 g) in pyridine (1 ml) and N,N-dimethylaminopyridine (30 mg). The reaction mixture was stirred overnight at room temperature. To this reaction was added tetrabutylammonium fluoride (4 ml, 1M in THF) and stirred for 3 h. To this mixture was added aqueous hydrochloric acid (30 ml, 1M) and extracted with EtOAc (2×30 ml) then brine (20 ml). The combined organic layer was dried (MgSO₄) and concentrated. This material was purified by column chromatography (EtOAc/iso-hexane (1:1) to EtOAc) to afford the title compound as a white solid. Yield: 30 mg.

MS APCI(+ve) 484[M+H]$^+$ $^1$H NMR $\delta_{(CDCl_3)}$ 7.22-7.37 (5H, m), 5.87 (1H, s), 4.95 (1H, br, s), 4.27 (2H, m), 4.0 (1H, br, s), 3.80 (3H, s), 3.66-3.70 (1H, m), 3.52-3.56 (1H, m), 2.44 (3H, s), 1.20 (3H, d).

EXAMPLE 18

N-(2-(Benzylthio)-6-{[(1R)-1-methylpropyl]amino}pyrimidin-4-yl)-1,3,5-trimethyl-1H-pyrazole-4-sulfonamide

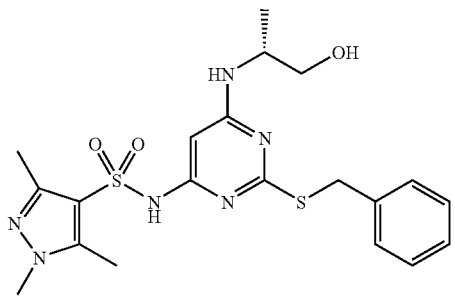

The title compound was synthesised according to the procedure of Example 17 using 1,3,5-trimethyl-1H-pyrazole-4-sulfonyl chloride (0.30 g), the subtitle product of Example 3 step ii) (0.1 g), N,N-dimethylaminopyridine (30 mg) and tetrabutylammonium fluoride (4 ml, 1M in THF) to yield the title compound as a white solid. Yield: 20 mg.

MS APCI(+ve) 463 [M+H]$^+$ $^1$H NMR $\delta_{(CDCl_3)}$ 7.21-7.36 (5H, m), 5.79 (1H, s), 4.95 (1H, d), 4.27 (2H, s), 4.0 (1H, br, s), 3.70 (3H, s), 3.64-3.68 (1H, m), 3.50-3.54 (1H, m), 2.41 (3H, s), 2.39 (3H, s), 1.20 (3H, d).

EXAMPLE 19

N-{2-(Benzylthio)-6-[(2-hydroxyethyl)amino]pyrimidin-4-yl}methanesulfonamide

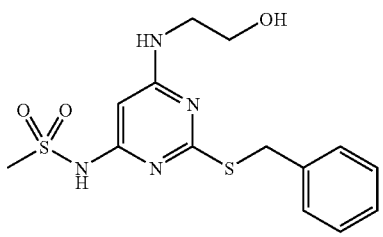

To the subtitle product of step iii) (0.20 g) was added ethanolamine (3.0 ml) and the reaction was heated at 100° C.

for 1 h. To the reaction was added EtOAc (50 ml) and H₂O (50 ml). The organic layer was separated and washed with H₂O (2×20 ml) and brine (20 ml). The organic layer was dried (MgSO₄), the solids were filtered and the solvent removed under reduced pressure to give a solid. This was purified by column chromatography (EtOAc/iso-hexane 1:1) to yield the title compound as a solid. Yield: 30 mg.

MS APCI(+ve) 355 [M+H]⁺

¹H NMR δ$_{(CDCl3)}$ 7.19-7.40 (5H, m), 5.91 (1H, s), 5.45 (1H, t), 4.33 (2H, s), 3.77 (2H, t), 3.52 (2H, m), 3.13 (3H, s).

The intermediates for this compound were prepared as follows:

i) 2-(Benzylthio)pyrimidine-4,6-diol

A solution of sodium hydroxide (3.30 g) in ethanol/H₂O (60 ml/60 ml) was added to 2-mercaptopyrimidine-4,6-diol (10.00 g) and the mixture stirred for 10 min. Benzyl bromide (13.45 g) was then added dropwise and the mixture heated at 60° C. for 2 h. The reaction was cooled to 0° C. for 1 h before the precipitate was filtered and washed with H₂O (100 ml) and then dried in vacuo to afford the subtitle compound as a cream solid. Yield: 15.0 g.

¹H NMR δ$_{(DMSO)}$ 7.41-7146 (2H, m), 7.20-7.40 (4H, m), 4.39 (2H, s).

ii) 2-(Benzylthio)-4,6-dichloropyrimidine

N,N-Dimethylaniline (7 ml) was added to the slurry of the subtitle product of step i) (5.0 g) in phosphorus oxychloride (35 ml) and heated at reflux for 10 h. The reaction was allowed to cool and excess phosphorus oxychloride was removed in vacuo before pouring onto ice. This mixture was extracted with EtOAc (200 ml) and washed with brine (2×100 ml), dried (MgSO₄) and concentrated in vacuo to afford the crude product. This crude product was purified by column chromatography (EtOAc/iso-hexane (10 to 20%)) to yield the title compound. Yield: 4.10 g.

¹H NMR δ$_{(CDCl3)}$ 7.40-7.42 (2H, m), 7.20-7.30 (4H, m), 4.38 (2H, s).

iii) N-[2-(Benzylthio)-6-chloropyrimidin-4-yl]methanesulfonamide

To methane sulphonamide (1.47 g) in DMF (30 ml) was added 60% sodium hydride (0.59 g) at room temperature and stirred for 1 h. To this mixture was then added the subtitle product of step and the mixture stirred at room temperature for 6 h. To the reaction mixture was added EtOAc (50 ml) and aqueous hydrochloric acid (50 ml, 1M). The organic layer was separated and washed with brine (20 ml), combined, dried (MgSO₄) and evaporated to dryness under reduced pressure. The residue was purified by column chromatography (20 to 50% EtOAc/iso-hexane) to afford the subtitle compound as a yellow oil. Yield: 1.60 g.

MS APCI (+ve) 330 [M+H]⁺

¹H NMR δ$_{(DMSO)}$ 7.40-7.42 (2H, d), 7.20-7.40 (3H, m), 6.70 (1H, s), 4.38 (2H, s), 3.30 (3H, s).

EXAMPLE 20

N-(2-(Benzylthio)-6-{[(1R)-1-(hydroxymethyl)propyl]amino}pyrimidin-4-yl)methanesulfonamide

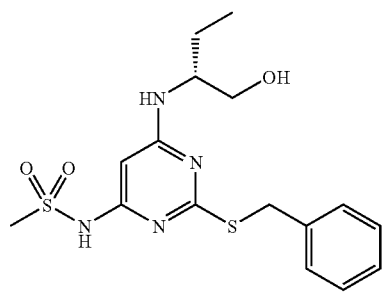

To the subtitle product of Example 19 step iii) (0.20 g) in NMP (1 ml) was added (2R)-2-aminobutan-1-ol (1.0 g) and the reaction was heated at 100° C. for 2 days. To the reaction was added EtOAc (50 ml) and H₂O (50 ml). The organic layer was separated and washed with H₂O (2×20 ml) and brine (20 ml). The organic layer was combined, dried (MgSO₄) and the solvent removed under reduced pressure to afford a solid. This was purified by column chromatography (EtOAc/iso-hexane 1:1) to give the title compound as a solid.

Yield: 15 mg.

MS APCI(+ve) 382 [M+H]⁺

¹H NMR δ$_{(DMSO)}$ 7.2-7.40 (2H, m), 7.20-7.30 (3H, m), 5.80 (1H, bs), 4.80 (1H, bs), 4.30 (2H, s), 3.85 (1H, bs), 3.30-3.45 (2H, m), 3.20 (3H, s), 1.41-1.64 (1H, m), 1.3-1.42 (1H, m), 0.83 (3H, t).

EXAMPLE 21

N-(2-(Benzylthio)-6-{[2-hydroxy-1-(hydroxymethyl)ethyl]amino}-pyrimidin-4-yl)methanesulfonamide

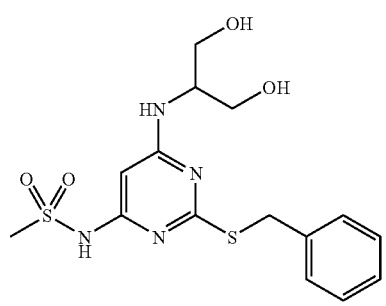

To a solution of the subtitle product of Example 19 step (0.20 g) in NMP (0.5 ml) was added 2-aminopropane-1,3-diol (1.0 g) and the reaction was heated at 100° C. for 2 days. To the reaction was added EtOAc (50 ml) and H₂O (50 ml). The organic layer was separated and washed with H₂O (2×20 ml) and brine (20 ml). The organic layer was dried (MgSO₄) and the solvent removed under reduced pressure to give a solid.

This was purified by column chromatography (1:1 EtOAc/iso-hexane then EtOAc) to give the title compound as a solid.
Yield: 20 mg.
MS APCI(+ve) 385 [M+H]$^+$
$^1$H NMR $\delta_{(DMSO)}$ 7.40-7.42 (2H, m), 7.20-7.30 (3H, m), 5.85 (1H, s), 4.63 (1H, s), 4.32 (2H, s), 3.40 (4H, bs), 3.20 (3H, s).

EXAMPLE 22

N-(2-(Benzylthio)-6-{[(2R)-2-hydroxypropyl]amino}pyrimidin-4-yl)methanesulfonamide

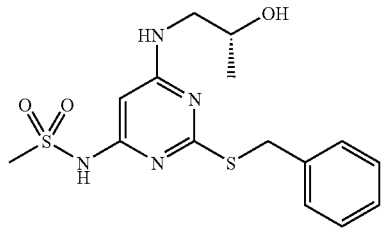

To the subtitle product of Example 19 step (0.20 g) in NMP (2 ml) was added (2R)-1-amino-2-propanol (0.46 g) and the reaction was heated at 80° C. for 6 h. To the reaction was added EtOAc (50 ml) and H$_2$O (20 ml). This solution was acidified with aqueous hydrochloric acid. The organic layer separated and washed with H$_2$O (2×20 ml), brine (20 ml) and the organic layer was dried (MgSO$_4$) and the solvent removed under reduced pressure to give a solid. This material was purified by reverse phase HPLC (90% to 5% 0.02 M ammonium hydroxide/acetonitrile) to yield the title compound as a solid. Yield: 20 mg.
MS APCI(+ve) 370 [M+H]$^+$
$^1$H NMR $\delta_{(CDCl3)}$ 7.2-7.47 (5H, m), 5.90 (1H, s), 5.40 (1H, bs), 4.32 (2H, s), 3.90-4.10 (1H, m), 3.40-3.50 (1H, m), 3.21 (1H, m), 3.10 (3H, bs), 1.20 (3H, d).

EXAMPLE 23

N'-(2-(Benzylthio)-6-{[(1R)-2-hydroxy-1-methylethyl]amino}pyrimidin-4-yl)-N,N-dimethylsulfamide

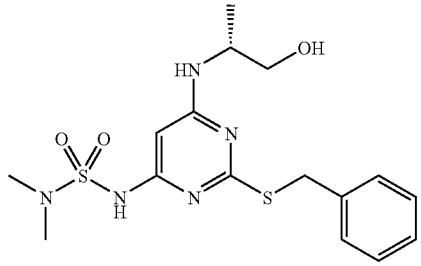

To the subtitle product of step i) (0.20 g) was added (R)-alaninol (2.0 ml) and the mixture heated at 80° C. for 2 days. The reaction mixture was diluted in EtOAc (50 ml) and acidified with aqueous hydrochloric acid (1M, 20 ml). The aqueous was extracted further with EtOAc (50 ml). The combined organic layers were washed with H$_2$O (3×20 ml) and brine (20 ml). The organic layer separated and further washed with H$_2$O (2×20 ml), brine (20 ml) and the organic layer was dried (MgSO$_4$) and the solvent removed under reduced pressure to give a solid. This material was purified by reverse phase HPLC (90% to 5% 0.02M ammonium hydroxide/acetonitrile) to yield the title compound as a solid. Yield: 20 mg.
MS APCI(+ve) 398 [M+H]$^+$
$^1$H NMR $\delta_{(CDCl3)}$ 7.2-7.40 (5H, m), 5.92 (1H, s), 4.98 (1H, bd), 4.32 (2H, s), 4.07 (1H, bs), 3.68-3.75 (1H, m), 3.50-3.60 (1H, m), 2.87 (6H, s), 1.20 (3H, d).

The intermediates for the title compound were prepared as follows:

i) N'-[2-(Benzylthio)-6-chloropyrimidin-4-yl]-N,N-dimethylsulfamide

To N,N-dimethylsulphonamide (1.0 g) in DMF (10 ml) was added 60% sodium hydride (0.22 g) at room temperature and the reaction heated to 50° C. for 1 h. This mixture was then allowed to cool to room temperature and the subtitle product of Example 19 step ii) was added in DMF (1 ml). To the reaction mixture was added EtOAc (50 ml) and aqueous hydrochloric acid (50 ml, 1M). The organic layer was separated and washed with brine (20 ml). The organic layer was dried (MgSO$_4$) and evaporated to dryness under reduced pressure. The residue was purified by column chromatography (EtOAc/iso-hexane 1:4) to afford the title compound as a yellow gum. Yield: 0.48 g.
MS APCI (+ve) 359 [M+H]$^+$
$^1$H NMR $\delta_{(CDCl3)}$ 7.40-7.42 (2H, m), 7.20-7.40 (3H, m), 6.80 (1H, s), 4.38 (3H, s), 2.92 (6H, s).

EXAMPLE 24

N-(2-(Benzylthio)-6-{[(1R)-2-hydroxy-1-methylethyl]amino}pyrimidin-4-yl)-1-methyl-2-oxoindoline-6-sulfonamide

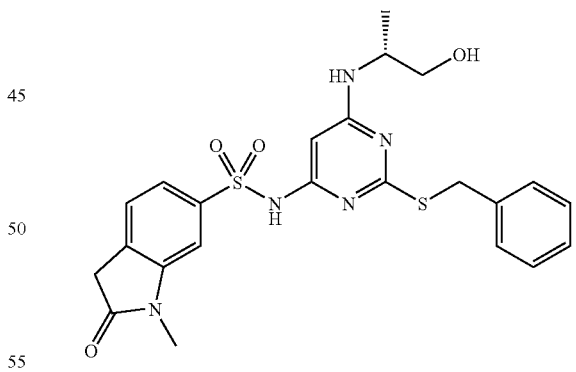

1-Methyl-2-oxoindoline-5-sulfonyl chloride (0.74 g) was added to the cooled solution of the subtitle product of Example 3 step ii) (0.25 g) in pyridine (5 ml) and N,N-dimethylaminopyridine (75 mg). The reaction mixture was stirred for 3 days at room temperature. To this mixture was added aqueous hydrochloric acid (30 ml, 1M) and extracted with EtOAc (2×30 ml), brine (20 ml). The organic layer was dried (MgSO$_4$) and concentrated. This material was purified by reverse phase HPLC (90% to 5% 0.02M ammonium hydroxide/acetonitrile) to yield the title compound as a solid.
Yield: 10 mg.

MS APCI(+ve) 500 [M+H]+

¹H NMR δ(DMSO) 7.80 (1H, d), 7.70 (1H, s), 7.19-7.32 (5H, m), 7.06 (1H, d), 5.82 (1H, s), 4.65 (1H, t), 4.20 (2H, s), 3.95 (1H, bs), 3.57 (2H, s), 3.20-3.41 (2H, m), 3.10 (3H, s), 1.21 (3H, d).

EXAMPLE 25

1-{[(2-(benzylthio)-6-{[(1R)-2-hydroxy-1-methyl-ethyl]amino}pyrimidin-4-yl)amino]sulfonyl}-N,N-dimethyl-L-prolinamide

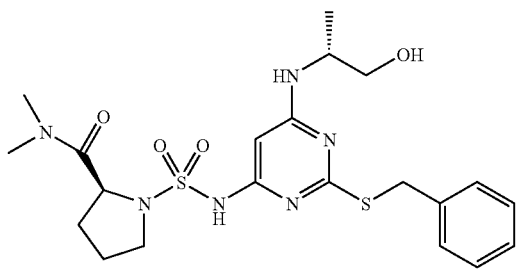

To the subtitle product of step iv) (0.50 g) was added (R)-alaninol (2 ml) and the mixture heated at 80-90° C. for 3 days. The reaction mixture was taken in EtOAc (1 L) and acidified with aqueous hydrochloric acid (1M, 20 ml). The aqueous was evaporated to give a residue which was purified by column chromatography (2% methanol/EtOAc) to give the title compound which was further purified by reverse phase HPLC (90% to 5% 0.02M ammonium hydroxide/acetonitrile) to afford the title compound as a white solid. Yield: 20 mg.

MS APCI(+ve) 495 [M+H]+

¹H NMR δ(DMSO) 7.39-7.42 (2H, m), 7.19-7.32 (3H, m), 5.70 (1H, s), 5.16 (1H, bs), 4.70 (1H, t), 4.30 (2H, m), 4.32 (2H, s), 3.38-3.45 (1H, m), 3.20-3.38 (3H, m), 3.04 (3H, s), 2.80 (3H, s), 1.95-2.10 (1H, m), 1.80-1.92 (1H, m), 1.62-1.80 (2H, m), 1.07 (3H, d).

The intermediates for this compound were prepared as follows:

i)
1-(tert-Butoxycarbonyl)-N,N-dimethyl-L-prolinamide

To 1-(tert-butoxycarbonyl)-L-proline (5.0 g) in DCM (50 ml) at 5° C. was added dicyclohexylcarbodiimide (5.22 g) and N-hydroxysuccinimide (2.91 g). The mixture was stirred at this temperature for 16 h. The solid was filtered and the filtrate cooled to 5° C. To this mixture was added triethylamine (9.80 ml) and dimethylamine hydrochloride (2.80 g). The mixture was stirred at room temperature for 2 days. H₂O (50 ml) was added and the phases were separated and the organics were washed with saturated sodium carbonate (2×20 ml) and brine (20 ml). This was then dried (MgSO₄) and evaporated to dryness to afford the title compound as a white solid. Yield: 6.0 g.

¹H NMR δ(CDCl3) 4.62-4.70 (1/2H, m), 4.50-4.60 (1/2H, m), 3.38-3.65 (2H, m), 3.15 (3H, 2s), 2.98 (3H, 2s), 1.90-2.21 (2H, m), 1.78-1.90 (2H, m), 1.40-1.42 (9H, 2s).

ii) N,N-Dimethyl-L-prolinamide hydrochloride

To the subtitle product of step i) (5.0 g) was added hydrochloric acid (20 ml, 4M). The mixture was stirred at room temperature for 3 h before the solvent was evaporated to afford the subtitle compound as a colourless solid. Yield: 3.50 g ¹H NMR δ(DMSO) 9.90 (1H, s, br), 8.40 (1H, s, br), 4.50-4.56 (1H, m), 3.00-3.30 (2H, m), 3.04 (3H, s), 2.90 (3H, s), 2.21-2.44 (1H, m), 1.71-1.95 (3H, m).

iii) 1-(Aminosulfonyl)-N,N-dimethyl-L-prolinamide

To a solution of the subtitle product of step (3.70 g) in dioxane (50 ml) was added triethylamine (2.02 g) and sulfamide (9.96 g). The mixture was heated at reflux for 3 days before the reaction mixture was cooled, filtered and washed with methanol (50 ml). The solvent was evaporated and the residue purified by column chromatography (2% methanol/EtOAc) to afford the subtitle compound as an oil. Yield: 1.70 g.

MS APCI(+ve) 222 [M+H]+

¹H NMR δ(DMSO) 6.63 (2H, bs), 4.58-4.61 (1H, m), 3.18-3.34 (2H, m), 3.04 (3H, s), 2.80 (3H, s), 2.00-2.10 (1H, m), 1.68-1.92 (3H, m).

iv) 1-({[2-(Benzylthio)-6-chloropyrimidin-4-yl]amino}sulfonyl)-N,N-dimethyl-L-prolinamide 60% Sodium hydride (0.42 g) was added to a solution of the subtitle product of step iii) (1.0 g) in DMF (10 ml) at 0° C. This mixture was stirred for 1 h before the addition of the subtitle product of Example 19 step ii) (1.60 g) in DMF (5 ml) was added dropwise. The mixture was allowed to reach room temperature and stirred for 3 days. To the mixture was added aqueous hydrochloric acid (1M) and extracted with EtOAc (2×100 ml). The organic layer was washed with H₂O (2×50 ml), the organic layer collected and concentrated causing the subtitle compound to precipitate out. This was filtered and washed with EtOAc (20 ml). Yield: 1.10 g.

MS APCI(+ve) 455 [M+H]+

¹H NMR δ(CDCl3) 7.42-7.46 (2H, m), 7.20-7.32 (3H, m), 7.02 (1H, s), 4.85-4.89 (1H, m), 4.32 (2H, s), 3.55-3.60 (2H, m), 3.05 (3H, s), 3.02 (3H, s), 2.33-2.4 (1H, m), 1.94-2.13 (3H, m).

EXAMPLE 26

1-{[(2-(Benzylthio)-6-{[(1R)-2-hydroxy-1-methyl-ethyl]amino}pyrimidin-4-yl)amino]sulfonyl}-N,N-dimethyl-D-prolinamide

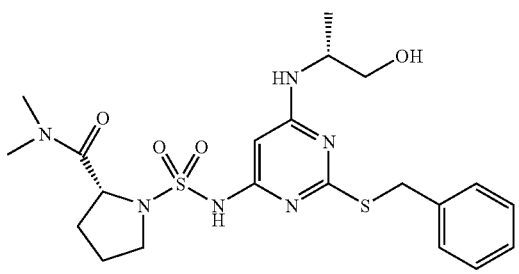

To the subtitle product of step iv) (1.0 g) was added R-alaninol (3 ml) and the mixture heated at 80-90° C. for 4 days. The reaction mixture was treated with EtOAc (100 ml) and acidified with aqueous hydrochloric acid (1M, 100 ml). The aqueous was separated and evaporated to give a residue which was purified by column chromatography (10% methanol/EtOAc) to give the title compound as a white solid. This material was further purified by reverse phase HPLC (90% to 5% 0.02M ammonium hydroxide/acetonitrile). Yield: 70 mg.

MS APCI(+ve) 495[M+H]$^+$ $^1$H NMR δ$_{(DMSO)}$ 7.36-7.41 (2H, m), 7.20-7.30 (3H, m), 5.70 (1H, s), 5.23 (1H, bd), 4.70 (1H, t), 4.27-4.37 (2H, m), 3.15-3.31 (4H, m), 3.04 (3H, s), 2.80 (3H, s), 2.00-2.10 (1H, m), 1.80-2.00 (1H, m), 1.62-1.80 (2H, m), 1.07 (3H, d).

The intermediates for the above compound were prepared as follows:

i) 1-(Benzyloxycarbonyl)-N,N-dimethyl-D-prolinamide

The subtitle compound was prepared according to the method of Example 25 step i) using 1-(benzyloxycarbonyl)-D-proline (3.90 g) in DCM (50 ml). Yield: 4.45 g.

MS APCI(+ve) 276[M+H]$^+$ ii) N,N-Dimethyl-D-prolinamide

To the subtitle compound of step i) (4.45 g) was added palladium hydroxide (0.20 g) and methanol (50 ml). The mixture was stirred under a hydrogen atmosphere (4 bar) at room temperature for 3 h before the catalyst was filtered through celite and the solvent was evaporated to afford the subtitle compound as a solid. Yield: 2.25 g.

$^1$H NMR δ$_{(CDCl3)}$ 3.81-3.90 (1H, m), 3.13-3.22 (1H, m), 3.00 (3H, s), 2.98 (3H, s), 2.74-2.87 (1H, m), 2.50 (1H, bs), 2.05-2.20 (1H, m), 1.59-1.90 (3H, m).

iii) 1-(Aminosulfonyl)-N,N-dimethyl-D-prolinamide

To a solution of the subtitle compound of step ii) (2.20 g) in dioxane (25 ml) was added sulfamide (7.20 g) and the mixture heated at reflux for 45 h. The reaction mixture was cooled and adsorbed on to silica gel and then purified by column chromatography (5% methanol/EtOAc) to afford the subtitle compound as an oil. Yield: 1.6 g.

MS APCI(+ve) 222 [M+H]$^+$ $^1$H NMR δ$_{(DMSO)}$ 6.63 (2H, bs), 4.58-4.61 (1H, m), 3.18-3.40 (2H, m), 3.04 (3H, s), 2.80 (3H, s), 2.00-2.10 (1H, m), 1.70-2.00 (3H, m).

iv) 1-({[2-(Benzylthio)-6-chloropyrimidin-4-yl]amino}sulfonyl)-N,N-dimethyl-D-prolinamide 60% Sodium hydride (0.42 g) was added to a solution of the subtitle product of step iii) (1.50 g) in DMF (20 ml) at 0° C. This mixture was stirred for 1 h and then a solution of the subtitle product of Example 19 step (1.60 g) in DMF (5 ml) was added dropwise. The mixture was allowed to reach room temperature and stirred there for 2 days. To the mixture was added aqueous hydrochloric acid (100 ml) and the resulting precipitate was filtered. This solid was then stirred with EtOAc (200 ml) and filtered to afford the subtitle compound as a solid. Yield: 2.0 g.

MS APCI(+ve) 456 [M+H]$^+$ $^1$H NMR δ$_{(DMSO)}$ 11δ1δs) 7.40-7.50 (2H, m), 7.20-7.40 (2H, m), 7.21-7.30 (1H, m) 6.70 (1H, s), 5.10-5.20 (1H, m), 4.32 (2H, s), 3.20-3.40 (2H, m), 3.04 (3H, s), 2.80 (3H, s), 2.00-2.10 (1H, m), 1.80-1.88 (1H, m), 1.70-1.88 (2H, m).

EXAMPLE 27

N-(2-[(3-Chloro-2-fluorobenzyl)thio]-6-{[(1R)-2-hydroxy-1-methylethyl]amino}-pyrimidin-4-yl)methanesulfonamide

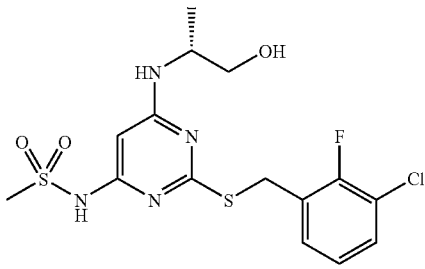

Methanesulfonyl chloride (0.15 ml) was added to a solution of the subtitle product of step (0.40 g) and N,N-diisopropylethylamine (0.53 ml) in DCM (15 ml) and stirring maintained for 30 min. A further portion of methanesulfonyl chloride (0.15 ml) and N,N-diiosopropylethylamine (0.53 ml) were added and stirring maintained for a further 30 min. The reaction solution was extracted with H$_2$O (2×20 ml) and the organics dried (MgSO$_4$) and concentrated to yield a brown oil. The residue was diluted in THF (7 ml) and treated with aqueous sodium hydroxide solution (1.5 ml of a 2.5M solution) for 1 h at room temperature. The reaction mixture was acidified with 2M hydrochloric acid solution to pH 1 and stirring maintained for 1 h before the mixture was neutralised with sodium hydroxide solution, concentrated onto silica gel and purified by column chromatography (Et$_2$O then EtOAc). The crude product was then purified by reverse phase HPLC (acetonitrile/0.02M ammonium hydroxide (90% to 5% aqueous phase)) to yield the title compound as a white solid. Yield: 0.12 g.

MS APCI(+ve) 421 [M+H]$^+$ $^1$H NMR δ$_{(DMSO)}$ 7.57 (1H, t), 7.48 (1H, t), 7.26 (1H, s), 7.17 (1H, t), 5.85 (1H, s), 4.71 (1H, s), 4.38 (2H, s), 3.98 (1H, s), 3.43-3.24 (2H, m), 3.20 (3H, s), 1.05 (3H, d).

The intermediates for the above compound were prepared as follows:

i) 6-Amino-2-[(3-chloro-2-fluorobenzyl)thio]pyrimidin-4(3H)-one

The subtitle compound was prepared according to the procedure of Example 1 step i) treating 4-amino-6-hydroxy-2-mercaptopyrimidine monohydrate (8.4 g) with 3-chloro-2-fluorobenzyl bromide (11.0 g) to afford the subtitle compound as a white solid. Yield: 14.1 g.

MS APCI(+ve) 286 [M+H]$^+$ ii) 6-Chloro-2-[(3-chloro-2-fluorobenzyl)thio]pyrimidin-4-amine

The subtitle compound was prepared from the product of step i) (2.00 g) according to the procedure of Example 1 step ii) to afford the subtitle product as a green foam which was used directly in the next step.

MS: APCI(+ve) 304 [M+H]$^+$ iii) N-((1R)-2-{[tert-Butyl(dimethyl)silyl]oxy}-1-methylethyl)-2-[(3-chloro-2-fluoro-benzyl)thio]pyrimidine-4,6-diamine N,N-Diisopropylethylamine (5.2 ml) was added to a solution of (R)-alaninol (2.56 ml) and the subtitle product of step in NMP (35 ml) and stirred at 100° C. for 24 h and then 140° C. for 24 h. After cooling to ambient temperature imidazole (2.60 g) and a solution of tert-butyldimethylsilyl chloride (2.60 g) in THF (10 ml) were added and stirring maintained for 1 h. The volatiles were removed in vacuo and the residue was purified by column chromatography (1:1 Et$_2$O/iso-hexane) to afford the subtitle compound as a yellow oil. Yield: 1.70 g.

MS: APCI(+ve) 457 [M+H]$^+$

EXAMPLE 28

N-(2-[(2,3-Dichlorobenzyl)thio]-6-{[(1R)-2-hydroxy-1-methylethyl]amino}pyrimidin-4-yl)methanesulfonamide

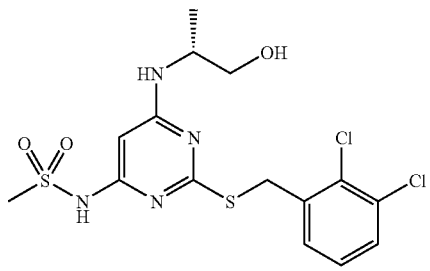

The title compound was synthesised from the subtitle product of step (0.4 g) according to the procedure of Example 27 to afford the title compound as a white solid.

Yield: 0.15 g.
MS APCI(+ve) 437 [M+H]$^+$
$^1$H NMR δ$_{(DMSO)}$ 10.55 (1H, s), 7.66 (1H, d), 7.55 (1H, dd), 7.31 (1H, t), 7.26 (1H, s), 5.78 (1H, s), 4.71 (1H, s), 4.46 (2H, s), 3.99 (1H, s), 3.41-3.24 (2H, m), 3.20 (3H, s), 1.05 (3H, d).

The intermediates for the above compound were prepared as follows:

i) 6-Amino-2-[(2,3-dichlorobenzyl)thio]pyrimidin-4(3H)-one

The subtitle compound was prepared according to the procedure of Example 1 step i) treating 4-amino-6-hydroxy-2-mercaptopyrimidine monohydrate (2.22 g) with 2,3-dichlorobenzyl bromide (3.30 g) to afford the subtitle compound as a white solid. Yield: 3.25 g.

MS APCI(+ve) 302 [M+H]$^+$ ii) 6-Chloro-2-[(2,3-dichlorobenzyl)thio]pyrimidin-4-amine

The subtitle compound was prepared from the product of step i) (2.00 g) according to the procedure of Example 1 step to afford the subtitle product as a green foam which was used directly in the next step MS: APCI(+ve) 320 [M+H]$^+$.

iii) N-((1R)-2-{[tert-Butyl(dimethyl)silyl]oxy}-1-methylethyl)-2-[(2,3-dichlorobenzyl)-thio]pyrimidine-4,6-diamine The subtitle compound was synthesised from the subtitle product of step ii) according to the procedure of Example 27 step Yield: 0.4 g.

MS: APCI(+ve) 473 [M+H]$^+$

EXAMPLE 29

N-(2-[(3-Chlorobenzyl)thio]-6-{[(1R)-2-hydroxy-1-methylethyl]amino}pyrimidin-4-yl)methanesulfonamide

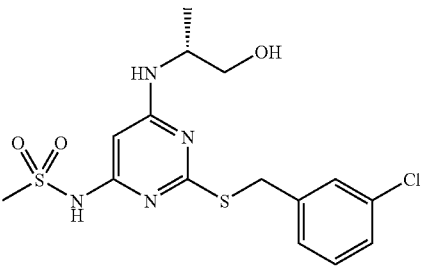

The title compound was prepared from the subtitle product of step iii) (0.4 g) according to the procedure of Example 27 as a white solid. Yield: 71 mg.

MS APCI(+ve) 403 [M+H]$^+$
$^1$H NMR δ$_{(DMSO)}$ 7.52-7.17 (4H, m), 5.78 (1H, s), 4.70 (1H, t), 4.32 (2H, dd), 3.97 (1H, s), 3.44-3.24 (2H, m), 3.18 (3H, s), 1.06 (3H, d).

The intermediates for the above compound were prepared as follows:

i) 6-Amino-2-[(3-chlorobenzyl)thio]pyrimidin-4(3H)-one

The subtitle compound was prepared according to the procedure of Example 1 step i) treating 4-amino-6-hydroxy-2-mercaptopyrimidine monohydrate (10.00 g) with 3-chlorobenzyl chloride (9.98 g) to afford the subtitle compound as a white solid. Yield: 15.00 g.

MS APCI(+ve) 268 [M+H]$^+$ ii) 6-Chloro-2-[(3-chlorobenzyl)thio]pyrimidin-4-amine

The subtitle compound was prepared from the product of step i) (2.00 g) according to the procedure of Example 1 step ii) to afford the subtitle product as a green foam which was used directly in the next step.

MS: APCI(+ve) 286 [M+H]$^+$ iii) N-((1R)-2-{[tert-Butyl(dimethyl)silyl]oxy}-1-methylethyl)-2-[(3-chlorobenzyl)thio]-pyrimidine-4,6-diamine The subtitle compound was synthesised from the subtitle product of Example 29 step according to the procedure of Example 27 step Yield: 0.4 g.

MS: APCI(+ve) 439 [M+H]$^+$

EXAMPLE 30

N-(2-[(2-Fluoro-4-methoxybenzyl)thio]-6-{[(1R)-2-hydroxy-1-methylethyl]amino}-pyrimidin-4-yl)methanesulfonamide

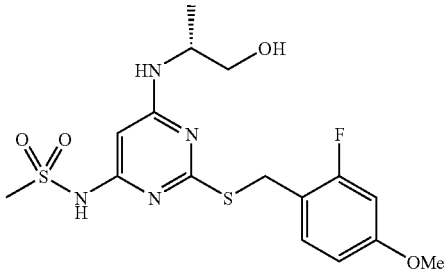

The title compound was synthesised from the subtitle product of Example 30 step iii) (0.4 g) according to the procedure of Example 27 as a white solid. Yield: 35 mg.

MS APCI(+ve) 403 [M+H]$^+$ $^1$H NMR $\delta_{(DMSO)}$ 7.45 (1H, t), 7.21 (1H, s), 6.81 (1H, dd), 6.73 (1H, dd), 5.77 (1H, s) 4.71 (1H, t), 4.27 (2H, s), 3.74 (3H, s), 3.44-3.21 (2H, m), 3.20 (3H, s), 1.08 (3H, d).

The intermediates for the above compound were prepared as follows:

i) 6-Amino-2-[(2-fluoro-4-methoxybenzyl)thio]pyrimidin-4(3H)-one

The subtitle compound was prepared according to the procedure of Example 1 step i) treating 4-amino-6-hydroxy-2-mercaptopyrimidine monohydrate (1.86 g) with 2-fluoro-4-methoxybenzyl chloride (2.00 g) to afford the subtitle compound as a white solid. Yield: 2.64 g.

MS APCI(+ve) 282 [M+H]$^+$ ii) 6-Chloro-2-[(2-fluoro-4-methoxybenzyl)thio]pyrimidin-4-amine

The subtitle compound was prepared from the product of Example 30 step i) according to the procedure of Example 1 step to afford the subtitle product as a green foam which was used directly in the subsequent step.

MS: APCI(+ve) 300 [M+H]$^+$ iii) N-((1R)-2-{[tert-Butyl-(dimethyl)silyl]oxy}-1-methylethyl)-2-[(2-fluoro-4-methoxy-benzyl)thio]pyrimidine-4,6-diamine The subtitle compound was synthesised from the subtitle product of step according to the procedure of Example 27 step iii). Yield: 0.4 g.

MS: APCI(+ve) 453 [M+H]$^+$

EXAMPLE 31

N-(2-[(3-Chloro-2-fluorobenzyl)thio]-6-{[(1R)-2-hydroxy-1-methylethyl]amino}-pyrimidin-4-yl)piperazine-1-sulfonamide

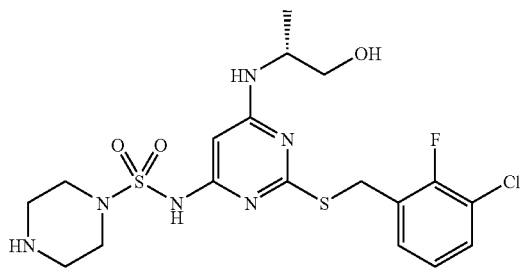

The subtitle product of step ii) (0.7 g) was diluted in (R)-alaninol (4 ml) and heated at 80° C. for 48 h. The product was purified through a plug of silica gel (1:1 EtOAc/isohexane then 90:9:1 EtOAc/methanol/N,N-diethylisopropylamine). The crude product was diluted in 1,4-dioxane (40 ml) and treated with HCl/1,4-dioxane (0.5 ml of a 4M solution) for 1 h before concentrating in vacuo and purifying the crude product by reverse phase HPLC (acetonitrile/0.02M ammonium hydroxide (90% to 5% aqueous phase)) to yield the title product as a white solid. Yield: 49 mg.

MS: APCI(+ve) 491 [M+H]$^+$ $^1$H NMR $\delta_{(DMSO)}$ 7.59 (1H, t), 7.46 (1H, t), 7.15 (1H, t), 7.06 (1H, s), 5.85 (1H, s), 4.69 (1H, t), 4.36 (2H, t), 3.89 (1H, s), 3.42-3.23 (2H, m), 3.05 (4H, m), 2.71 (4H, m), 1.05 (3H, d).

The intermediates for the above compound were prepared as follows:

i) tert-Butyl 4-(aminosulfonyl)piperazine-1-carboxylate

A mixture of tent-butyl-4-piperazine-1-carboxylate (1.47 g) and sulfamide (5.25 g) in 1,4-dioxan (50 ml) were heated at reflux for 48 h. The volatiles were removed in vacuo and the residue partitioned between EtOAc (100 ml) and H$_2$O (100 ml). The organics were recovered and the aqueous extracted further with EtOAc (3×100 ml). The organics were then combined, dried (MgSO$_4$) and concentrated. The crude material was triturated with diethyl ether and filtered to provide the subtitle compound as a white solid. Yield: 1.91 g $^1$H NMR $\delta_{(DMSO)}$ 6.80 (2H, s), 3.40 (4H, t), 2.90 (4H, t), 1.41 (9H, s).

ii) 2-[(3-Chloro-2-fluorobenzyl)thio]pyrimidine-4,6-diol

The subtitle compound was prepared by the method of Example 19 step i) using 2-mercaptopyrimidine-4,6-diol (20.0 g) and 3-chloro-2-fluorobenzyl bromide to afford the subtitle compound as a white solid. Yield: 36.2 g.

MS: APCI(+ve) 287 [M+H]$^+$ iii) 4,6-Dichloro-2-[(3-chloro-2-fluorobenzyl)thio]pyrimidine

N,N-Dimethylaniline (50 ml) was added to a slurry of the subtitle product of step (36.2 g) in phosphorus oxychloride (200 ml) and heated at reflux for 10 h. The reaction was allowed to cool and the excess phosphorus oxychloride removed in vacuo before pouring onto ice. This mixture was extracted with EtOAc (400 ml) and washed with brine (2×100 ml), the organics collected, dried (MgSO₄) and concentrated in vacuo to afford the crude product. This crude product was purified by flash chromatography (EtOAc/isohexane (2 to 5%)) to yield the subtitle compound as an oil. Yield: 6.2 g.

MS: APCI(−ve) 322 [M−H]⁺ iv) N-{6-Chloro-2-[(3-chloro-2-fluorobenzyl)thio] pyrimidin-4-yl}piperazine-1-sulfonamide 60% Sodium hydride (0.22 g) was added to a solution of the subtitle product of step i) (1.78 g) in DMF (10 ml) at 0° C. The reaction was removed from the cooling bath and stirred for 1 h before adding the subtitle product of step (1.46 g) as a solution in DMF (5 ml). The reaction was stirred overnight before concentrating in vacuo. The residue was partitioned between H₂O (50 ml) and EtOAc (50 ml) and the organics recovered, dried (MgSO₄) and concentrated in vacuo. The crude product was purified by flash column chromatography (20% then 30% EtOAc/iso-hexane) to yield the subtitle compound as a white solid. Yield: 0.7 g.

¹H NMR δ$_{(DMSO)}$ 11.64 (1H, s), 7.63-7.47 (2H, m), 7.19 (1H, t), 6.70 (1H, s), 4.47 (2H, s), 3.35 (8H, s), 1.40 (9H, s).

EXAMPLE 32

N-(2-[(3-Chloro-2-fluorobenzyl)thio]-6-{[(1R)-1-(hydroxymethyl)propyl]amino}-pyrimidin-4-yl)piperazine-1-sulfonamide

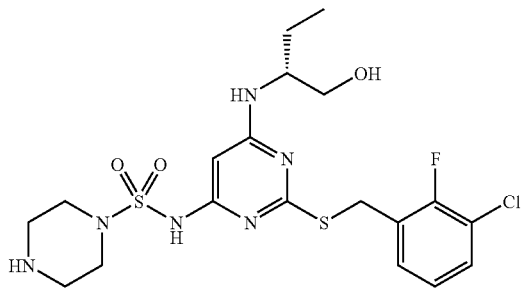

The subtitle product of step iv) (0.27 g) was diluted in trifluoroacetic acid (2 ml) and stirred for 20 min before removing the volatiles in vacuo. The residue was diluted in DCM (20 ml) and the volatiles again removed in vacuo. The title product was purified by reverse phase HPLC (acetonitrile/0.02M ammonium hydroxide (90% to 5% aqueous phase)) to yield the title compound as a white solid. Yield: 0.11 g.

MS: APCI(+ve) 505 [M+H]⁺

¹H NMR δ$_{(DMSO)}$ 7.59 (1H, t), 7.47 (1H, t), 7.15 (1H, t), 7.10 (1H, s), 5.89 (1H, s), 4.64 (1H, s), 4.36 (2H, s), 3.43-3.24 (2H, m), 3.08 (4H, m), 2.72 (4H, d), 1.60 (1H, m), 1.36 (1H, m), 0.82 (3H, t).

The intermediates for the above compound were prepared as follows:

i) tell-Butyl-4-[({6-chloro-2-[(3-chloro-2-fluorobenzyl)thio]pyrimidin-4-yl}{[2-(trimethylsilyl)ethoxy]methyl}amino)sulfonyl]piperazine-1-carboxylate 60% Sodium hydride (44 mg) was added to a solution of the subtitle product of Example 31 step iii) (0.40 g) in DMF (6 ml) at 0° C. Stirring was maintained for 10 min before the addition of [2-(chloromethoxy)ethyl](trimethyl)silane. The reaction was removed from the cooling bath and stirred for 2 h before the reaction was partitioned between H₂O (30 ml) and EtOAc (50 ml). The aqueous was extracted further with EtOAc (2×50 ml), the organics combined, dried (MgSO₄) and concentrated to afford the subtitle product as a colourless oil. Yield: 0.60 g.

MS: APCI(+ve) 682 [M+H]⁺ ii) tert-butyl-4-[((2-[(3-chloro-2-fluorobenzyl)thio]-6-{[(1R)-1-(hydroxymethyl)-propyl]amino}pyrimidin-4-yl){[2-(trimethylsilyl)ethoxy]methyl}amino)sulfonyl]-piperazine-1-carboxylate The subtitle product of step i) (0.60 g) was diluted in (2R)-2-aminobutan-1-ol (2 ml) and heated at 80° C. for 18 h. The subtitle compound was recovered as a colourless oil by flash column chromatography (EtOAc/iso-hexane mixtures). Yield: 0.40 g.

MS: APCI(+ve) 735 [M+H]⁺

EXAMPLE 33

N'-(2-[(3-Chloro-2-fluorobenzyl)thio]-6-{[(1R)-2-hydroxy-1-methylethyl]amino}-pyrimidin-4-yl)-N,N-dimethylsulfamide

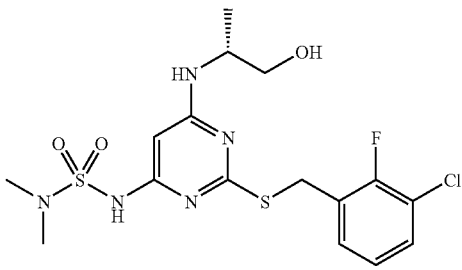

The subtitle product of step i) (0.7 g) was diluted in (R)-alaninol (4 ml) and heated at 80° C. for 48 h before partitioning between EtOAc/1M hydrochloric acid. The aqueous was further extracted with EtOAc (3×), the organics combined, washed with brine, dried (MgSO₄) and concentrated. The product was purified by column chromatography (25%, 40% EtOAc/iso-hexane then EtOAc) to yield the title compound as a colourless oil. Yield: 0.13 g.

MS: APCI(+ve) 450 [M+H]⁺

¹H NMR δ$_{(DMSO)}$ 10.43 (1H, s), 7.57 (1H, t), 7.47 (1H, dd), 7.29 (1H, s), 7.16 (1H, t), 5.87 (1H, s), 4.70 (1H, s), 4.37 (2H, t), 4.04 (1H, s), 3.43-3.24 (2H, m), 2.77 (6H, s), 1.05 (3H, d).

The intermediates for the above compound were prepared as follows:

i) N'-{6-chloro-2-[(3-chloro-2-fluorobenzyl)thio]pyrimidin-4-yl}-N,N-dimethyl-sulfamide 60% Sodium hydride (0.48 g) was added to a solution of N,N-dimethylsulfamide (1.05 g) in DMF (15 ml) and stirring maintained for 10 min before the addition of the subtitle product of Example 31 step iii) (3.56 g). The reaction was stirred for 18 h before the reaction was partitioned between H₂O (30 ml) and EtOAc (50 ml). The aqueous was extracted further with EtOAc (2×50 ml) the organics combined, washed with H₂O (100 ml), brine (50 ml), dried (MgSO₄) and concentrated. The crude product was purified by flash column chromatography (20% then 30% EtOAc/isohexane) to yield the subtitle compound as a white solid. Yield: 1.57 g.

$^1$H NMR $\delta_{(DMSO)}$ 11.49 (1H, s), 7.56 (1H, t), 7.51 (1H, t), 7.19 (1H, t), 6.69 (1H, s), 4.44 (2H, s), 2.83 (6H, s).

EXAMPLE 34

N-(2-[(3-Chloro-2-fluorobenzyl)thio]-6-{[(1R)-2-hydroxy-1-methylethyl]amino}pyrimidin-4-yl)-2-(dimethylamino)ethanesulfonamide

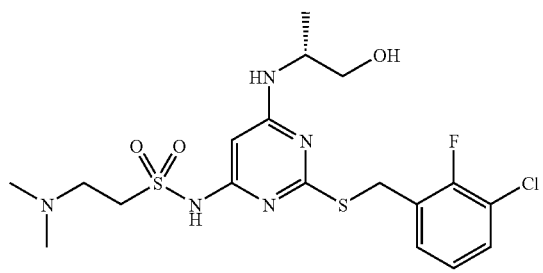

The subtitle product of step iv) (0.7 g) was diluted in (R)-alaninol (2.25 ml) and heated at 80° C. for 48 h. The product was purified by reverse phase HPLC (acetonitrile/ 0.02M ammonium hydroxide (90% to 5% aqueous phase)) to yield the title compound as a white solid. Yield: 46 mg.

MS: APCI(+ve) 478 [M+H]$^+$ $^1$H NMR $\delta_{(DMSO)}$ 7.6 (1H, t), 7.43 (1H, t), 7.15 (1H, t), 6.64 (1H, br, s), 5.54 (1H, s), 4.35 (2H, s), 3.80 (1H, s), 3.41-3.11 (6H, m), 2.09 (6H, s) and 1.08 (3H, d).

The intermediates for the above compound were prepared as follows:

i) Sodium 2-(dimethylamino)ethanesulfonate

Sodium ethylenesulfonate (18.2 ml, 25% aqueous solution w/w) and dimethylamine (4.43 ml, 40% aqueous solution w/w) were heated in a sealed finger tube at 105° C. for 48 h before concentrating in vacuo to yield the subtitle compound as a white solid. Yield: 9.80 g.

$^1$H NMR $\delta_{(CD3OD)}$ 3.05 (2H, m), 2.84 (2H, m) and 2.30 (6H, s).

ii) 2-(Dimethylamino)ethanesulfonyl chloride

Phosgene (12 ml, 1M in toluene) was added to a solution of the subtitle product of step i) in DCM (20 ml) and DMF (2.5 ml) and stirred for 3 h before concentrating in vacuo to afford the subtitle compound as an oil that was used directly in the next step. $^1$H NMR $\delta_{(CD3OD)}$ 3.30 (2H, m), 2.80 (2H, m) and 2.31 (6H, s).

iii) 2-(Dimethylamino)ethanesulfonamide

Ammonia was cautiously added to a cooled solution of the subtitle product of step ii) in THF (50 ml) and stirring maintained until all of the ammonia had evaporated before filtering off the product as a white solid. Yield: 0.88 g.

$^1$H NMR $\delta_{(CDCl3)}$ 3.20 (2H, t), 2.86 (2H, m) and 2.30 (6H, s).

iv) N-{6-Chloro-2-[(3-chloro-2-fluorobenzyl)thio]pyrimidin-4-yl}-2-(dimethylamino)ethanesulfonamide The subtitle compound was prepared by the method of Example 33 step i) from the reaction of the subtitle product of step iii) (0.8 g) and the subtitle product of Example 31 step (1.1 g) and used directly in the following step. Yield 0.7 g $^1$H NMR $\delta_{(CDCl3)}$ 7.48 (1H, t), 7.31 (1H, t), 7.02 (1H, t), 6.87 (1H, s), 4.38 (2H, s), 3.21 (2H, m), 2.83 (2H, m), 2.32 (3H, s), 2.25 (3H, s).

EXAMPLE 35

N-(2-[(3-chloro-2-fluorobenzyl)thio]-6-{[(1R)-2-hydroxy-1-methylethyl]amino}pyrimidin-4-yl)-4-methylpiperazine-1-sulfonamide

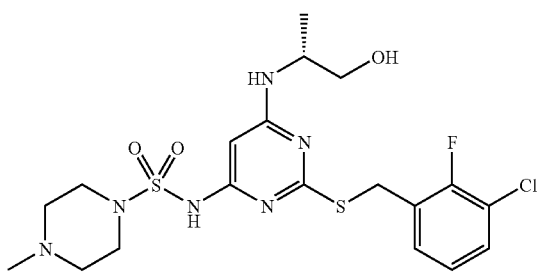

A solution of the product from step iv) (1.5 g) in (R)-alaninol (3 ml) was heated at 80° C. for 4 days. The resulting mixture was diluted with acetonitrile (5 ml) and purified by reverse phase HPLC (50% to 5% 0.02M ammonium hydroxide/methanol) to yield the title compound as a white solid. Yield: 1.0 g.

MS APCI(+ve) 506 [M+H]$^+$ $^1$H NMR $\delta_{(DMSO)}$ 10.60 (1H, bd), 7.60 (1H, m), 7.55 (1H, m), 7.47 (1H, bs), 7.19 (1H, t), 5.88 (1H, s), 4.72 (1H, t), 4.37 (2H, s), 3.40 (1H, m), 3.30 (2H, m), 3.10 (4H, m), 2.30 (4H, m), 2.10 (3H, s), 1.05 (3H, d).

The intermediates for this compound were prepared as follows:

i) 4-Methyl-1-piperazinesulfonamide

N-Methyl piperazine (5 ml) and sulfamide (11.26 g) in 1,4-dioxane (100 ml) were heated at reflux for 48 h. The solvent was evaporated under reduced pressure and the resulting solid dissolved in a mixture of methanol and water and applied to a plug of SCX-silica followed by further elution with aqueous methanol. This was then followed by elution with 1M ammonia in methanol (×4) and these fractions collected and solvent evaporated to dryness leaving a white solid. This was triturated with Et$_2$O and filtered leaving the subtitle compound as a white solid. Yield: 5.0 g.

$^1$H NMR $\delta_{(DMSO)}$ 6.75 (2H, s), 2.90 (4H, m), 2.40 (4H, m), 2.20 (3H, s).

ii) 2-[(3-Chloro-2-fluorobenzyl)thio]-4,6-pyrimidinediol

To a slurry of 2-mercapto-4,6-pyrimidinediol (64.6 g) in ethanol (387 ml) and H$_2$O (387 ml) was added sodium hydroxide (18 g) in H₂O (82 ml) Causing almost a complete solution to form. 2-Fluoro-3-chloro-benzylbromide (100 g) in ethanol (82 ml) was then added dropwise over 30 min causing a thick precipitate to form. Stirring was continued for a further 4 h and the whole then cooled to 0° C. before filtering the white solid formed and then washing with water. The collected solid was dried in vacuo at 50° C. for 48 h leaving the subtitle compound as a white solid. Yield: 125.7 g.

MS APCI(+ve) 287 [M+H]⁺ iii) 4,6-Dichloro-2-[(3-chloro-2-fluorobenzyl)thio]-pyrimidine

The subtitle product from step (125.67 g) was added slowly to phosphorus oxychloride (1 L) over 10 min with stirring. After the addition was complete, N,N-dimethylaniline (92 ml) was added portionwise with care over 10 min causing a complete solution to form. This was then stirred at 120° C. for 15 h. The cooled reaction mixture was then poured onto crushed ice and extracted with EtOAc (×3). The organic phases were combined, dried (MgSO₄) and the solvent evaporated leaving a brown oil which was purified by column chromatography (2% EtOAc/iso-hexane) to afford the subtitle compound as a white solid. Yield: 113 g.

$^1$H NMR $\delta_{(CDCl_3)}$ 7.41 (1H, m), 7.30 (1H, m), 7.0 (2H, m+s), 4.40 (2H, s).

iv) N-[6-Chloro-2-[(3-chloro-2-fluorobenzyl)thio]-4-pyrimidinyl]-4-methyl-1-piperazinesulfonamide To a solution of the subtitle product of step i) (2.0 g) in dry DMF (20 ml) at 0° C. was added 60% sodium hydride (0.9 g) portionwise over 5 min. After further stirring at 0° C. for 30 min the subtitle product from step (3.6 g) in DMF (10 ml) was added and the whole allowed to stir at room temperature for 24 h. The reaction mixture was carefully quenched with aqueous 2M hydrochloric acid until pH 7.4. The solvent was evaporated to dryness and the residue dissolved in a mixture of methanol/EtOAc and applied to an SCX column followed by further elution with EtOAc. This was then followed by elution with EtOAc/triethylamine mixtures and these fractions evaporated to dryness. The subtitle compound was obtained pure by trituration with Et₂O and filtration, leaving a white solid. Yield: 1.5 g.

MS APCI(+ve) 467 [M+H]⁺

EXAMPLE 36

N-[2-[(3-Chloro-2-fluorobenzyl)thio]-6-[(2-hydroxy-1-methylethyl)amino]-4-pyrimidinyl]-4-morpholine-sulfonamide

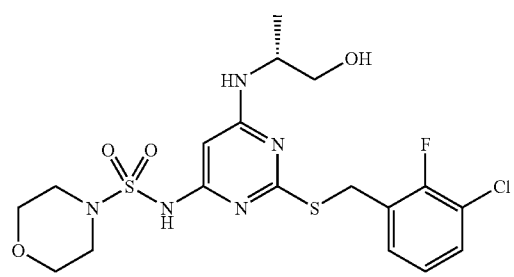

The title compound was prepared from the product of step (1.0 g) and (R)-alaninol (5 ml) according to the procedure used in Example 35 as a white solid. Yield: 0.68 g.

MS APCI(+ve) 493 [M+H]⁺

$^1$H NMR $\delta_{(DMSO)}$ 10.60 (1H, bs), 7.60 (1H, m), 7.50 (1H, m), 7.30 (1H, bs), 7.19 (1H, m), 5.90 (1H, s), 4.70 (1H, m), 4.20 (2H, s), 4.0 (1H, m), 3.80 (4H, m), 3.40 (2H, m), 3.10 (4H, m), 1.10 (3H, d).

The intermediates for this compound were prepared as follows i) 4-Morpholinesulfonamide Morpholine (5 ml) and sulfamide (11 g) in 1,4-dioxane (100 ml) were heated at reflux for 48 h. The solvent was evaporated under reduced pressure and the resulting solid partitioned between EtOAc and water. The organic phase was collected and the aqueous phase was further extracted with EtOAc (×4). The combined organic extracts were dried (MgSO₄) and the solvent removed in vacuo. The solid residue was triturated with Et₂O and filtered to give the subtitle compound as a white crystallin solid. Yield: 2.1 g.

$^1$H NMR $\delta_{(DMSO)}$ 6.82 (2H, s), 3.66 (4H, m), 2.90 (4H, m).

ii) N-[6-chloro-2-[(3-chloro-2-fluorobenzyl)thio]-4-pyrimidinyl]-4-morpholinesulfonamide To a solution of the product of step i) (2.1 g) in dry DMF (20 ml) at 0° C. under nitrogen was added 60% sodium hydride (1.1 g) portionwise over 5 min. After further stirring at 0° C. for 30 min the product from Example 31 step iii) (4 g) in DMF (10 ml) was added and the whole allowed to further stir at room temperature for 24 h. The reaction mixture was carefully quenched with aqueous 2M hydrochloric acid until pH 7.4. The solvent was evaporated to dryness and the residue partitioned between EtOAc and brine. The organic phase was collected, dried (MgSO₄) and the solvent removed in vacuo to afford the subtitle compound as a gummy solid. Yield: 1.3 g.

MS APCI(+ve) 454 [M+H]⁺

EXAMPLE 37

N-[2-[[(3-Chloro-2-fluorophenyl)methyl]thio]-6-[(2-hydroxy-1-methylethyl)amino]-4-pyrimidinyl]-1,2-dimethyl-1H-imidazole-4-sulfonamide

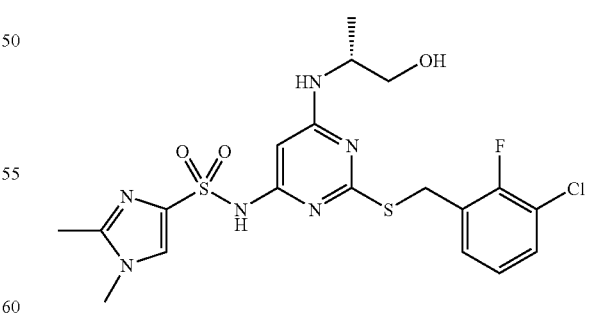

To a solution of the product from Example 27 step iii) (1.3 g) in dry pyridine (10 ml) and 4-N,N-dimethylaminopyridine (0.48 g) under nitrogen was added 1,2-dimethyl-1H-imidazole-4-sulfonyl chloride (1.0 g). The reaction mixture was heated at 55° C. for 5 days. The cooled reaction mixture was partitioned between EtOAc and 1M hydrochloric acid. The organic phases were collected, dried (MgSO₄) and the solvent evaporated to dryness. The resulting gum was dissolved in acetonitrile (15 ml) and treated with 2M hydrochloric acid (5 ml) and the whole stirred at room temperature for 15 min. The reaction mixture was evaporated to dryness leaving a gummy residue. Purification by column chromatography (DCM/methanol/acetic acid 190:10:1) afforded the title compound as a white solid. Yield: 1.0 g.

MS APCI(+ve) 501 [M+H]⁺

¹H NMR $\delta_{(DMSO)}$ 7.85 (1H, bs), 7.50 (2H, m), 7.18 (1H, m), 5.91 (1H, m), 4.36 (2H, s), 3.60 (3H, s), 3.30 (2H, m), 2.30 (3H, s), 1.10 (3H, d).

EXAMPLE 38

N-(2-[(2,3-Difluorobenzyl)thio]-6-{[(1R)-2-hydroxy-1-methylethyl]amino}-pyrimidin-4-yl)piperazine-1-sulfonamide

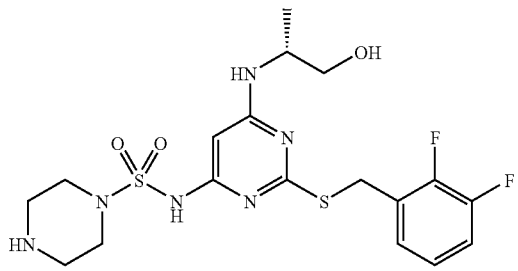

The subtitle product of step i) (2.0 g) was diluted in DCM/trifluoroacetic acid (10:1) for 1 h before concentrating in vacuo and purifying the crude product by reverse phase HPLC (acetonitrile/0.02M ammonium hydroxide (90% to 5% aqueous phase)) to yield the title compound as a white solid. Yield: 6 mg.

MS: APCI(+ve) 475 [M+H]⁺

¹H NMR $\delta_{(DMSO)}$ 7.41 (1H, m), 7.31 (1H, m), 7.14 (1H, m), 5.87 (1H, s), 4.70 (1H, t), 4.38 (2H, s), 3.93 (1H, br. s), 3.44-3.26 (4H, m), 2.81-2.67 (5H, m), 2.42 (1H, m), 1.05 (3H, d).

The intermediates for the above compound were prepared as follows:

i) Piperazine-1-sulfonamide-4,6-dichloro-2-[(3-chloro-2-fluorobenzyl)thio]-pyrimidine 60% Sodium hydride (0.26 g) was added to a solution of the subtitle product of Example 31 step i) (3.11 g) in DMF (10 ml) at 0° C. The reaction was removed from the cooling bath and stirred for 1 h before adding the subtitle product of Example 39 step ii) (5.0 g) as a solution in DMF (5 ml). The reaction was stirred overnight before concentrating in vacuo. The residue was partitioned between H₂O (50 ml) and EtOAc (50 ml) and the organics recovered, dried (MgSO₄) and concentrated in vacuo. The crude product was purified by flash column chromatography (20%, 25% then 30% EtOAc/isohexane) to yield the intermediate as a white solid. This material was diluted in (R)-alaninol (12 ml) and heated at 80° C. for 72 h. The residue was partitioned between H₂O (50 ml) and EtOAc (50 ml) and the organics recovered, dried (MgSO₄) and concentrated in vacuo to afford the subtitle compound as a white solid. Yield: 2.0 g.

¹H NMR $\delta_{(DMSO)}$ 7.15-6.93 (3H, m), 6.20 (1H, s), 5.00 (1H, d), 4.29 (2H, s), 3.71 (1H, dd), 3.57 (1H, dd), 3.42 (4H, t), 3.20 (4H, t), 1.46 (9H, s), 1.21 (3H, d).

EXAMPLE 39

N-(2-[(2,3-Difluorobenzyl)thio]-6-{[(1R)-2-hydroxy-1-methylethyl]amino}pyrimidin-4-yl)azetidine-1-sulfonamide

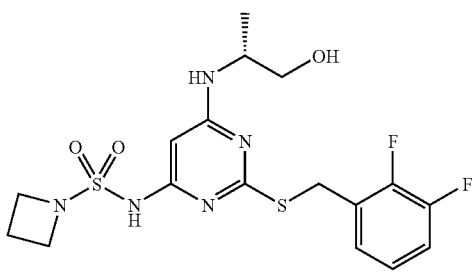

A solution of the subtitle product of step (0.5 g) in (R)-alaninol (1.2 ml) was heated at 80° C. for 18 h before partitioning between EtOAc and H₂O. The organics were recovered, dried (MgSO₄) and concentrated. The residue was purified by column chromatography (1:90:109 AcOH/EtOAc/iso-hexane) before treating the crude material with trifluoroacetic acid (2 ml) and stirring for 12 min then quenching the reaction by the addition of 1M sodium hydroxide solution to pH>10. Saturated ammonium chloride solution was then added to pH 4 and the organics recovered by extracting with EtOAc (3×20 ml). The organics were dried (MgSO₄) and concentrated in vacuo. The crude material was purified by reverse phase HPLC (95% to 20% 0.02M ammonium hydroxide/acetonitrile) to yield the title compound as a white solid. Yield: 90 mg.

MS APCI(+ve) 446 [M+H]⁺

¹H NMR $\delta_{(CDCl3)}$ 7.24-7.21 (1H, m), 7.08-6.97 (2H, m), 6.01 (1H, s), 5.06-4.95 (1H, m), 4.35 (2H, s), 4.20-4.05 (1H, m), 3.98 (4H, t), 3.74-3.70 (1H, m), 3.60-3.56 (1H, m), 2.23 (2H, quin.), 1.22 (3H, d).

The intermediates for this compound were prepared as follows:

i) 2-[(2,3-Difluorobenzyl)thio]pyrimidine-4,6-diol

A solution of potassium hydroxide (5.67 g) was added dropwise to a suspension of 2-mercaptopyrimidine-4,6-diol (14.56 g) in DMF (78 ml) and H₂O (39 ml) and the mixture stirred for 30 min. A solution of 2,3-difluorobenzyl bromide (20.86 g) in THF (16 ml) was then added dropwise and the mixture stirred for 18 h. The reaction was then cooled to 0° C. and the precipitate was filtered and washed with H₂O (4×100 ml) before drying in vacuo to afford the subtitle compound as a cream solid. Yield: 22.4 g.

¹H NMR $\delta_{(DMSO)}$ 7.74 (1H, s), 7.39-7.32 (2H, m), 7.21-7.15 (1H, m), 4.48 (2H, s).

ii) 4,6-Dichloro-2-[(2,3-difluorobenzyl)thio]pyrimidine

N,N-Dimethylaniline (10.3 ml) was added to a slurry of the subtitle product of step i) (10.0 g) in phosphorus oxychloride (55 ml) and the solution heated at reflux for 10 h. The reaction was allowed to cool and excess phosphorus oxychloride was removed in vacuo before partitioning between Et$_2$O (110 ml) and H$_2$O (275 ml) and stirring for 1 h. The layers were separated and the organics concentrated in vacuo to afford the crude product. This crude product was purified by column chromatography (4% EtOAc/iso-hexane) to yield the subtitle compound as a white solid. Yield: 9.10 g.

$^1$H NMR δ$_{(DMSO)}$ 7.74 (1H, s), 7.39-7.32 (2H, m), 7.21-7.15 (1H, m) 4.48 (2H, s).

iii) N-{6-Chloro-2-[(2,3-difluorobenzyl)thio]pyrimidin-4-yl}-N-{[2-(trimethylsilyl)ethoxy]methyl}azetidine-1-sulfonamide To a solution of the product of Example 40 step i) (0.33 g) in dry DMF (4 ml) at 0° C. under nitrogen was added 60% sodium hydride (0.20 g). The reaction was allowed to warm outside the cooling bath for 15 min before recooling to 0° C. and addition of the product from step (0.75 g) in DMF (2 ml) and the whole allowed to further stir at room temperature for 3 h. The reaction was quenched with 2-(trimethylsilyl)ethoxymethyl chloride (0.86 ml) and allowed to stir for 18 h before removal of the volatiles in vacuo and partitioning of the residue between EtOAc (100 ml) and H$_2$O (200 ml). The aqueous was washed further with EtOAc (2×100 ml) and the organics combined, dried (MgSO$_4$) and concentrated in vacuo. The residue was purified by column chromatography (1:22:177 AcOH/EtOAc/iso-hexane) to afford the subtitle compound as a colourless oil. Yield: 0.65 g.

$^1$H NMR δ$_{(CDCl3)}$ 7.34-7.30 (1H, m), 7.19 (1H, s), 7.13-7.02 (2H, m), 5.42 (2H, s), 4.45 (2H, s), 4.06 (4H, t), 3.65 (2H, t), 2.27 (2 h, quin.), 0.93 (2H, t), 0.00 (9H, s).

EXAMPLE 40

N-(2-[(3-Chloro-2-fluorobenzyl)thio]-6-{[(1R)-2-hydroxy-1-methylethyl]amino}-pyrimidin-4-yl)azetidine-1-sulfonamide

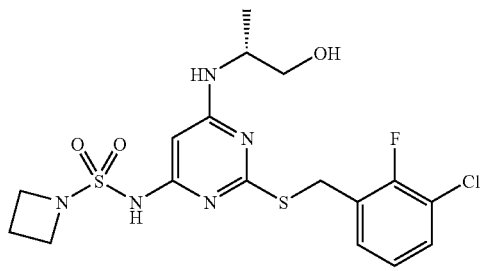

A solution of the subtitle product of step vi) (0.5 g) in trifluoroacetic acid (5 ml) was stirred for 15 min before the addition of 2M sodium hydroxide solution until pH>10. The aqueous was then extracted with Et$_2$O (20 ml) before acidifying the aqueous to pH 4 with 2M hydrochloric acid and extracting with EtOAc (2×20 ml). The EtOAc extracts were combined, dried (MgSO$_4$) and concentrated. The crude material was purified by reverse phase HPLC (90% to 5% 0.02M ammonium hydroxide/acetonitrile) to yield the title compound as a white solid. Yield: 10 mg.

MS APCI(+ve) 462 [M+H]$^+$ $^1$H NMR δ$_{(DMSO)}$ 7.59 (1H, t), 7.46 (1H, t), 7.15 (1H, t), 5.90 (1H, s), 4.69 (1H, t), 4.37 (2H, s), 3.95 (1H, br, s), 3.81 (4H, m), 3.44-3.21 (2H, m), 2.12 (2H, m), 1.05 (3H, d).

The intermediates for this compound were prepared as follows:

i) Azetidine-4-sulfonamide

Azetidine (4.23 g) was added to a solution of sulfamide (7.48 g) in 1,4-dioxan (120 ml) and heated at reflux for 24 h. The volatiles were removed under reduced pressure and the residue suspended in refluxing CHCl$_3$ (500 ml) for 10 min before decanting. The residue was again suspended in hot CHCl$_3$ (500 ml) for 10 min before decanting. The filtrates were combined and concentrated in vacuo to afford the subtitle product as a white solid. Yield: 4.1 g. $^1$H NMR δ$_{(DMSO)}$ 6.91 (2H, s), 3.74 (4H, t), 2.15 (2H, quin.).

ii) N-[2-(Benzylthio)-6-chloropyrimidin-4-yl]-N-{[2-(trimethylsilyl)ethoxy]methyl}-azetidine-1-sulfonamide The subtitle compound was prepared as a yellow oil by the method of Example 32 step i) by reacting the subtitle product of step i) (4.6 g) with the subtitle product of Example 19 step ii) (12.9). Yield: 12.9 g.

MS APCI(+ve) 537 [M+H]$^+$ iii) N-(2-(Benzylthio)-6-{[(1R)-2-hydroxy-1-methylethyl]amino}pyrimidin-4-yl)-N-{[2-(trimethylsilyl)ethoxy]methyl}azetidine-1-sulfonamide The subtitle compound was prepared as a yellow oil by the method of Example 32 step by reacting the subtitle product of step (12.2 g) with (R)-alaninol (18 ml). Yield: 11.3 g.

MS APCI(+ve) 540 [M+H]$^+$ iv) N-(2-(Benzylsulfonyl)-6-{[(1R)-2-hydroxy-1-methylethyl]amino}pyrimidin-4-yl)-N-{[2-(trimethylsilyl)ethoxy]methyl}azetidine-1-sulfonamide m-Chloroperbenzoic acid was added as a single portion to a solution of the subtitle product of step iii) (11.3 g) in DCM (500 ml) and stirred for 1 h. Saturated sodium thiosulfate solution (100 ml) was added and stirred vigorously until no peroxide was detected. The organics were separated and extracted with saturated sodium bicarbonate solution (200 ml) and brine (50 ml), dried (MgSO$_4$) and concentrated to yield the subtitle compound as a crude solid. Yield: 10.9 g.

MS APCI(+ve) 572 [M+H]$^+$ v) Sodium 4-((azetidin-1-ylsulfonyl){[2-(trimethylsilyl)ethoxy]methyl}amino)-6-{[(1R)-2-hydroxy-1-methylethyl]amino}pyrimidine-2-thiolate Sodium hydrosulfide hydrate (1.18 g) was added to a solution of the subtitle product of step iv) (8.0 g) in DMSO (67 ml) and the green solution stirred for 2 h. A further aliquot of sodium hydrosulfide hydrate (0.79 g) was added and stirred for 1 h. This aliquot addition was repeated twice more before heating the solution at 50° C. for 30 min. The resulting reaction solution was used directly in the following step. The subtitle compound was also kept as a stock solution for further reaction with alkyl halides, described in Examples 41-42.

MS APCI(+ve) 450 [M+H]$^+$ vi) N-(2-[(3-Chloro-2-fluorobenzyl)thio]-6-{[(1R)-2-hydroxy-1-methylethyl]amino}-pyrimidin-4-yl)-N-{[2-(trimethylsilyl)ethoxy]methyl}azetidine-1-sulfonamide 3-Chloro-2-fluorobenzyl bromide (3.13 g) was added to an aliquot of the reaction solution of step v) (18 ml) containing the subtitle product of step v) and the reaction stirred for 1 h. The reaction was partitioned between EtOAc (20 ml) and H$_2$O (20 ml) and the organics concentrated in vacuo. The residue was purified by column chromatography (20% then 40% EtOAc/iso-hexane) to afford the subtitle compound as an oil which was used directly in the subsequent step.

MS APCI(+ve) 592 [M+H]$^+$

EXAMPLE 41

N-{6-{[(1R)-2-Hydroxy-1-methylethyl]amino}-2-[(2,3,4-trifluorobenzyl)thio]-pyrimidin-4-yl}azetidine-1-sulfonamide

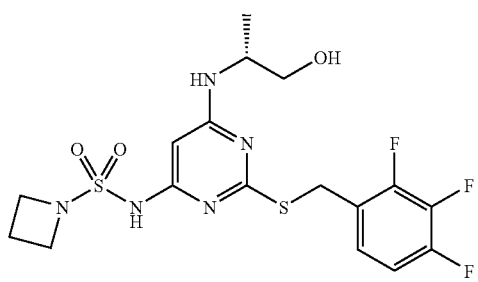

A solution of the subtitle product of step i) in trifluoroacetic acid (5 ml) was stirred for 15 min before the addition of 2M sodium hydroxide solution until pH>10. The aqueous was then extracted with Et$_2$O (20 ml) followed by EtOAc (2×20 ml). The EtOAc extracts were combined, dried (MgSO$_4$) and concentrated. The crude material was purified by reverse phase HPLC (90% to 5% 0.02M ammonium hydroxide/acetonitrile) to yield the title compound as a white solid. Yield: 51 mg.

MS APCI(+ve) 464 [M+H]$^+$ $^1$H NMR $\delta_{(DMSO)}$ 10.50 (1H, br. s), 7.47 (1H, m), 7.25 (2H, m), 5.94 (1H, m), 4.70 (1H, br, s), 4.36 (2H, s), 4.04 (1H, br, s), 3.86 (4H, m), 3.40±3.25 (2H, m), 2.10 (2H, m), 1.05 (3H, d).

The intermediates for this compound were prepared as follows:

i) N-{6-{[(1R)-2-Hydroxy-1-methylethyl]amino}-2-[(2,3,4-trifluorobenzyl)thio]-pyrimidin-4-yl}-N-{[2-(trimethylsilyl)ethoxy]methyl}azetidine-1-sulfonamide 2,3,4-Trifluorobenzyl bromide (3.15 g) was added to an aliquot of the reaction solution of step v) (18 ml) containing the subtitle product of step v) and the reaction stirred for 1 h. The reaction was partitioned between EtOAc (20 ml) and H$_2$O (20 ml) and the organics concentrated in vacuo. The residue was purified by column chromatography (20% then 40% EtOAc/iso-hexane) to afford the subtitle compound as an oil which was used directly in the subsequent step.

MS APCI(+ve) 594 [M+H]$^+$

EXAMPLE 42

N-(2-[(2,3-Difluoro-4-methylbenzyl)thio]-6-{[(1R)-2-hydroxy-1-methylethyl]amino}-pyrimidin-4-yl)azetidine-1-sulfonamide

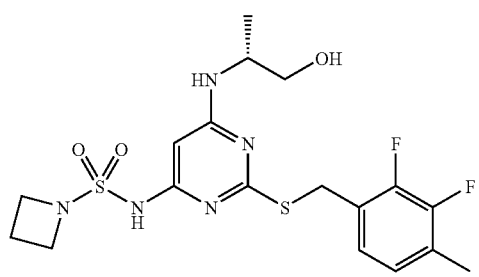

A solution of the subtitle product of step i) in trifluoroacetic acid (5 ml) was stirred for 15 min before the addition of 2M sodium hydroxide solution until pH>10. The aqueous was then extracted with Et$_2$O (20 ml) followed by EtOAc (2×20 ml). The EtOAc extracts were combined, dried (MgSO$_4$) and concentrated. The crude material was purified by reverse phase HPLC (90% to 5% 0.02M ammonium hydroxide/acetonitrile) to yield the title compound as a white solid. Yield: 42 mg.

MS APCI(+ve) 460 [M+H]$^+$ $^1$H NMR $\delta_{(DMSO)}$ 7.29 (1H, t), 7.02 (1H, t), 5.93 (1H, s), 4.70 (1H, t), 4.34 (2H, s), 4.05 (1H, br, s), 3.85 (4H, m), 3.41 (1H, m), 3.28 (1H, m), 2.25 (3H, s), 2.10 (2H, quin.), 1.06 (3H, d).

The intermediates for this compound were prepared as follows:

i) N-(2-[(2,3-Difluoro-4-methylbenzyl)thio]-6-{[(1R)-2-hydroxy-1-methylethyl]amino}-pyrimidin-4-yl)-N-{[2-(trimethylsilyl)ethoxy]methyl}azetidine-1-sulfonamide 2,3-Difluoro-4-methylbenzyl bromide (3.10 g) was added to an aliquot of the reaction solution of step v) (18 ml) containing the subtitle product of step v) and the reaction stirred for 1 h. The reaction was partitioned between EtOAc (20 ml) and H$_2$O (20 ml) and the organics concentrated in vacuo. The residue was purified by column chromatography (20% then 40% EtOAc/iso-hexane) to afford the subtitle compound as an oil which was used directly in the subsequent step.

MS APCI(+ve) 590 [M+H]$^+$

EXAMPLE 43

N-(2-[(2-Fluorobenzyl)thio]-6-{[(1R)-2-hydroxy-1-methylethyl]amino}pyrimidin-4-yl)methanesulfonamide

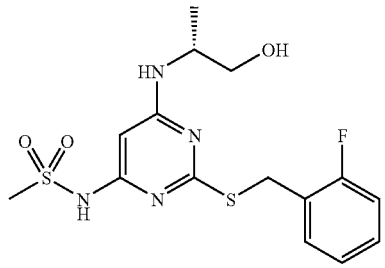

The title product was prepared from a solution of the product of step iv) (4 ml) and quenching with 2-fluorobenzyl bromide (0.5 g) at room temperature. After 30 min the reaction mixture was partitioned between EtOAc (20 ml) and saturated brine (20 ml). The organic layer was collected and the solvent evaporated to dryness. The residue was passed through a pad of silica gel (1:1 EtOAc/iso-hexane) to give the intermediate product as a gum. This was dissolved in acetonitrile (10 ml) and treated with 1M hydrochloric acid with stirring at ambient temperature over 24 h. The volatiles were removed in vacuo and the residue purified by mass directed reverse phase HPLC to give the title compound as a white foam. Yield: 5 mg.

MS APCI(+ve) 387 [M+H]+

The intermediates for this compound were prepared as follows:

i) N-[2-(benzylthio)-6-chloropyrimidin-4-yl]-N-{[2-(trimethylsilyl)ethoxy]methyl}-methanesulfonamide To a solution of methanesulfonamide (4.63 g) in dry DMF (60 ml) at 0° C. under nitrogen was added 60% sodium hydride (3.9 g) portionwise over 5 min. After complete addition the ice bath was removed for 15 min and then returned. A solution of the subtitle product of Example 19 step ii) in DMF (30 ml) was added dropwise over 5 min. After complete addition the ice bath was removed and the whole stirred at ambient temperature for 3 h. The ice bath was returned before adding trimethylsilylethoxymethyl chloride (8.6 ml) to the reaction mixture. The reaction mixture was allowed to reach ambient temperature and further stirred for 24 h. The reaction mixture was partitioned between EtOAc and H₂O. The organic phase collected, dried (MgSO₄) and solvent removed in vacuo to leave the subtitle compound as a pale yellow oil. Yield: 21.2 g.

MS APCI(+ve) 460 [M+H]+ ii) N-(2-(Benzylthio)-6-{[(1R)-2-hydroxy-1-methylethyl]amino}pyrimidin-4-yl)-N-{[2-(trimethylsilyl)ethoxy]methyl}methanesulfonamide To a solution of the product of step i) (21.2 g) in NM (40 ml) was added (R)-alaninol (10 g) and the whole heated at 80° C. for 4 h. The reaction mixture was then partitioned between EtOAc and H₂O. The organic phase was collected, dried (MgSO₄) and the solvent removed to leave a pale yellow oil. This was purified by silica gel chromatography (60:40 iso-hexane/EtOAc) to afford the subtitle compound as a colourless oil. Yield: 13.9 g.

MS APCI(+ve) 499 [M+H]+ iii) N-(2-(Benzylsulfonyl)-6-{[(1R)-2-hydroxy-1-methylethyl]amino}pyrimidin-4-yl)-N-{[2-(trimethylsilyl)ethoxy]methyl}methanesulfonamide To a solution of the product of step ii) (6.8 g) in DCM (300 ml) was added m-chloroperbenzoic acid (8 g) at ambient temperature with stirring. After 6 h a concentrated solution of sodium thiosulphate (50 ml) was added and the organic phase collected. The organic phase was then washed with saturated sodium bicarbonate solution (×2) followed by brine. The organic phase was dried (MgSO₄) and the solvent evaporated to leave the subtitle compound as a colourless foam. Yield: 7.0 g.

MS APCI(+ve) 531 [M+H]+, MS APCI(−ve) 529 [M−H]+ iv) Sodium 4-{[(1R)-2-hydroxy-1-methylethyl]amino}-6-((methylsulfonyl){[2-(trimethylsilyl)ethoxy]methyl}amino)pyrimidine-2-thiolate To a solution of the product of step iii) (3.97 g) in DMSO (30 ml) was added sodium hydrosulphide hydrate (0.84 g). Stirring was continued for a further 2 h and additional aliquots of 0.42 g of sodium hydrosulphide were added until complete disappearance of starting material as assessed by reverse phase HPLC-MS. The subtitle compound was also kept as a stock solution for further reaction with alkyl halides described in examples 43-53 and 137.

MS APCI(−ve) 407 [M−H]+

EXAMPLE 44

N-(2-[(2,5-Difluorobenzyl)thio]-6-{[(1R)-2-hydroxy-1-methylethyl]amino}pyrimidin-4-yl)methanesulfonamide

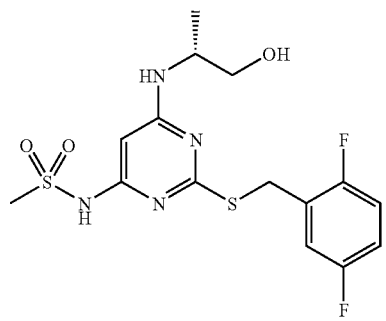

The title compound was prepared from a solution of the product of Example 43 step iv) (4 ml) and quenching with 2,5-difluorobenzyl bromide (0.5 g) using the method described for Example 43 to give the title compound as a white foam. Yield: 5 mg.

MS APCI(+ve) 405 [M+H]+, MS APCI(−ve) 403 [M−H]+

EXAMPLE 45

N-(2-[(2,4-Difluorobenzyl)thio]-6-{[(1R)-2-hydroxy-1-methylethyl]amino}pyrimidin-4-yl)methanesulfonamide

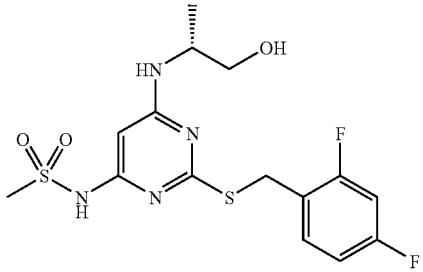

The title compound was prepared from a solution of the product of Example 43 step iv) (4 ml) and quenching with 2,4-difluorobenzyl bromide (0.5 g) using the method described for Example 43 to give the title compound as a white foam. Yield: 12 mg.

MS APCI(+ve) 405 [M+H]⁺, MS APCI(−ve) 403 [M−H]⁺

EXAMPLE 46

N-(2-[(2,6-Difluorobenzyl)thio]-6-{[(1R)-2-hydroxy-1-methylethyl]amino}pyrimidin-4-yl)methanesulfonamide

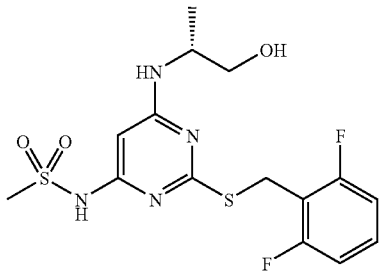

The title compound was prepared from a solution of the product of Example 43 step iv) (4 ml) and quenching with 2,6-difluorobenzyl bromide (0.5 g) using the method described for Example 43 to give the title compound as a white foam. Yield: 10 mg.

MS APCI(+ve) 405 [M+H]⁺, MS APCI(−ve) 403 [M−H]⁺

EXAMPLE 47

N-(2-[(2,3,6-Trifluorobenzyl)thio]-6-{[(1R)-2-hydroxy-1-methylethyl]amino}-pyrimidin-4-yl)methanesulfonamide

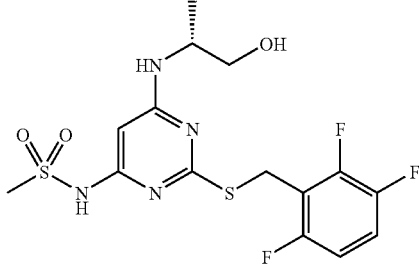

The title compound was prepared from a solution of the product of Example 43 step iv) (4 ml) and quenching with 2,3,6-trifluorobenzyl bromide (0.5 g) using the method described for Example 43 to give the title compound as a white foam. Yield: 14 mg.

MS APCI(+ve) 423 [M+H], MS APCI(−ve) 421 [M−H]⁺

EXAMPLE 48

N-(2-[(5-Chloro-2-fluorobenzyl)thio]-6-{[(1R)-2-hydroxy-1-methylethyl]amino}-pyrimidin-4-yl)methanesulfonamide

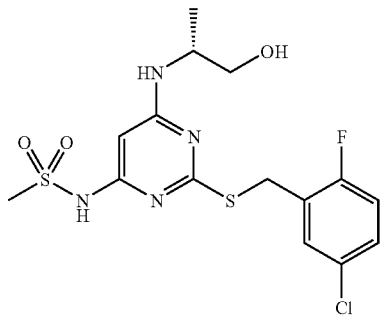

The title compound was prepared from a solution of the product of Example 43 step iv) (4 ml) and quenching with 5-chloro-2-fluorobenzyl bromide (0.5 g) using the method described for Example 43 to give the title compound as a white foam. Yield: 8 mg.

MS APCI(+ve) 421 [M+H]⁺, MS APCI(−ve) 419 [M−H]⁺

EXAMPLE 49

N-{6-{[(1R)-2-Hydroxy-1-methylethyl]amino}-2-[(2,4,5-trifluorobenzyl)thio]-pyrimidin-4-yl}methanesulfonamide

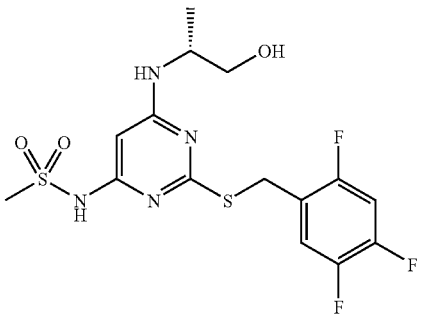

The title compound was prepared from a solution of the product of Example 43 step iv) (4 ml) and quenching with 2,4,5-trifluorobenzyl bromide (0.5 g) using the method described for Example 43 to give the title compound as a white foam. Yield: 7 mg.

MS APCI(+ve) 423 [M+H]⁺, MS APCI(−ve) 421 [M−H]⁺

EXAMPLE 50

N-(2-[(3-Chloro-2,6-difluorobenzyl)thio]-6-{[(1R)-2-hydroxy-1-methyl ethyl]amino}-pyrimidin-4-yl)methanesulfonamide

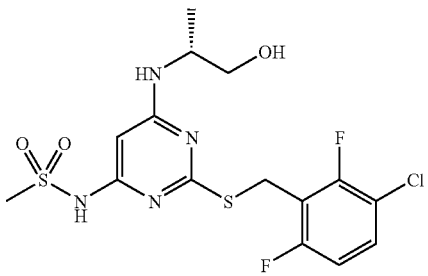

The title compound was prepared from a solution of the product of Example 43 step iv) (4 ml) and quenching with 3-chloro-2,6-difluorobenzyl bromide (0.5 g) using the method described for Example 43 to give the title compound as a white foam. Yield: 27 mg.
MS APCI(+ve) 439 [M+H]$^+$

EXAMPLE 51

N-{6-{[(1R)-2-Hydroxy-1-methylethyl]amino}-2-[(2,4,6-trifluorobenzyl)thio]-pyrimidin-4-yl}methanesulfonamide

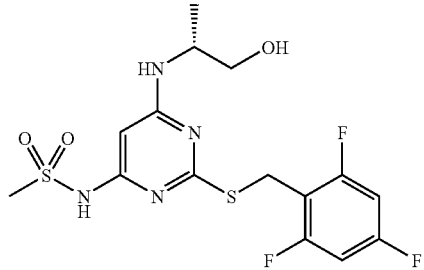

The title compound was prepared from a solution of the product of Example 43 step iv) (4 ml) and quenching with 2,4,6-trifluorobenzyl bromide (0.5 g) using the method described for Example 43 to give the title compound as a white foam. Yield: 42 mg.
MS APCI(+ve) 423 [M+H]$^+$

EXAMPLE 52

N-(2-[(2-Chloro-3,6-difluorobenzyl)thio]-6-{[(1R)-2-hydroxy-1-methylethyl]amino}-pyrimidin-4-yl)methanesulfonamide

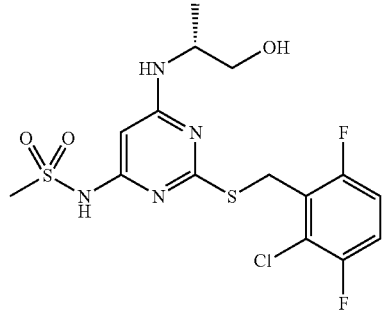

The title compound was prepared from a solution of the product of Example 43 step iv) (4 ml) and quenching with 2-chloro-3,6-difluorobenzyl bromide (0.5 g) using the method described for Example 43 to give the title compound as a white foam. Yield: 40 mg.
MS APCI(+ve) 439 [M+H]$^+$

EXAMPLE 53

N-(2-[(2-Chloro-6-fluorobenzyl)thio]-6-{[(1R)-2-hydroxy-1-methylethyl]amino}-pyrimidin-4-yl)methanesulfonamide

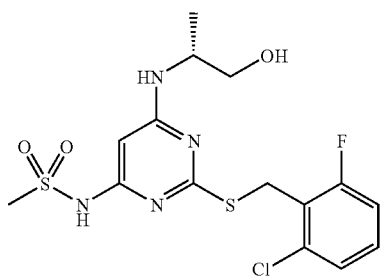

The title compound was prepared from a solution of the product of Example 43 step iv) (4 ml) and quenching with 2-chloro-6-fluorobenzyl bromide (0.5 g) using the method described for Example 43 to give the title compound as a white foam. Yield: 32 mg.
MS APCI(+ve) 421 [M+H]$^+$ General Procedure for the Synthesis of Examples 54 to 99.

To the required sulfonyl chloride (0.15 mM) was added a solution of the subtitle product of Example 3 step ii) (0.05 mM) in pyridine (0.4 ml) and 4-N,N-dimethylaminopyridine (0.05 mM) in pyridine (0.2 ml) before the reaction mixture was stirred at room temperature for three days. 3M Hydrochloric acid (0.2 ml) was added and stirring maintained for 18 h before the solvent was removed under reduced pressure. The residue was dissolved in DMSO/H$_2$O (400 µl; 3:1), filtered through a PORVAIR filter and the product purified by mass directed reverse phase HPLC to afford the title products of Examples 54 to 99.

EXAMPLE 54

N-{2-(Benzylthio)-6-[((1R)-2-hydroxy-1-methylethyl)amino]pyrimidin-4-yl}-4-methylbenzenesulfonamide

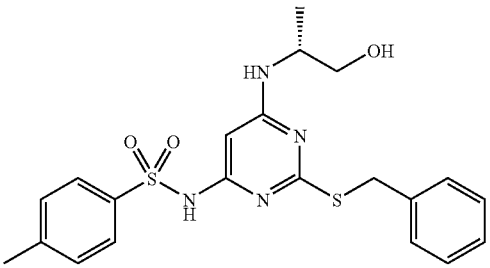

Yield: 7 mg.
MS: APCI (+ve) 369 [M+H]$^+$

EXAMPLE 55

N-{2-(Benzylthio)-6-[((2)-2-hydroxy-1-methylethyl)amino]pyrimidin-4-yl}-2,4,6-trimethylbenzenesulfonamide

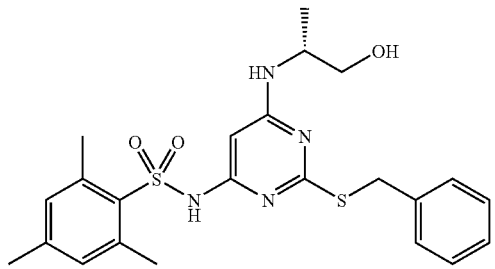

Yield: 11 mg.
MS: APCI (+ve) 473 [M+H]$^+$

EXAMPLE 56

N-{2-(Benzylthio)-6-[((1R)-2-hydroxy-1-methylethyl)amino]pyrimidin-4-yl}naphthalene-2-sulfonamide

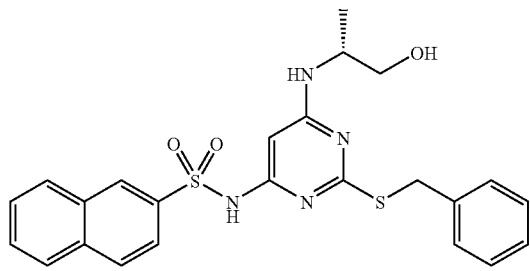

Yield: 14 mg.
MS: APCI (+ve) 481 [M+H]$^+$

EXAMPLE 57

N-(2-(Benzylthio)-6-{[(1R)-2-hydroxy-1-methylethyl]amino}pyrimidin-4-yl)-1-(R,S)-(1,3-dioxo-1,3-dihydro-2H-isoindol-2-yl)ethanesulfonamide

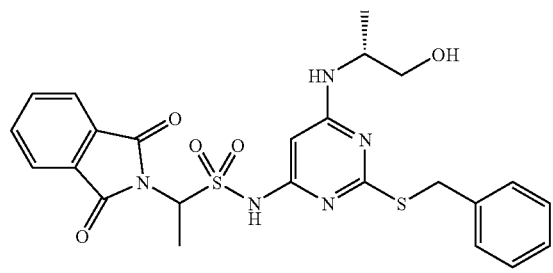

Yield: 4 mg.
MS: APCI (+ve) 528 [M+H]$^+$

EXAMPLE 58

N-{2-(Benzylthio)-6-[((1R)-2-hydroxy-1-methylethyl)amino]pyrimidin-4-yl}-4-bromobenzenesulfonamide

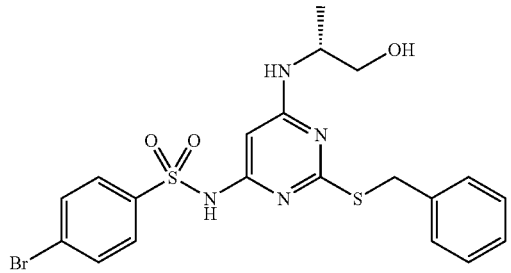

Yield: 7 mg.
MS: APCI (+ve) 509/511 [M+H]$^+$

EXAMPLE 59

N-{2-(Benzylthio)-6-[((1R)-2-hydroxy-1-methylethyl)amino]pyrimidin-4-yl}-4-tert-butylbenzenesulfonamide

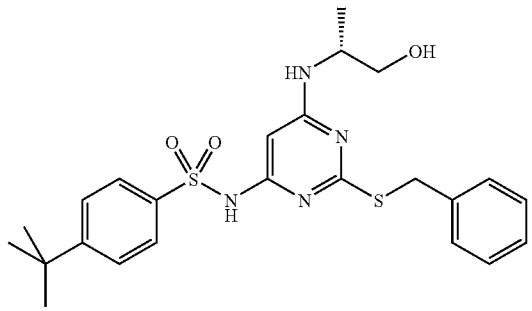

Yield: 14 mg.
MS: APCI (+ve) 487 [M+H]$^+$

EXAMPLE 60

N-{2-(Benzylthio)-6-[((1R)-2-hydroxy-1-methylethyl)amino]pyrimidin-4-yl}-2-bromobenzenesulfonamide

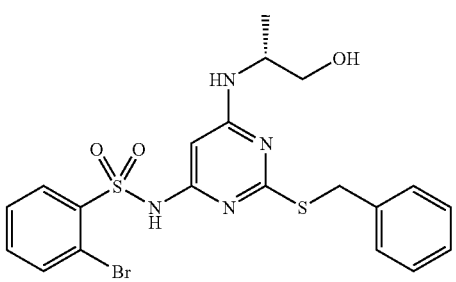

MS: APCI (+ve) 509/511 [M+H]$^+$

EXAMPLE 61

N-{2-(Benzylthio)-6-[((1R)-2-hydroxy-1-methyl-ethyl)amino]pyrimidin-4-yl}-4-(trifluoromethyl)benzenesulfonamide

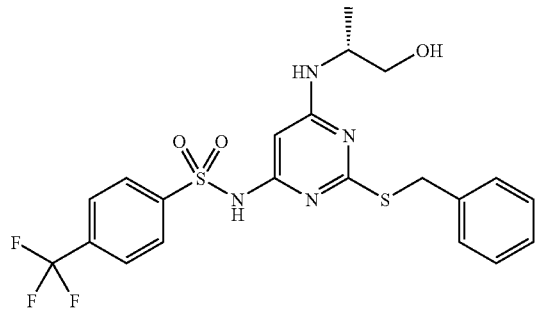

Yield: 14 mg.
MS: APCI (+ve) 499 [M+H]$^+$

EXAMPLE 62

N-{2-(Benzylthio)-6-[((1R)-2-hydroxy-1-methyl-ethyl)amino]pyrimidin-4-yl}-3-(trifluoromethyl)benzenesulfonamide

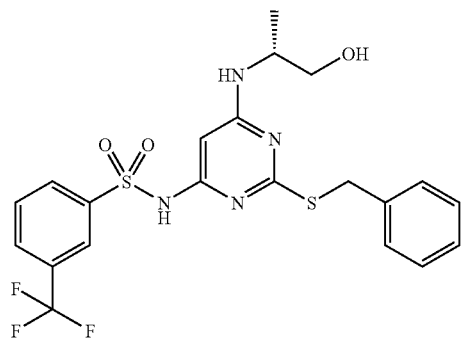

Yield: 9 mg.
MS: APCI (+ve) 499 [M+H]$^+$

EXAMPLE 63

N-{2-(Benzylthio)-6-[((1R)-2-hydroxy-1-methyl-ethyl)amino]pyrimidin-4-yl}-2,5-dimethoxybenzene-sulfonamide

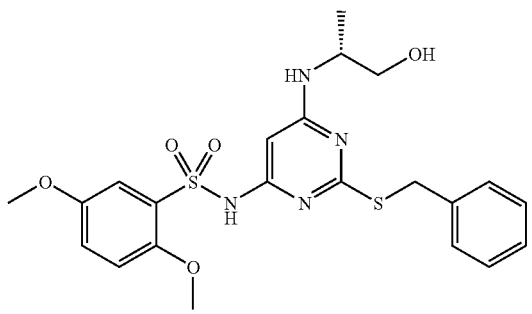

Yield: 13 mg.
MS: APCI (+ve) 491 [M+H]$^+$

EXAMPLE 64

N-{2-(Benzylthio)-6-[((1R)-2-hydroxy-1-methyl-ethyl)amino]pyrimidin-4-yl}-2,1,3-benzoxadiazole-4-sulfonamide

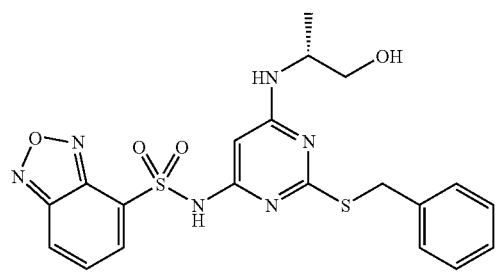

Yield: 4 mg.
MS: APCI (+ve) 473 [M+H]$^+$

EXAMPLE 65

N-{2-(Benzylthio)-6-[((1R)-2-hydroxy-1-methyl-ethyl)amino]pyrimidin-4-yl}-5-isoxazol-3-ylthiophene-2-sulfonamide

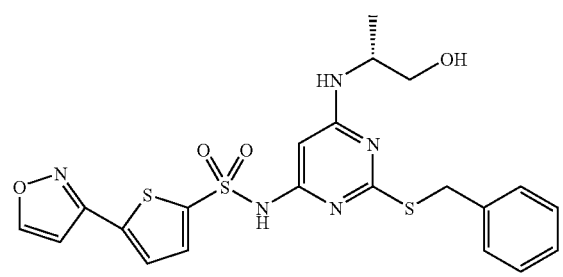

Yield: 8 mg.
MS: APCI (+ve) 504 [M+H]$^+$

EXAMPLE 66

N-{2-(Benzylthio)-6-[((1R)-2-hydroxy-1-methyl-ethyl)amino]pyrimidin-4-yl}-2,6-dichlorobenzene-sulfonamide

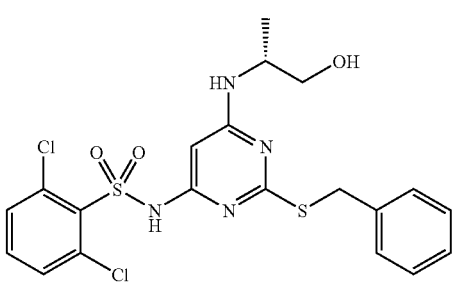

Yield: 10 mg.
MS: APCI (+ve) 499/501/503 [M+H]$^+$

EXAMPLE 67

N-{2-(Benzylthio)-6-[((1R)-2-hydroxy-1-methyl-ethyl)amino]pyrimidin-4-yl}-2,6-difluorobenzene-sulfonamide

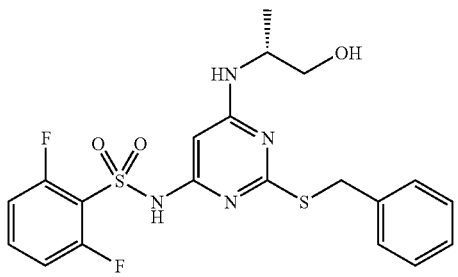

Yield: 7 mg.
MS: APCI (+ve) 467 [M+H]+

EXAMPLE 68

N-{2-(Benzylthio)-6-[((1R)-2-hydroxy-1-methyl-ethyl)amino]pyrimidin-4-yl}-4-(1,1-dimethylpropyl)benzenesulfonamide

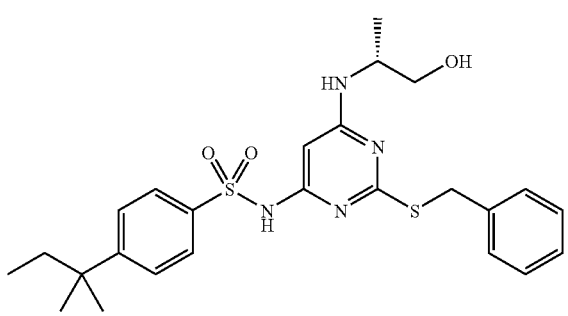

Yield: 13 mg.
MS: APCI (+ve) 501 [M+H]+

EXAMPLE 69

N-{2-(Benzylthio)-6-[((1R)-2-hydroxy-1-methyl-ethyl)amino]pyrimidin-4-yl}-2-chloro-4-fluoroben-zenesulfonamide

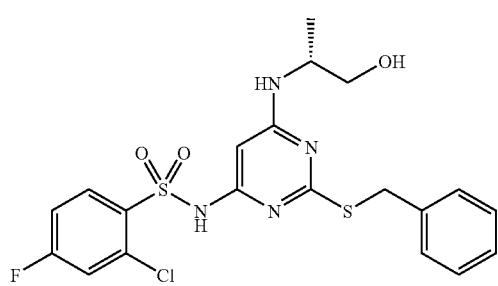

Yield: 9 mg.
MS: APCI (+ve) 483/485 [M+H]+

EXAMPLE 70

N-{2-(Benzylthio)-6-[((1R)-2-hydroxy-1-methyl-ethyl)amino]pyrimidin-4-yl}-3-chloro-4-fluoroben-zenesulfonamide

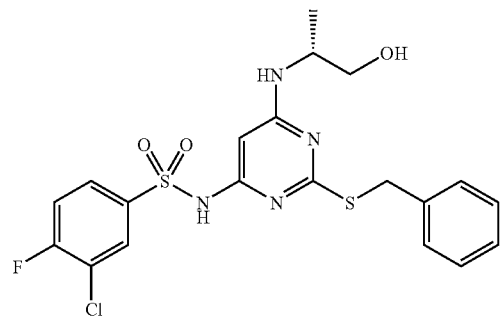

Yield: 15 mg.
MS: APCI (+ve) 483/485 [M+H]+

EXAMPLE 71

N-{2-(Benzylthio)-6-[((1R)-2-hydroxy-1-methyl-ethyl)amino]pyrimidin-4-yl}-2,5-dichlorobenzene-sulfonamide

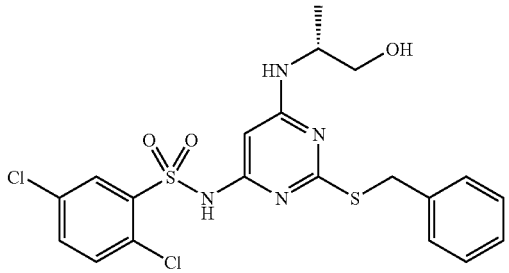

Yield: 11 mg.
MS: APCI (+ve) 499/501/503 [M+H]+

EXAMPLE 72

N-{2-(Benzylthio)-6-[((1R)-2-hydroxy-1-methyl-ethyl)amino]pyrimidin-4-yl}-4-propylbenzene-sulfonamide

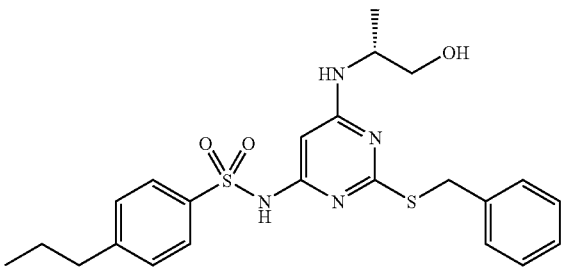

Yield 14 mg
MS: APCI (+ve) 473 [M+H]+.

EXAMPLE 73

N-{2-(Benzylthio)-6-[((1R)-2-hydroxy-1-methyl-ethyl)amino]pyrimidin-4-yl}-3-bromobenzene-sulfonamide

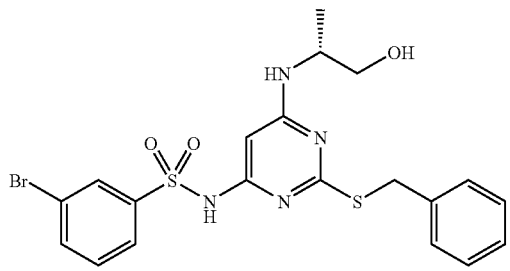

Yield: 17 mg.
MS: APCI (+ve) 509/511 [M+H]$^+$

EXAMPLE 74

N-{2-(Benzylthio)-6-[((1R)-2-hydroxy-1-methyl-ethyl)amino]pyrimidin-4-yl}-3-chloro-2-methylbenzenesulfonamide

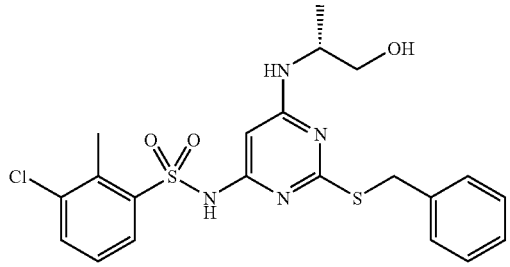

Yield: 13 mg.
MS: APCI (+ve) 479/481 [M+H]$^+$

EXAMPLE 75

N-{2-(Benzylthio)-6-[((1R)-2-hydroxy-1-methyl-ethyl)amino]pyrimidin-4-yl}-2,5-dichlorothiophene-3-sulfonamide

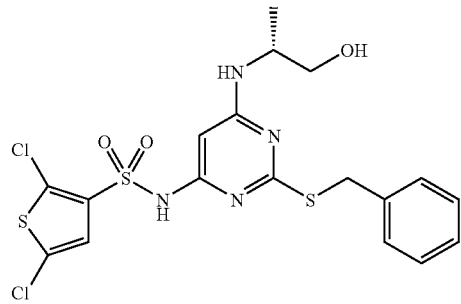

Yield: 6 mg.
MS: APCI (+ve) 505/507/509 [M+H]$^+$

EXAMPLE 76

N-{2-(Benzylthio)-6-[((1R)-2-hydroxy-1-methyl-ethyl)amino]pyrimidin-4-yl}-3,4-dimethoxybenzenesulfonamide

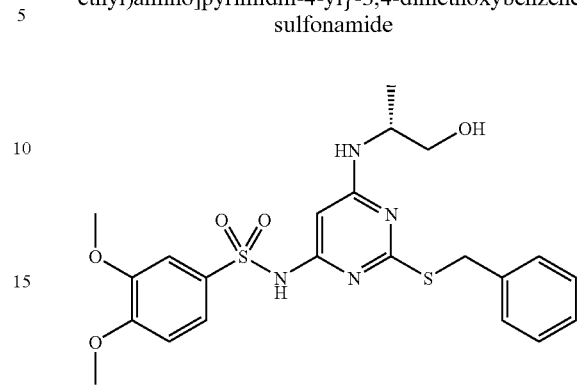

Yield: 11 mg.
MS: APCI (+ve) 491 [M+H]$^+$

EXAMPLE 77

N-{2-(Benzylthio)-6-[((1R)-2-hydroxy-1-methyl-ethyl)amino]pyrimidin-4-yl}-2,3-dichlorobenzenesulfonamide

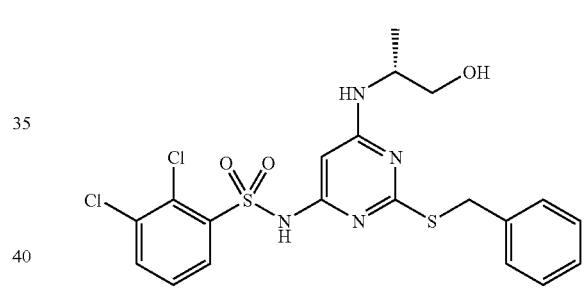

Yield: 11 mg.
MS: APCI (+ve) 499/501/503 [M+H]$^+$

EXAMPLE 78

N-{2-(Benzylthio)-6-[((1R)-2-hydroxy-1-methyl-ethyl)amino]pyrimidin-4-yl}-5-chlorothiophene-2-sulfonamide

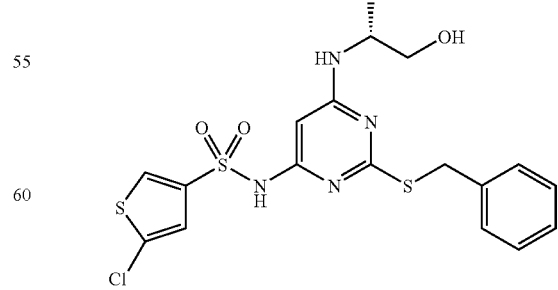

Yield: 8 mg
MS: APCI (+ve) 471/473 [M+H]$^+$.

EXAMPLE 79

N-{2-(Benzylthio)-6-[((1R)-2-hydroxy-1-methyl-ethyl)amino]pyrimidin-4-yl}-2-chloro-6-methylbenzenesulfonamide

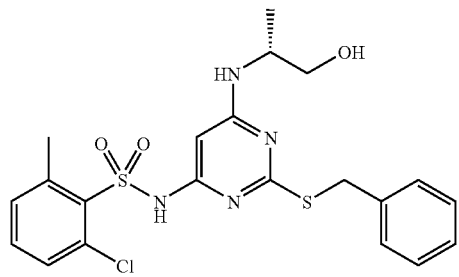

Yield: 7 mg.
MS: APCI (+ve) 479/481 [M+H]$^+$

EXAMPLE 80

N-{2-(Benzylthio)-6-[((1R)-2-hydroxy-1-methyl-ethyl)amino]pyrimidin-4-yl}-3,4-dichlorobenzenesulfonamide

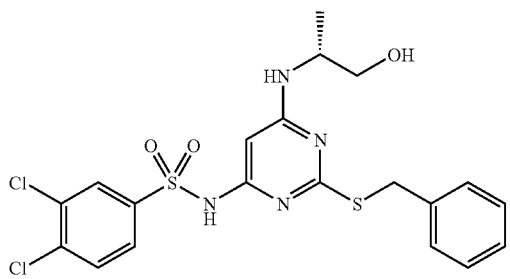

Yield: 13 mg.
MS: APCI (+ve) 499/501/503 [M+H]$^+$

EXAMPLE 81

N-{2-(Benzylthio)-6-[((1R)-2-hydroxy-1-methyl-ethyl)amino]pyrimidin-4-yl}-3,5-dichlorobenzenesulfonamide

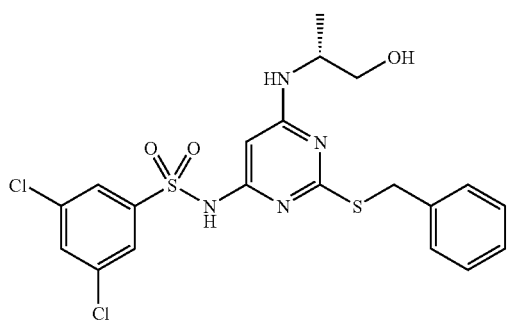

Yield: 14 mg.
MS: APCI (+ve) 499/501/503 [M+H]$^+$

EXAMPLE 82

N-{2-(Benzylthio)-6-[((1R)-2-hydroxy-1-methyl-ethyl)amino]pyrimidin-4-yl}-2,4-dichloro-5-methyl-benzenesulfonamide

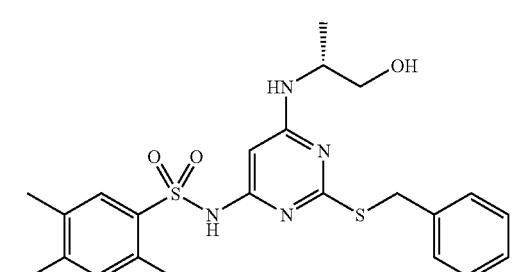

Yield: 12 mg.
MS: APCI (+ve) 513/515/517 [M+H]$^+$

EXAMPLE 83

N-{2-(Benzylthio)-6-[((1R)-2-hydroxy-1-methyl-ethyl)amino]pyrimidin-4-yl}-3,4-difluorobenzenesulfonamide

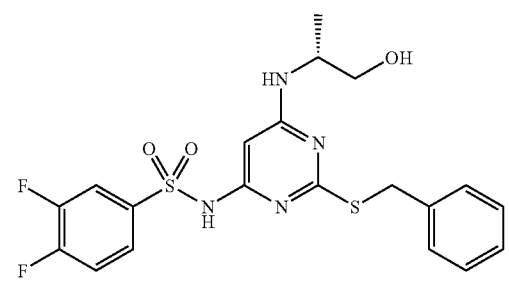

Yield: 15 mg.
MS: APCI (+ve) 467 [M+H]$^+$

EXAMPLE 84

N-{2-(Benzylthio)-6-[((1R)-2-hydroxy-1-methyl-ethyl)amino]pyrimidin-4-yl}-2-methylbenzenesulfonamide

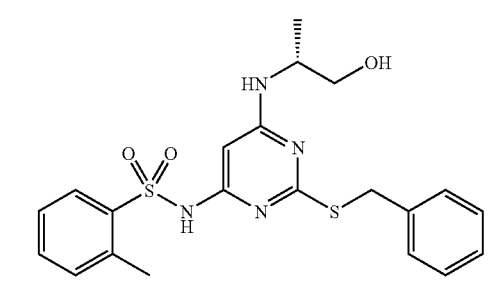

Yield: 14 mg.
MS: APCI (+ve) 445 [M+H]$^+$

EXAMPLE 85

N-{2-(Benzylthio)-6-[((1R)-2-hydroxy-1-methyl-ethyl)amino]pyrimidin-4-yl}-3-methoxybenzene-sulfonamide

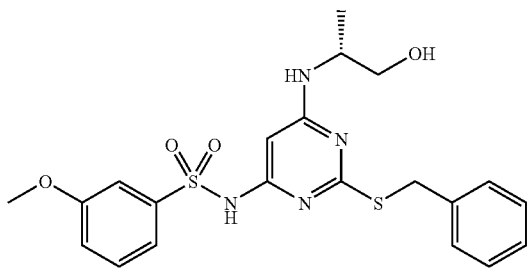

Yield: 16 mg.
MS: APCI (+ve) 461 [M+H]+

EXAMPLE 86

N-{2-(Benzylthio)-6-[((1R)-2-hydroxy-1-methyl-ethyl)amino]pyrimidin-4-yl}-2,5-difluorobenzene-sulfonamide

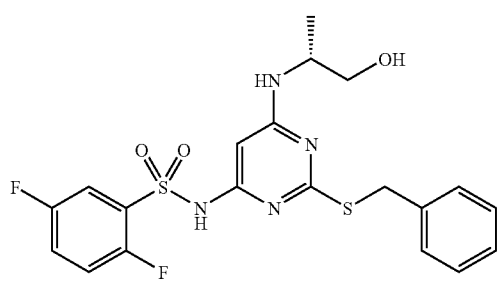

Yield: 12 mg.
MS: APCI (+ve) 467 [M+H]+

EXAMPLE 87

N-{2-(Benzylthio)-6-[((1R)-2-hydroxy-1-methyl-ethyl)amino]pyrimidin-4-yl}-4-chloro-2,5-dimethoxybenzenesulfonamide

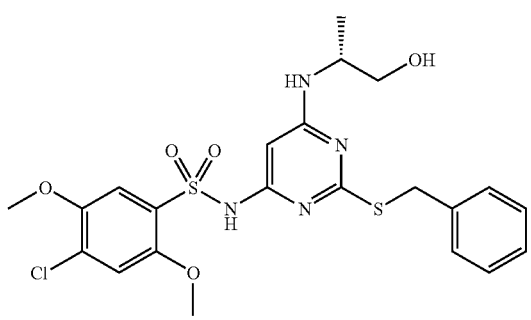

Yield: 9 mg.
MS: APCI (+ve) 525/527 [M+H]+

EXAMPLE 88

N-{2-(Benzylthio)-6-[((1R)-2-hydroxy-1-methyl-ethyl)amino]pyrimidin-4-yl}thiophene-3-sulfonamide

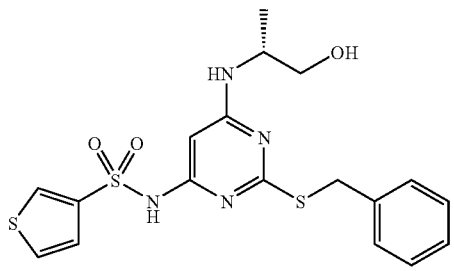

Yield: 18 mg.
MS: APCI (+ve) 437 [M+H]+

EXAMPLE 89

4-Acetyl-N-{2-(benzylthio)-6-[((1R)-2-hydroxy-1-methylethyl)amino]pyrimidin-4-yl}benzenesulfonamide

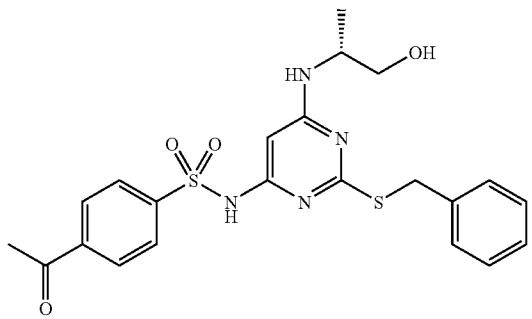

Yield: 6 mg.
MS: APCI (+ve) 473 [M+H]+

EXAMPLE 90

N-{2-(Benzylthio)-6-[((1R)-2-hydroxy-1-methyl ethyl)amino]pyrimidin-4-yl}-2-chloro-4,5-difluo-robenzenesulfonamide

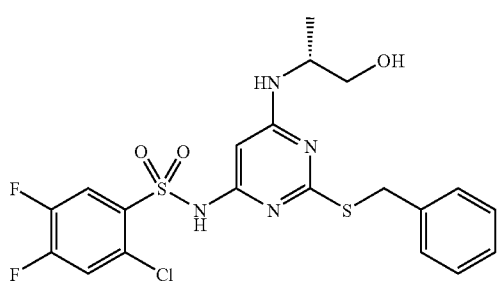

Yield: 5 mg.
MS: APCI (+ve) 501/503 [M+H]+

EXAMPLE 91

N-{2-(Benzylthio)-6-[((1R)-2-hydroxy-1-methyl-ethyl)amino]pyrimidin-4-yl}-5-chloro-2,4-difluorobenzenesulfonamide

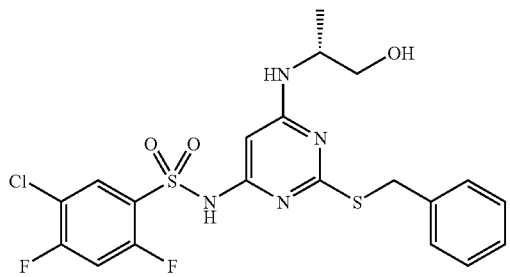

Yield: 4 mg.
MS: APCI (+ve) 501/503 [M+H]+

EXAMPLE 92

N-{2-(Benzylthio)-6-[((1R)-2-hydroxy-1-methyl-ethyl)amino]pyrimidin-4-yl}-4-chloro-2,5-difluorobenzenesulfonamide

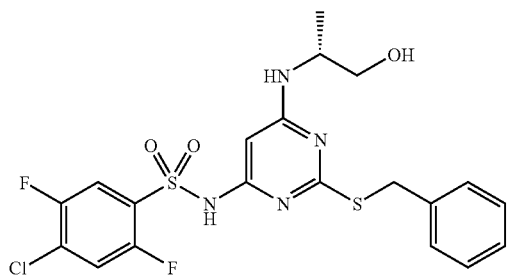

Yield: 9 mg.
MS: APCI (+ve) 501/503 [M+H]+

EXAMPLE 93

N-{2-(Benzylthio)-6-[((1R)-2-hydroxy-1-methyl-ethyl)amino]pyrimidin-4-yl}biphenyl-4-sulfonamide

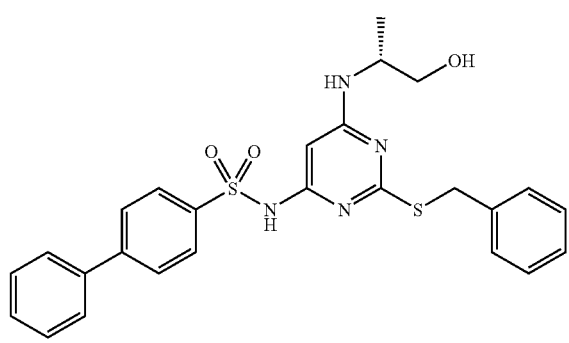

Yield: 14 mg.
MS: APCI (+ve) 507 [M+H]+

EXAMPLE 94

N-{2-(Benzylthio)-6-[((1R)-2-hydroxy-1-methyl-ethyl)amino]pyrimidin-4-yl}-2-methoxy-4-methyl-benzenesulfonamide

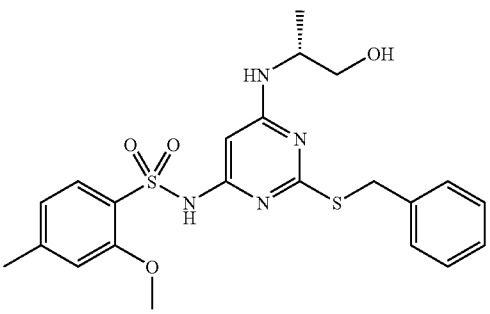

Yield: 10 mg.
MS: APCI (+ve) 475 [M+H]+

EXAMPLE 95

N-{2-(Benzylthio)-6-[((1R)-2-hydroxy-1-methyl-ethyl)amino]pyrimidin-4-yl}-3-chloro-4-methylbenzensulfonamide

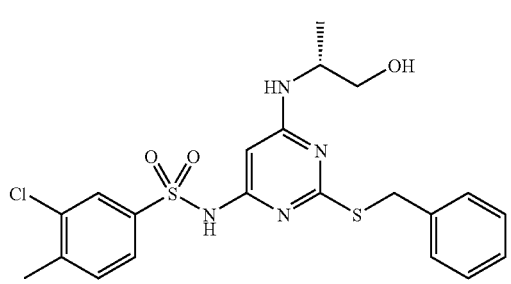

Yield: 14 mg.
MS: APCI (+ve) 479/481 [M+H]+

EXAMPLE 96

N-{2-(Benzylthio)-6-[((1R)-2-hydroxy-1-methyl-ethyl)amino]pyrimidin-4-yl}-4-bromo-2-methylbenzenesulfonamide

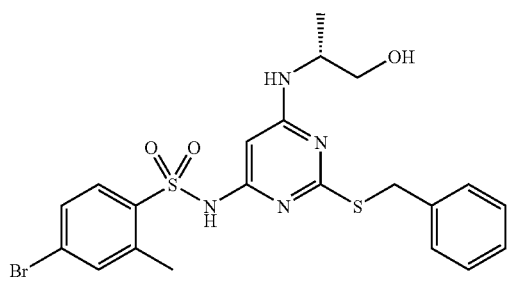

Yield: 5 mg.
MS: APCI (+ve) 523/525 [M+H]+

EXAMPLE 97

N-{2-(Benzylthio)-6-[((1R)-2-hydroxy-1-methyl-ethyl)amino]pyrimidin-4-yl}-4-phenoxybenzene-sulfonamide

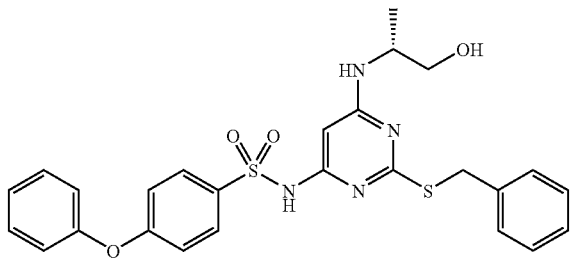

Yield: 7 mg.
MS: APCI (+ve) 523 [M+H]$^+$

EXAMPLE 98

N-{2-(Benzylthio)-6-[((1R)-2-hydroxy-1-methyl-ethyl)amino]pyrimidin-4-yl}-4-chloro-2,5-dimethyl-benzenesulfonamide

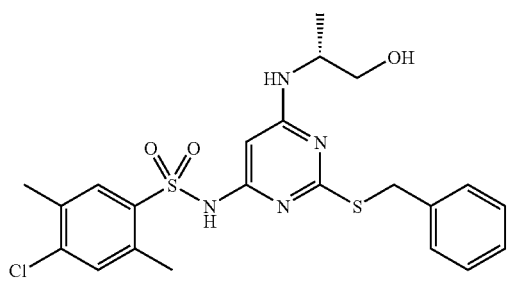

Yield: 14 mg.
MS: APCI (+ve) 493/495 [M+H]$^+$

EXAMPLE 99

N-{2-(Benzylthio)-6-[((1R)-2-hydroxy-1-methyl-ethyl)amino]pyrimidin-4-yl}-2,3,4-trifluorobenzene-sulfonamide

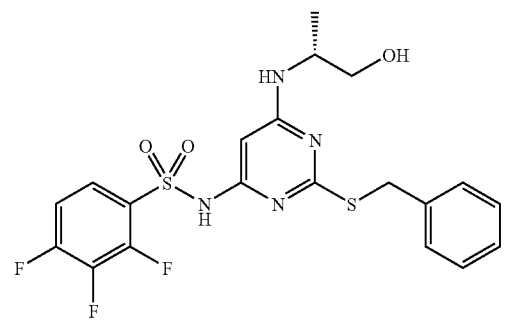

Yield: 5 mg
MS: APCI (+ve) 485 [M+H]$^+$.

General Procedure for the Synthesis of Examples 100 to 105.

To the required sulfonyl chloride (0.15 mM) was added a solution of the subtitle product of Example 3 step (0.05 mM) in pyridine (0.4 ml) and 4-N,N-dimethylaminopyridine (0.05 mM) in pyridine (0.2 ml) before the reaction mixture was stirred at room temperature for three days. 3M Hydrochloric acid (0.2 ml) was added and stirring maintained for 18 h before the solvent was removed under reduced pressure. The residue was dissolved in DMSO/H$_2$O (400 µl; 3:1) and filtered through a PORVAIR filter before the product was purified by mass directed reverse phase HPLC to afford the title products of Examples 100 to 105 as solution samples.

EXAMPLE 100

N-(2-(Benzylthio)-6-{[(1R)-2-hydroxy-1-methyl-ethyl]amino}pyrimidin-4-yl)-4-methoxybenzene-sulfonamide

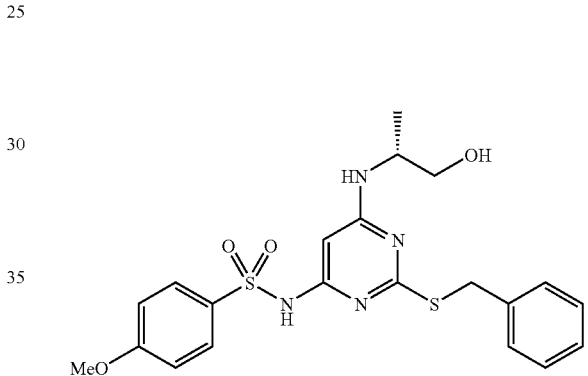

MS: APCI (+ve) 461 [M+H]$^+$

EXAMPLE 101

N-(2-(Benzylthio)-6-{[(1R)-2-hydroxy-1-methyl-ethyl]amino}pyrimidin-4-yl)-2,4-dichlorobenzene-sulfonamide

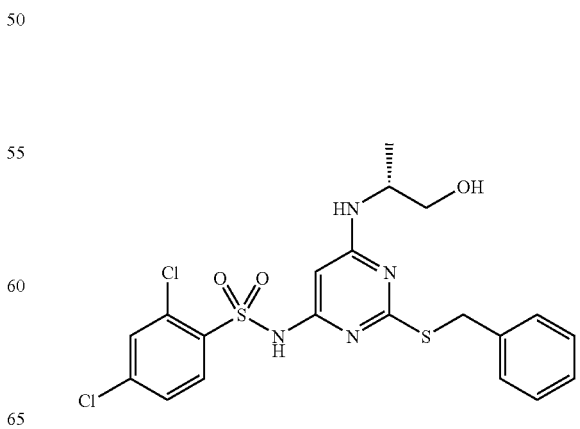

MS: APCI (+ve) 499 [M+H]$^+$

EXAMPLE 102

N-(2-(Benzylthio)-6-{[(1R)-2-hydroxy-1-methylethyl]amino}pyrimidin-4-yl)thiophene-2-sulfonamide

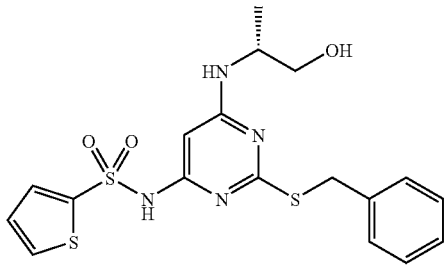

MS: APCI (+ve) 437 [M+H]+

EXAMPLE 103

N-(2-(Benzylthio)-6-{[(1R)-2-hydroxy-1-methylethyl]amino}pyrimidin-4-yl)-2,5-dimethylbenzenesulfonamide

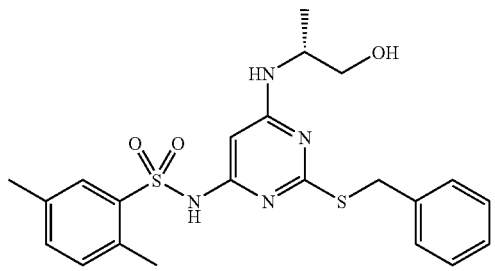

MS: APCI (+ve) 459 [M+H]+

EXAMPLE 104

N-(2-(Benzylthio)-6-{[(1R)-2-hydroxy-1-methylethyl]amino}pyrimidin-4-yl)-1,2-dimethyl-1H-imidazole-4-sulfonamide

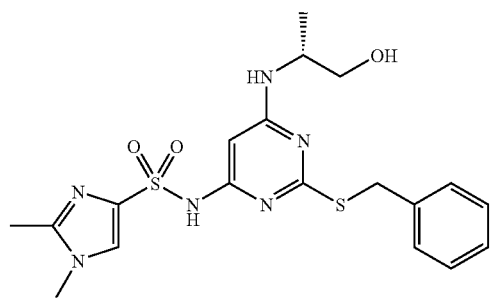

MS: APCI (+ve) 449 [M+H]+

EXAMPLE 105

N-(2-(Benzylthio)-6-{[(1R)-2-hydroxy-1-methylethyl]amino}pyrimidin-4-yl)butane-1-sulfonamide

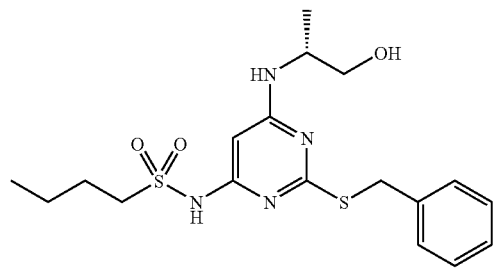

MS: APCI (+ve) 411 [M+H]+

EXAMPLE 106

N-(2-[(2,3-Difluorobenzyl)thio]-6-{[(1R)-2-hydroxy-1-methylethyl]amino}pyrimidin-4-yl)morpholine-4-sulfonamide

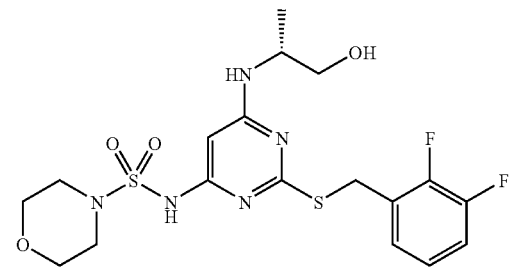

2,3-Difluorobenzyl bromide (0.95 g) was added to an aliquot of the reaction solution of step iv) (2 ml) containing the subtitle product of step iv) and the reaction stirred for 2 h. The reaction was partitioned between EtOAc (20 ml) and brine (20 ml). The aqueous was extracted with EtOAc (2×20 ml) and the organics concentrated in vacuo. The residue was purified by column chromatography (30% then 40% EtOAc/iso-hexane) to afford the subtitle product as an oil that was diluted in acetonitrile (5 ml) and 2M hydrochloric acid (5 ml) and was stirred overnight before removal of the volatiles in vacuo. The crude material was purified by reverse phase HPLC (gradient 95% to 20% 0.02M ammonium hydroxide/acetonitrile) to yield the title compound as a white solid. Yield: 0.17 g.

MS APCI(+ve) 476 [M+H]+

$^1$H NMR $\delta_{(DMSO)}$ 10.57 (1H, bs), 7.40 (1H, bt), 7.32 (2H, m), 7.15 (1H, m), 5.90 (1H, s), 4.71 (1H, bs), 4.39 (2H, t), 4.02 (1H, bs), 3.60 (4H, t), 3.40 (1H, m), 3.30 (1H, m), 3.18 (4H, bs), 1.06 (3H, d).

The intermediates for this compound were prepared as follows:

i) N-{6-Chloro-2-[benzylthio]pyrimidin-4-yl}-N-{[2-(trimethylsilyl)-ethoxy]methyl}morpholine-4-sulfonamide The subtitle compound was prepared as an oil by the method of Example 32 step i) (8.9 g) using the subtitle product of Example 19 step ii) and the subtitle product of Example 36 step i) (4.7 g) and 2-(trimethylsilyl)ethoxymethyl chloride (6.1 g). Yield: 11.8 g.

MS APCI(+ve) 401 [M+H]+ ii) N-(2-[benzylthio]-6-{[(1R)-2-hydroxy-1-methyl-ethyl]amino}-pyrimidin-4-yl)-N-{[2-(trimethylsilyl)ethoxy]methyl}morpholine-4-sulfonamide The subtitle compound was prepared as a yellow oil by the method of Example 43 step by reacting the subtitle product of step i) (11.75 g) with (R)-alaninol (3.4 ml) in NMP (30 ml). Yield: 12.2 g.

MS APCI(+ve) 570 [M+H]+ iii) N-(2-[benzylsulfonyl]-6-{[(1R)-2-hydroxy-1-methylethyl]amino}-pyrimidin-4-yl)-N-{[2-(trimethylsilyl)ethoxy]methyl}morpholine-4-sulfonamide m-Chloroperbenzoic acid (5.87 g) was added as a single portion to a solution of the subtitle product of step iii) (5.83 g) in DCM (220 ml) and stirred for 2.5 h. A further aliquot of m-chloroperbenzoic acid (1.0 g) was added and stirring maintained for 1 h. Saturated sodium thiosulfate solution (100 ml) was added and stirred vigourously until no peroxides were detected. The organics were separated and extracted with saturated sodium bicarbonate solution (200 ml) and brine (50 ml), dried (MgSO$_4$) and concentrated to yield the subtitle compound as a crude beige white solid. Yield: 5.6 g.

MS APCI(+ve) 602 [M+H]+ iv) Sodium 4-{[(1R)-2-hydroxy-1-methylethyl]amino}-6-((morpholin-4-ylsulfonyl){[2-(trimethylsilyl)ethoxy]methyl}amino)pyrimidine-2-thiolate Sodium hydrosulfide hydrate (0.62 g) was added to a solution of the subtitle product of step iii) (2.5 g) in DMSO (5 ml) and the green solution stirred for 1.25 h. A further aliquot of sodium hydrosulfide hydrate (0.28 g) was added and stirred for 45 min. A further aliquot of sodium hydrosulfide hydrate (0.32 g) was added and stirred for 1.25 h before the addition of a final aliquot of sodium hydrosulfide hydrate (0.10 g) in DMSO (1 ml). The resulting reaction solution was diluted with DMSO (10 ml) and used directly in the following step. The subtitle compound was also kept as a stock solution for further reaction with alkyl halides, described in Examples 107-110.

MS APCI(+ve) 480 [M+H]+

EXAMPLE 107

N-{6-{[(1R)-2-Hydroxy-1-methylethyl]amino}-2-[(2,3,4-trifluorobenzyl)thio]-pyrimidin-4-yl}morpholine-4-sulfonamide

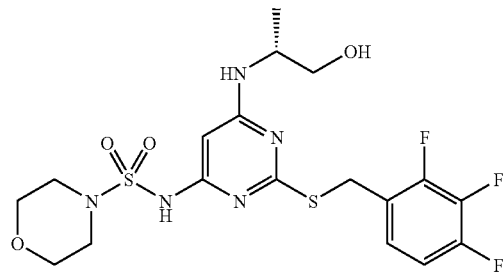

2,3,4-Trifluorobenzyl bromide (1.04 g) was added to an aliquot of the reaction solution of Example 106 step iv) (2 ml) containing the subtitle product of Example 106 step iv) and the reaction stirred for 2 h. The reaction was partitioned between EtOAc (20 ml) and brine (20 ml). The aqueous was extracted with EtOAc (2×20 ml) and the organics concentrated in vacuo. The residue was purified by column chromatography (50% then 60% EtOAc/iso-hexane) to afford the subtitle product as an oil that was diluted in acetonitrile (5 ml) and 2M hydrochloric acid (5 ml) and was stirred overnight before removal of the volatiles in vacuo. The crude material was purified by reverse phase HPLC (gradient 95% to 20% 0.02M ammonium hydroxide/acetonitrile) to yield the title compound as a white solid. Yield: 0.14 g.

MS APCI(+ve) 494 [M+H]+

$^1$H NMR $\delta_{(DMSO)}$ 10.57 (1H, bs), 7.45 (1H, bs), 7.25 (2H, m), 5.90 (1H, s), 4.71 (1H, bs), 4.36 (2H, s), 4.02 (1H, s), 3.60 (4H, bs), 3.38 (1H, m), 3.30 (1H, m), 3.15 (4H, bs), 1.07 (3H, d).

EXAMPLE 108

N-{6-{[(1R)-2-Hydroxy-1-methylethyl]amino}-2-[(2,3,5-trifluorobenzyl)thio]-pyrimidin-4-yl}morpholine-4-sulfonamide

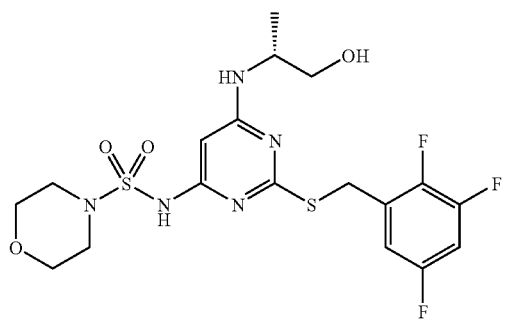

2,3,5-Trifluorobenzyl bromide (1.04 g) was added to an aliquot of the reaction solution of Example 106 step iv) (2 ml) containing the subtitle product of Example 106 step iv) and the reaction stirred for 2 h. The reaction was partitioned between EtOAc (20 ml) and brine (20 ml). The aqueous was extracted with EtOAc (2×20 ml) and the organics concentrated in vacuo. The residue was purified by column chromatography (50% then 60% EtOAc/iso-hexane) to afford the subtitle product as an oil that was diluted in acetonitrile (5 ml) and 2M hydrochloric acid (5 ml) and was stirred overnight before removal of the volatiles in vacuo. The crude material was purified by reverse phase HPLC (gradient 95% to 20% 0.02M ammonium hydroxide/acetonitrile) to yield the title compound as a white solid. Yield: 0.16 g.

MS APCI(−ve) 492 [M−H]−

$^1$H NMR $\delta_{(DMSO)}$ 10.61 (1H, bs), 7.38 (3H, bm), 5.91 (1H, s), 4.71 (1H, bs), 4.36 (2H, t), 4.02 (1H, bs), 3.59 (4H, bs), 3.37 (1H, m), 3.30 (1H, m), 3.14 (4H, bs), 1.05 (3H, d).

EXAMPLE 109

N-(2-[(2,3-Difluoro-4-methylbenzyl)thio]-6-{[(1R)-2-hydroxy-1-methylethyl]amino}pyrimidin-4-yl)morpholine-4-sulfonamide

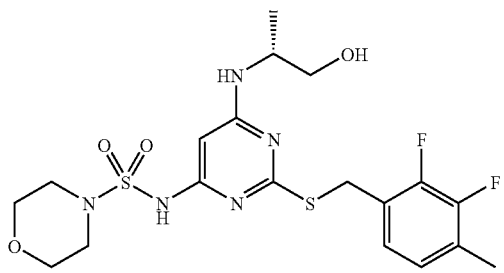

2,3-Difluoro-4-methylbenzyl bromide (1.02 g) was added to an aliquot of the reaction solution of Example 106 step iv) (2 ml) containing the subtitle product of Example 106 step iv) and the reaction stirred for 2 h. The reaction was partitioned between EtOAc (20 ml) and brine (20 ml). The aqueous was extracted with EtOAc (2×20 ml) and the organics concentrated in vacuo. The residue was purified by column chromatography (70% EtOAc/iso-hexane) to afford the subtitle product as an oil that was diluted in acetonitrile (5 ml) and 2M hydrochloric acid (5 ml) and was stirred overnight before removal of the volatiles in vacuo. The crude material was purified by reverse phase HPLC (gradient 95% to 20% 0.02M ammonium hydroxide/acetonitrile) to yield the title compound as a white solid. Yield: 0.12 g.

MS APCI(-ve) 488 [M-H]⁻

$^1$H NMR) $\delta_{(DMSO)}$ 10.57 (1H, bs), 7.28 (2H, bs), 7.02 (1H, t), 5.90 (1H, bs), 4.71 (1H, bs), 4.34 (2H, bm), 4.03 (1H, bs), 3.59 (4H, bs), 3.39 (1H, m), 3.30 (1H, m), 3.15 (4H, bs), 2.24 (3H, s), 1.07 (3H, d).

EXAMPLE 110

N-(2-[(4-Chloro-2-fluorobenzyl)thio]-6-{[(1R)-2-hydroxy-1-methylethyl]amino}-pyrimidin-4-yl)morpholine-4-sulfonamide

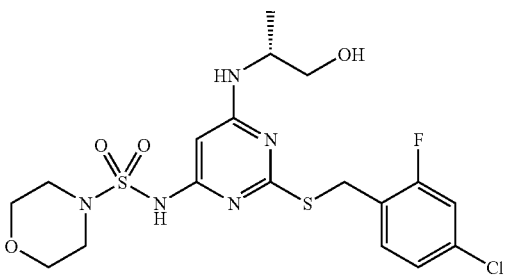

4-Chloro-2-fluorobenzyl bromide (1.03 g) was added to an aliquot of the reaction solution of Example 106 step iv) (2 ml) containing the subtitle product of Example 106 step iv) and the reaction stirred for 2 h. The reaction was partitioned between EtOAc (20 ml) and brine (20 ml). The aqueous was extracted with EtOAc (2×20 ml) and the organics concentrated in vacuo. The residue was purified by column chromatography (66% EtOAc/iso-hexane) to afford the subtitle product as an oil that was diluted in acetonitrile (5 ml) and 2M hydrochloric acid (5 ml) and was stirred overnight before removal of the volatiles in vacuo. The crude material was purified by reverse phase HPLC (gradient 95% to 20% 0.02M ammonium hydroxide/acetonitrile) to yield the title compound as a white solid. Yield: 90 mg.

MS APCI(-ve) 490 [M-H]⁻

$^1$H NMR $\delta_{(DMSO)}$ 10.56 (1H, bs), 7.63 (1H, bt), 7.42 (1H, d), 7.31 (1H, bs), 7.23 (1H., d), 5.90 (1H, s), 4.72 (1H, bs), 4.32 (2H, bs), 4.30 (1H, bs), 3.59 (4H, bs), 3.40 (1H, m), 3.30 (1H, m), 3.15 (4H, bs), 1.06 (3H, d).

EXAMPLE 111

N-(2-[(2,3-Difluorobenzyl)thio]-6-{[(1R)-2-hydroxy-1-methylethyl]amino}pyrimidin-4-yl)pyrrolidine-1-sulfonamide

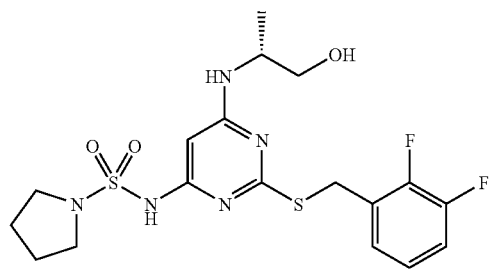

2,3-Difluorobenzyl bromide (2.65 g) was added to an aliquot of the reaction solution of step v) (12.6 ml) containing the subtitle product of step v) and the reaction stirred for 1 h. The reaction was partitioned between EtOAc (20 ml) and H₂O (20 ml), the organics were recovered, dried (MgSO₄) and concentrated in vacuo. The residue was purified by column chromatography (650:350:1 iso-hexane/EtOAc/AcOH) to afford the subtitle compound as an oil that was diluted in trifluoroacetic acid (2 ml) and was stirred for 12 min before quenching the reaction by the addition of 1M sodium hydroxide solution to pH>10. The aqueous was washed with Et₂O before saturated ammonium chloride solution was added to acidify the aqueous to pH 4 followed by extracting with EtOAc (3×20 ml). The EtOAc extracts were combined, dried (MgSO₄) and concentrated in vacuo. The crude material was purified by reverse phase HPLC (gradient 95% to 20% 0.02M ammonium hydroxide/acetonitrile) to yield the title compound as a white solid. Yield: 0.52 g.

MS APCI(+ve) 460 [M+H]⁺

$^1$H NMR $\delta_{(CDCl3)}$ 7.25-7.20 (1H, m), 7.08-6.97 (2H, m), 5.95 (1H, s), 4.98 (1H, d), 4.34 (2H, s), 4.15-4.01 (1H, m), 3.73-3.69 (1H, m), 3.60-3.55 (1H, m), 3.39 (4H, t), 1.93-1.90 (4H, m), 1.21 (3H, d).

The intermediates for this compound were prepared as follows:

i) Pyrrolidine-1-sulfonamide

Pyrrolidine (3.37 g) and sulfamide (7.10 g) in 1,4-dioxane (110 ml) were heated at reflux for 24 h. The solvent was evaporated under reduced pressure and the resulting solid suspended in CHCl₃. The suspension was filtered and the filtrate concentrated in vacuo to afford the subtitle compound as a white solid. Yield: 5.35 g.

¹H NMR δ$_{(CDCl3)}$ 4.46 (2H, s), 3.31 (4H, t), 1.96-1.92 (4H, m).

ii) N-[2-(Benzylthio)-6-chloropyrimidin-4-yl]-N-{[2-(trimethylsilyl)ethoxy]methyl}-pyrrolidine-1-sulfonamide To a solution of the product of step i) (5.0 g) in dry DMF (60 ml) at 0° C. under nitrogen was added 60% sodium hydride (2.66 g). The reaction was allowed to warm outside the cooling bath for 15 min before recooling to 0° C. and addition of the product from Example 19 step (9.03 g) in DMF (20 ml) and the whole allowed to further stir at room temperature for 3 h. The reaction was quenched with 2-(trimethylsilyl) ethoxymethyl chloride (6.50 ml) and allowed to stir for 18 h before removal of the volatiles in vacuo and partitioning of the residue between EtOAc (100 ml) and H₂O (200 ml). The aqueous was washed further with EtOAc (2×100 ml) and the organics combined, dried (MgSO₄) and concentrated in vacuo. The residue was purified by column chromatography (1:18:181 AcOH/EtOAc/iso-hexane) to afford the subtitle compound as a colourless oil. Yield: 8.26 g.

MS APCI(+ve) 515 [M+H]⁺ iii) N-(2-(Benzylthio)-6-{[(1R)-2-hydroxy-1-methylethyl]amino}pyrimidin-4-yl)-N-{[2-(trimethylsilyl)ethoxy]methyl}pyrrolidine-1-sulfonamide The subtitle compound was prepared as a yellow oil by the method of Example 43 step ii) by reacting the subtitle product of step ii) (8.26 g) with (R)-alaninol (3.61 g) in NMP (60 ml). Yield: 7.6 g.

MS APCI(+ve) 554 [M+H]⁺ iv) N-(2-(Benzylsulfonyl)-6-{[(1R)-2-hydroxy-1-methylethyl]amino}pyrimidin-4-yl)-N-{[2-(trimethylsilyl)ethoxy]methyl}pyrrolidine-1-sulfonamide m-Chloroperbenzoic acid (11.07 g) was added as a single portion to a solution of the subtitle product of step (9.41 g) in DCM (44 ml) and stirred for 6 h. Saturated sodium thiosulfate solution (100 ml) was added and stirred vigourously until no peroxides were detected. The organics were separated and extracted with saturated sodium bicarbonate solution (200 ml) and brine (50 ml), dried (MgSO₄) and concentrated to yield the subtitle compound as a colourless foam. Yield: 1.0 g.

MS APCI(+ve) 531 [M+H]⁺ v) Sodium 4-{[(1R)-2-hydroxy-1-methylethyl]amino}-6-((pyrrolidin-1-ylsulfonyl){[2-(trimethylsilyl)ethoxy]methyl}amino)pyrimidine-2-thiolate Sodium hydrosulfide hydrate (2.15 g) was added to a solution of the subtitle product of step iii) (4.5 g) in DMSO (37.8 ml) and the green solution stirred for 1 h. A further aliquot of sodium hydrosulfide hydrate (0.1 g) was added and stirred for 1 h. A further aliquot of sodium hydrosulfide hydrate (0.1 g) was added and stirred for 2 h before the addition of a final aliquot of sodium hydrosulfide hydrate (0.05 g). The resulting reaction solution was used directly in the following step. The subtitle compound was also kept as a stock solution for further reaction with alkyl halides, described in Examples 112-113.

MS APCI(+ve) 351 [M+H]⁺

EXAMPLE 112

N-{6-{[(1R)-2-Hydroxy-1-methylethyl]amino}-2-[(2,3,4-trifluorobenzyl)thio]-pyrimidin-4-yl}pyrrolidine-1-sulfonamide

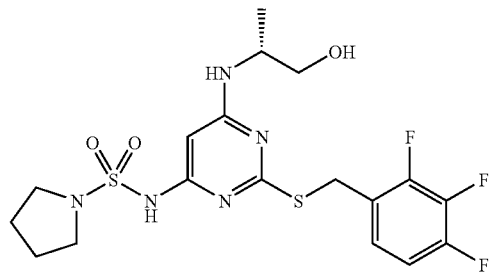

The title compound was prepared as a white solid by the method of Example 111 using the subtitle product of Example 111 step v) (12.6 ml) and 2,3,4-trifluorobenzyl bromide (2.88 g). Yield: 0.12 g.

MS APCI(+ve) 478 [M+H]⁺

¹H NMR δ$_{(CDCl3)}$ 7.22-7.16 (1H, m), 7.01-6.86 (2H, m), 5.95 (1H, s), 5.01 (1H, d), 4.30 (2H, s), 4.07 (1H, m), 3.74-3.70 (1H, m), 3.60-3.56 (1H, m), 3.39 (4H, t), 1.94-1.90 (4H, m), 1.23 (3H, d).

EXAMPLE 113

N-(2-[(2,3-Difluoro-4-methylbenzyl)thio]-6-{[(1R)-2-hydroxy-1-methylethyl]amino}-pyrimidin-4-yl)pyrrolidine-1-sulfonamide

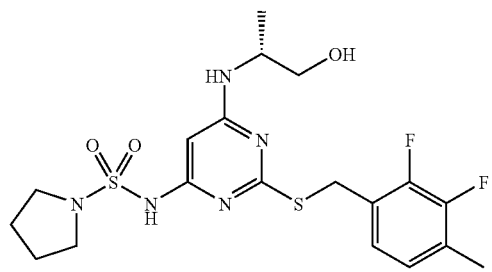

The title compound was prepared as a white solid by the method of Example 111 using the subtitle product of Example 111 step v) (12.6 ml) and 2,3-difluoro-4-methylbenzyl bromide (2.83 g). Yield: 40 mg.

MS APCI(−ve) 372 [M−H]⁻

¹H NMR δ$_{(DMSO)}$ 10.36 (1H, s), 7.27 (1H, t), 7.01 (1H, t), 5.78 (1H, s), 4.69 (1H, t), 4.32 (2H, s), 4.03-3.87 (1H, m), 3.33-3.29 (1H, m), 3.28-3.22 (4H, m), 2.24 (3H, s), 1.78-1.75 (4H, m), 1.06 (3H, d).

EXAMPLE 114

N-(2-[(2,3-Difluorobenzyl)thio]-6-{[(1R)-2-hydroxy-1-methylethyl]amino}pyrimidin-4-yl)piperidine-1-sulfonamide

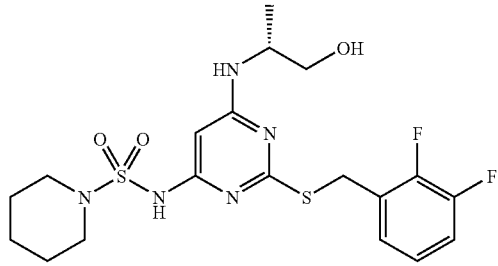

The subtitle product of step was heated in (R)-alaninol (2 ml) for 8 days at 80° C. before partitioning between EtOAc (50 ml) and H₂O (50 ml). The organics were recovered, dried (MgSO₄) and concentrated in vacuo. The residue was purified by column chromatography (550:450:1 EtOAc/iso-hexane/AcOH) to afford the title compound as a white solid. Yield: 106 mg.

MS APCI(+ve) 474 [M+H]⁺

¹H NMR δ$_{(CDCl_3)}$ 7.24-7.20 (1H, m), 7.08-6.98 (2H, m), 6.02 (1H, s), 4.36 (2H, s), 4.18-3.96 (1H, m), 3.74-3.70 (1H, m), 3.61-3.57 (1H, m), 3.26 (4H, t), 1.65-1.59 (4H, m), 1.57-1.51 (2H, m), 1.22 (3H, d).

The intermediates for this compound were prepared as follows:

i) Piperidine-1-sulfonamide

Piperidine (3.0 g) and sulfamide (5.93 g) in 1,4-dioxane (100 ml) were heated at reflux for 24 h. The solvent was evaporated under reduced pressure and the resulting solid suspended in CHCl₃. The suspension was filtered and the filtrate concentrated in vacuo to afford the subtitle compound as a white solid. Yield: 3.85 g.

¹H NMR δ$_{(DMSO)}$ 6.65 (2H, s), 2.92 (4H, t), 1.59-1.53 (4H, m), 1.45-1.40 (2H, m).

ii) N-{3-Chloro-5-[(2,3-difluorobenzyl)thio]phenyl}piperidine-1-sulfon amide 60% Sodium hydride (0.20 g) was added to a solution of the subtitle product of step i) (0.4 g) in DMF (6.7 ml) at 0° C. The reaction was allowed to warm outside the cooling bath for 15 min before recooling to 0° C. for 15 min. A solution of the subtitle product of Example 39 step ii) (0.75 g) in DMF (2 ml) was then added and stirring maintained for 3 h. The reaction mixture was neutralised with methanolic hydrogen chloride before concentrating in vacuo. The residue was partitioned between EtOAc (100 ml) and H₂O (200 ml) and the organics recovered, dried (MgSO₄) and concentrated in vacuo. The residue was purified by column chromatography (1:20:79 AcOH/EtOAc/iso-hexane) to afford the subtitle compound as a colourless oil. Yield: 1.3 g.

MS APCI(+ve) 435 [M+H]⁺

EXAMPLE 115

N-(2-[(2-Fluoro-3-methylbenzyl)thio]-6-{[(1R)-2-hydroxy-1-methylethyl]amino}-pyrimidin-4-yl)methanesulfonamide

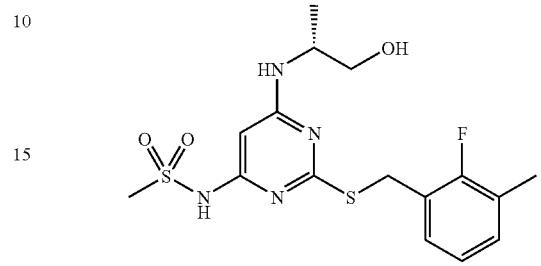

A solution of the subtitle product of step (1.0 g) in (R)-alaninol (1.5 ml) was heated at 80° C. for 18 h before partitioning between EtOAc and H₂O. The organics were recovered, dried (MgSO₄) and concentrated. The residue was purified by column chromatography (1:76:133 AcOH/EtOAc/iso-hexane) before diluting the crude material in trifluoroacetic acid (2 ml) and stirring for 12 min before quenching the reaction by the addition of 1M sodium hydroxide solution to pH>10. The aqueous was extracted with Et₂O before being acidified with saturated ammonium chloride solution to pH 4 and extracting with EtOAc (3×20 ml). The EtOAc extracts were dried (MgSO₄) and concentrated in vacuo. The crude material was purified by reverse phase HPLC (gradient 95% to 20% 0.02M ammonium hydroxide/acetonitrile) to yield the title compound as a white solid. Yield: 0.33 g.

MS APCI(+ve) 401 [M+H]⁺

¹H NMR δ$_{(DMSO)}$ 10.53 (1H, s), 7.36 (1H, t), 7.17 (1H, t), 7.01 (1H, t), 5.77 (1H, s), 4.70 (1H, s), 4.33 (2H, s), 4.01 (1H, s), 3.42-3.37 (1H, m), 3.32 (3H, s), 3.31-3.26 (1H, m), 2.23 (3H, s), 1.07 (3H, d).

The intermediates for this compound were prepared as follows:

i) 2-[(2-Fluoro-3-methylbenzyl)thio]pyrimidine-4,6-diol

The subtitle compound was prepared as a yellow solid by the method of Example 39 step i) using 2-fluoro-3-methylbenzyl bromide (7.0 g), 2-mercaptopyrimidine-4,6-diol (5.0 g) and potassium hydroxide (1.93 g). Yield: 8.36 g.

MS APCI(+ve) 267 [M+H]⁺ ii) 4,6-Dichloro-2-[(2-fluoro-3-methylbenzyl)thio]pyrimidine

The subtitle compound was prepared as white crystals by the method of Example 39 step ii) using the subtitle product of step i) (8.36 g), phosphorus oxychloride (47 ml) and N,N-dimethylaniline (8.9 ml). Yield: 7.32 g.

¹H NMR δ$_{CDCl_3}$ 7.32 (1H, t), 7.10 (1H, t), 7.03 (1H, s), 6.96 (1H, t), 4.40 (2H, s), 2.28 (3H, s).

iii) N-{6-Chloro-2-[(2-fluoro-3-methylbenzyl)thio]pyrimidin-4-yl}-N-{[2-(trimethylsilyl)ethoxy]methyl}azetidine-1-sulfonamide The subtitle compound was prepared as a colourless oil by the method of Example 39 step iii) using the subtitle product of step ii) (2.45 g), methanesulfonamide (0.76 g), 60% sodium hydride (0.64 g) and 2-(trimethylsilyl)ethoxymethyl chloride (1.42 ml). Yield: 3.14 g.
MS APCI(+ve) 434 [M+H]⁺

EXAMPLE 116

N-{2-[(2-Fluoro-3-methylbenzyl)thio]-6-[(2-hydroxy-1,1-dimethylethyl)amino]-pyrimidin-4-yl}methanesulfonamide

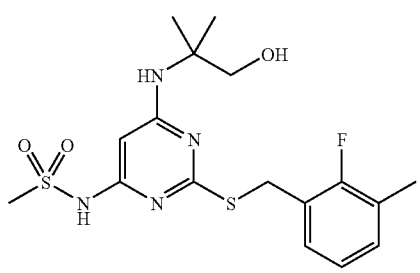

The title compound was prepared as a white solid by the method of Example 115 using the subtitle product of Example 115 step (1.0 g), 2-amino-2-methyl-1 propanol (1.5 ml) and trifluoroacetic acid (2 ml). Yield: 0.19 g.
MS APCI(+ve) 415 [M+H]⁺
$^1$H NMR $\delta_{(CDCl3)}$ 7.25 (1H, t), 7.08 (1H, t), 6.97 (1H, t), 5.95 (1H, s), 4.94 (1H, s), 4.34 (2H, s), 3.64 (2H, s), 3.16 (3H, s), 2.28 (3H, s), 1.36 (6H, s).

EXAMPLE 117

N-(2-[(2-Fluoro-3-methylbenzyl)thio]-6-{[(1R)-1-(hydroxymethyl)propyl]amino}-pyrimidin-4-yl)methanesulfonamide

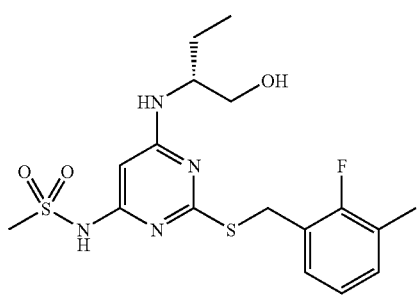

The title compound was prepared as a white solid by the method of Example 115 using the subtitle product of Example 115 step iii) (1.0 g), (R)-(−)-2-amino-1-butanol (1.5 ml) and trifluoroacetic acid (2 ml). Yield: 0.19 g.
MS APCI(+ve) 415 [M+H]⁺
$^1$H NMR $\delta_{(DMSO)}$ 10.52 (1H, s), 7.36 (1H, t), 7.17 (1H, t), 7.01 (1H, t), 5.81 (1H, s), 4.65 (1H, s), 4.32 (2H, s), 3.92 (1H, s), 3.42-3.37 (1H, m), 3.31 (3H, s), 3.34-3.29 (1H, m), 2.23 (3H, s), 1.65-1.56 (1H, m), 1.41-1.32 (1H, m), 0.84 (3H, t).

EXAMPLE 118

N-(2-{[2-Fluoro-3-(trifluoromethyl)benzyl]thio}-6-{[(1R)-2-hydroxy-1-methylethyl]-amino}pyrimidin-4-yl)methanesulfonamide

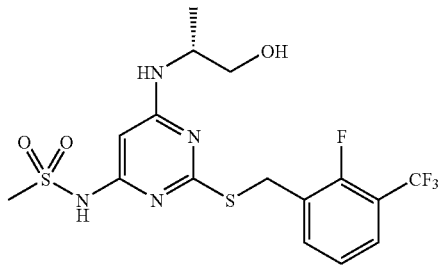

The title compound was prepared as pale yellow crystals by the method of Example 115 using the subtitle product of step iii) (0.21 g) and (R)-alaninol (0.3 ml). Yield: 0.12 g.
MS APCI(+ve) 455 [M+H]⁺
$^1$H NMR $\delta_{(CDCl3)}$ 7.71 (1H, t), 7.49 (1H, t), 7.19 (1H, t), 5.95 (1H, s), 5.07 (1H, s), 4.35 (2H, s), 3.74-3.69 (1H, m), 3.59-3.54 (1H, m), 3.15 (3H, s), 1.20 (3H, d).

The intermediates for this compound were prepared as follows:

i) 2-{[2-Fluoro-3-(trifluoromethyl)benzyl]thio}pyrimidine-4,6-diol

The subtitle compound was prepared as a yellow solid by the method of Example 39 step i) using 2-fluoro-3-(trifluoromethyl)benzyl bromide (2.0 g), 2-mercaptopyrimidine-4,6-diol (1.12 g) and potassium hydroxide (0.44 g). Yield: 2.23 g.
MS APCI(+ve) 321 [M+H]⁺ ii) 4,6-Dichloro-2-[(2-fluoro-(3-trifluoromethyl)benzyl)thio]pyrimidine

The subtitle compound was prepared as white crystals by the method of Example 39 step using the subtitle product of step i) (2.23 g), phosphorus oxychloride (10.4 ml) and N,N-dimethylaniline (2.0 ml). Yield: 1.7 g.
$^1$H NMR $\delta_{(CDCl3)}$ 7.75 (1H, t), 7.52 (1H, t), 7.18 (1H, t), 7.06 (1H, s), 4.43 (2H, s).

iii) N-(6-Chloro-2-{[2-fluoro-3-(trifluoromethyl)benzyl]thio}pyrimidin-4-yl)-N-{[2-(trimethylsilyl)ethoxy]methyl}methanesulfonamide The subtitle compound was prepared as a colourless oil by the method of Example 39 step iii) using the subtitle product of step ii) (0.57 g), methanesulfonamide (0.15 g), 60% sodium hydride (0.26 g) and 2-(trimethylsilyl)ethoxymethyl chloride (0.3 ml). Yield: 0.21 g.

¹H NMR δ_(CDCl3) 7.77 (1H, t), 7.53 (1H, t), 7.19 (1H, t), 7.12 (1H, s), 5.32 (2H, s), 4.45 (2H, s), 3.66 (2H, t), 3.32 (3H, s), 0.93 (2H, t), 0.00 (9H, s).

EXAMPLE 119

N-(2-[(2,3-Difluoro-4-methylbenzyl)thio]-6-{[(1R)-2-hydroxy-1-methylethyl]amino}-pyrimidin-4-yl)methanesulfonamide

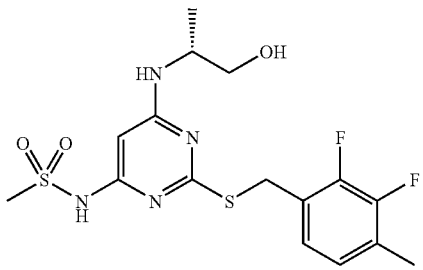

The title compound was prepared from a solution of the product of Example 43 step iv) (4 ml) and quenching 2,3-difluoro-4-methylbenzyl bromide (1.46 g) using the method described for Example 43 to give the title compound as a white solid. Yield: 4 mg.

MS APCI(+ve) 419 [M+H]⁺ ¹H NMR δ_(CD3OD) 7.27-7.23 (1H, m), 6.93-6.89 (1H, m), 5.56 (1H, s), 4.41 (2H, s), 3.91-3.81 (1H, m), 3.55-3.50 (1H, m), 3.48-3.43 (1H, m), 3.03 (3H, s), 2.25 (3H, s), 1.16 (3H, d).

EXAMPLE 120

N-(2-[(2-Fluoro-3-methoxybenzyl)thio]-6-{[(1R)-2-hydroxy-1-methylethyl]amino}-pyrimidin-4-yl)methanesulfonamide

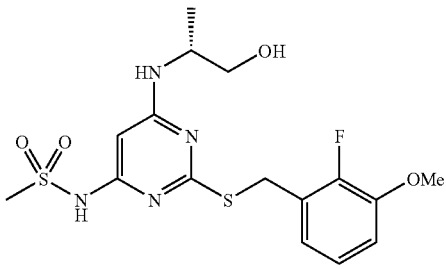

The title compound was prepared as a white foam by the method of Example 40 using the subtitle product of step vii) (0.24 g) and trifluoroacetic acid (1.0 ml). Yield: 0.11 g.

MS APCI(+ve) 417 [M+H]⁺

¹H NMR δ_(DMSO) 7.24 (1H, bs), 7.06 (3H, m), 5.77 (1H, s), 4.70 (1H, bt), 4.33 (2H, t), 4.00 (1H, bs), 3.82 (3H, s), 3.40 (1H, m), 3.28 (1H, m), 3.20 (3H, s), 1.06 (3H, d).

The intermediates for this compound were prepared as follows:

i) 2-Fluoro-3-methoxybenzoic acid

Pentamethylenediethylenetetramine (31.2 ml) was added to a solution of 2-fluoroanisole (15.0 g) in THF (450 ml). The reaction mixture was cooled to −78° C. and n-butyllithium (59.6 ml, 2.5M solution in hexanes) was added dropwise. Stirring was maintained for 2 h before the solution was added in a dropwise fashion to a flask containing solid carbon dioxide pellets. Upon complete addition (30 min) the mixture was allowed to warm to room temperature before removal of the volatiles in vacuo. The residue was dissolved in 10% sodium hydroxide solution (300 ml) and extracted with Et₂O (3×). The aqueous was acidified to pH 1 with concentrated hydrochloric acid before extracting with DCM. The organics were washed with H₂O, dried (MgSO₄) and concentrated in vacuo to afford the subtitle compound as a yellow solid. Yield: 7.1 g.

¹H NMR δ_(CDCl3) 7.50 (1H, m), 7.12 (2H, m), 3.91 (3H, s).

ii) (2-Fluoro-3-methoxyphenyl)methanol

Lithium aluminium hydride (83.5 ml, 1M solution in THF) was added dropwise to a suspension of the subtitle product of step i) (7.1 g) in Et₂O (180 ml) at a rate that maintained gentle reflux. Upon complete addition the reaction was stirred for 1.5 h. 15% sodium hydroxide solution was added dropwise until no effervescence was observed. The resulting white precipitate was filtered and the filtrate diluted with H₂O (100 ml). The organics were removed in vacuo and the residue extracted with Et₂O (100 ml). The organics were washed with 2M sodium hydroxide solution (150 ml), H₂O (150 ml), brine (150 ml), dried (MgSO₄) and concentrated in vacuo to afford the subtitle compound as a white crystalline solid. Yield: 5.5 g.

¹H NMR δ_(CDCl3) 7.00 (3H, m), 4.77 (2H, d), 3.89 (3H, s), 1.77 (1H, t).

iii) 1-(Bromomethyl)-2-fluoro-3-methoxybenzene

Triphenylphosphine (11.1 g) was added to a solution of the subtitle product of step ii) (5.0 g) in DCM (200 ml) followed by the portionwise addition of carbon tetrabromide (14.0 g). The reaction was stirred for 4 h before the addition of further triphenylphosphine (2.0 g) and carbon tetrabromide (2.0 g) and stirring maintained for 1 h. The mixture was concentrated to 30 ml volume and diluted in Et₂O (300 ml). The solid precipitate was filtered and washed with Et₂O (3×) and the filtrate concentrated in vacuo. The residue was purified by column chromatography (10% Et₂O/iso-hexane) to afford the subtitle compound as a clear oil. Yield: 5.2 g.

¹H NMR δ_(CDCl3) 7.05 (1H, m), 6.93 (2H, m), 4.52 (2H, s), 3.89 (3H, s).

iv) 2-[(2-Fluoro-3-methoxybenzyl)thio]pyrimidine-4,6-diol

The subtitle compound was prepared as a white solid by the method of Example 39 step i) using 1-(bromomethyl)-2-fluoro-3-methoxybenzene (4.5 g), 2-mercaptopyrimidine-4,6-diol (2.96 g) and potassium hydroxide (1.15 g). Yield: 5.0 g.

¹H NMR δ_(DMSO) 7.10 (3H, m), 5.21 (1H, bs), 4.38 (2H, s), 3.83 (3H, s).

v) 4,6-Dichloro-2-[(2-fluoro-3-methoxybenzyl)thio]pyrimidine

The subtitle compound was prepared as a white solid by the method of Example 39 step ii) using the subtitle product of step iv) (4.91 g), phosphorus oxychloride (42.6 ml) and N,N-dimethylaniline (4.9 ml). Yield: 4.1 g.

¹H NMR δ(DMSO) 7.74 (1H, s), 7.09 (3H, m), 4.43 (2H, s), 3.83 (3H, s).

vi) N-{6-Chloro-2-[(2-fluoro-3-methoxybenzyl)thio]pyrimidin-4-yl}-N-{[2-(trimethylsilyl)ethoxy]methyl}methanesulfonamide The subtitle compound was prepared as a colourless oil by the method of Example 39 step iii) using the subtitle product of step v) (2.0 g), methanesulfonamide (0.60 g), 60% sodium hydride (0.50 g) and 2-(trimethylsilyl)ethoxymethyl chloride (1.11 ml). Yield: 2.42 g.
MS APCI(+ve) 509 [M+H]⁺ vii) N-{6-Chloro-2-[(2-fluoro-3-methoxybenzyl)thio]pyrimidin-4-yl}-N-{[2-(trimethylsilyl)ethoxy]methyl}methanesulfonamide A solution of the subtitle product of step vi) (0.3 g) in (R)-alaninol (1.5 ml) was stirred at 90° C. for 2.5 h. The reaction mixture was diluted in EtOAc (50 ml) and washed with water, brine, dried (MgSO₄) and concentrated in vacuo. The residue was purified by column chromatography (50% EtOAc/iso-hexane) to afford the subtitle compound as a gum. Yield: 0.24 g.
MS APCI(+ve) 547 [M+H]⁺

EXAMPLE 121

N-(2-[(2-Fluoro-3-methoxybenzyl)thio]-6-{[(1R)-1-(hydroxymethyl)propyl]amino}-pyrimidin-4-yl)methanesulfonamide

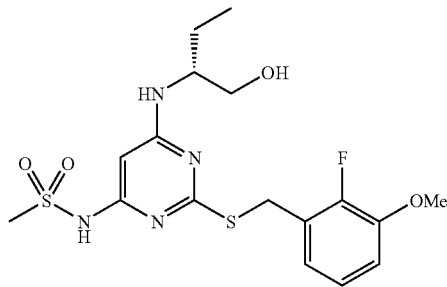

The title compound was prepared as a white foam by the method of Example 40 using the subtitle product of step i) (0.24 g) and trifluoroacetic acid (1.0 ml). Yield: 0.11 g.
MS APCI(+ve) 431 [M+H]⁺
¹H NMR δ(DMSO) 7.10 (1H, bs), 7.06 (3H, m), 5.80 (1H, bs), 4.64 (1H, bs), 4.30 (2H, t), 3.85 (1H, bs), 3.82 (3H, s), 3.39 (1H, bm), 3.20 (3H, bs), 1.61 (1H, p), 1.36 (1H, p), 0.83 (3H, t).
The intermediates for this compound were prepared as follows:

i) N-(2-[(2-Fluoro-3-methoxy-benzyl)thio]-{6-{[(1R)-1-(hydroxymethyl)propyl]amino}-pyrimidin-4-yl)-N-{[2-(trimethylsilyl)ethoxy]methyl}methanesulfonamide A solution of the subtitle compound of Example 120 step vi) (0.3 g) in (2R)-2-aminobutan-1-ol (1.5 ml) was stirred at 90° C. for 2.5 h. The reaction mixture was diluted in EtOAc (50 ml) and washed with H₂O and brine, dried (MgSO₄) and concentrated in vacuo. The residue was purified by column chromatography (50% EtOAc/iso-hexane) to afford the subtitle compound as a gum. Yield: 0.26 g.
MS APCI(+ve) 561 [M+H]⁺

EXAMPLE 122

N-{6-{[(1R)-2-Hydroxy-1-methylethyl]amino}-2-[(3-methoxy-2-methylbenzyl)thio]-pyrimidin-4-yl}-1,2-dimethyl-1H-imidazole-4-sulfonamide

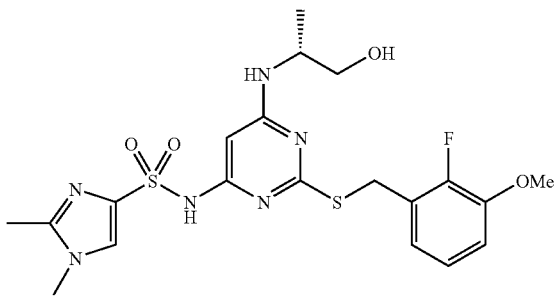

A solution of the subtitle compound of step i) (0.4 g) and (R)-alaninol (0.11 ml) in NMP (1.0 ml) was stirred at 90° C. for 2 h. Upon cooling the reaction mixture was diluted with acetonitrile (4 ml) and 2M hydrochloric acid (1 ml) and stirring main wined for 10 min. The solvent was partially evaporated under reduced pressure and the reaction mixture diluted in EtOAc (50 ml) and washed with H₂O (5 ml), dried (MgSO₄) and concentrated in vacuo to afford a yellow oil. The residue was purified by reverse phase HPLC (gradient 90% to 5% 0.02M ammonium hydroxide/acetonitrile) to yield the title compound as a white solid. Yield: 12 mg.
MS APCI(+ve) 497 [M+H]⁺
¹H NMR δ(DMSO) 7.70 (1H, bs), 7.03 (4H, m), 5.88 (1H, bs), 4.69 (2H, bs), 3.90 (1H, bs), 3.54 (3H, s), 3.37 (1H, m), 3.28 (3H, s), 3.25 (1H, m), 2.26 (3H, s), 1.03 (3H, d).
The intermediates for this compound were prepared as follows:

i) N-{6-Chloro-2-[(3-methoxy-2-methylbenzyl)thio]pyrimidin-4-yl}-1,2-dimethyl-N-{[2-(trimethylsilyl)ethoxy]methyl}-1H-imidazole-4-sulfonamide The subtitle compound was prepared as a colourless oil by the method of Example 39 step iii) using the subtitle product of Example 120 step v) (2.3 g), 1,2-dimethyl-1H-imidazole-4-sulfonamide (0.60 g), 60% sodium hydride (0.87 g) and 2-(trimethylsilyl)ethoxymethyl chloride (1.5 ml). Yield: 2.2 g.
MS APCI(+ve) 646 [M+H]⁺

EXAMPLE 123

N-{6-[(2-Hydroxy-1,1-dimethylethyl)amino]-2-[(3-methoxy-2-methylbenzyl)thio]pyrimidin-4-yl}-1,2-dimethyl-1H-imidazole-4-sulfonamide

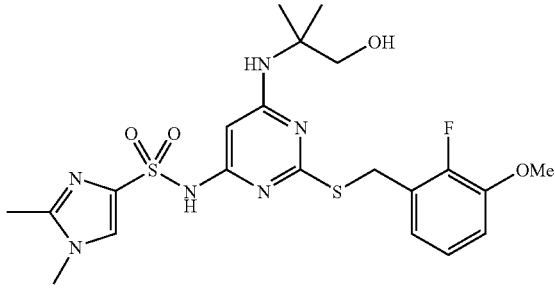

The title compound was prepared as a white solid by the method of Example 122 using the subtitle product of Example 122 step i) (0.40 g) and 2-amino-2-methylpropan-1-ol (0.20 ml) then 2M hydrochloric acid (1.0 ml). Yield: 13 mg.

MS APCI(+ve) 511 [M+H]$^+$ $^1$H NMR $\delta_{(DMSO)}$ 7.28 (1H, bs), 7.04 (3H, m), 5.23 (1H, bs), 5.72 (1H, s), 4.23 (2H, s), 3.82 (3H, s), 3.52 (3H, s), 3.35 (2H, bs), 2.25 (3H, s), 1.18 (6H, s).

EXAMPLE 124

N-{6-{[(1R)-1-(Hydroxymethyl)propyl]amino}-2-[(3-methoxy-2-methylbenzyl)thio]pyrimidin-4-yl}-1,2-dimethyl-1H-imidazole-4-sulfonamide

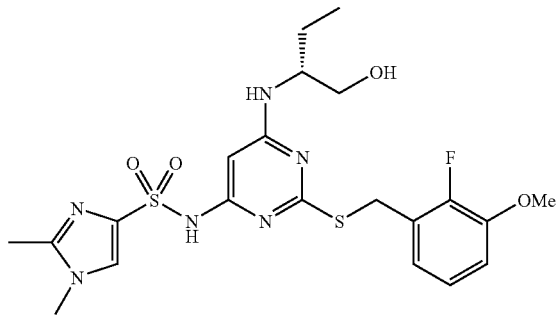

The title compound was prepared as a white solid by the method of Example 122 using the subtitle product of Example 122 step i) (0.40 g), and (R)-2-aminobutanol (0.19 ml) then 2M hydrochloric acid (1.0 ml). Yield: 46 mg.

MS APCI(+ve) 511 [M+H]$^+$ $^1$H NMR $\delta_{(DMSO)}$ 7.72 (1H, bs), 7.03 (1H, bs), 7.00 (3H, bs), 5.92 (1H, bs), 4.62 (1H, bs), 4.26 (2H, s), 3.82 (4H, bs+s), 3.54 (3H, s), 3.36 (1H, m), 2.27 (3H, s), 1.57 (1H, m), 1.35 (1H, m), 0.81 (3H, t).

EXAMPLE 125

N-(2-(Benzylthio)-6-{[(1R)-2-hydroxy-1-methylethyl]amino}pyrimidin-4-yl)-1,1,1-trifluoromethanesulfonamide

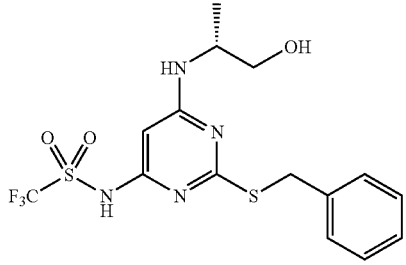

Triflic anhydride (0.38 ml) was added dropwise to a solution of the subtitle product of Example 3 step ii) (0.4 g) and N,N-diisopropylethylamine (1.7 ml) in DCM at −10° C. After 15 min saturated sodium bicarbonate (10 ml) was added and the organics recovered through extraction with DCM (2×10 ml). The organics were combined, washed with H$_2$O, brine, dried (MgSO$_4$) and concentrated in vacuo. The residue was dissolved in THF (10 ml) and treated with tetrabutylammonium fluoride (5 ml, 1M in THF) for 15 mins before acidifying to pH 1 with 1M hydrochloric acid. EtOAc (10 ml) was added before the organics were washed with brine, dried (MgSO$_4$) and concentrated in vacuo. The residue was purified by column chromatography (2% methanol/DCM) to afford a gum which was freeze dried from dioxane (20 ml) to yield title compound as a foam. Yield: 0.37 g.

MS APCI(+ve) 422 [M+H]$^+$ $^1$H NMR $\delta_{(DMSO)}$ 13.30 (1H, s), 8.44 (1H, d), 7.42 (2H, d), 7.37-7.24 (3H, m), 6.20 (1H, s), 4.48-4.41 (2H, m), 4.28-4.16 (1H, m), 3.46-3.28 (2H, m), 1.09 (3H, d).

EXAMPLE 126

N-(2-(Benzylthio)-5-chloro-6-{[(1R)-2-hydroxy-1-methylethyl]amino}pyrimidin-4-yl)methanesulfonamide

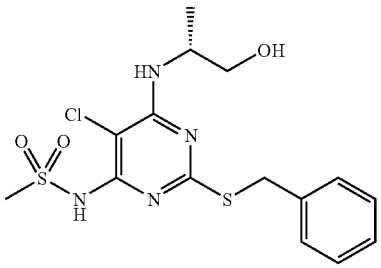

The title compound of Example 3 (0.4 g) was dissolved in DCM (20 ml) and treated with N-chlorosuccinimide (0.14 g) for 2 h. The volatiles were removed in vacuo and the residue purified by reverse phase HPLC ((gradient 95% to 20% 0.02M ammonium hydroxide/acetonitrile) to yield the title compound as a white solid. Yield: 0.25 g.

MS APCI(−ve) 402 [M−H]$^+$ $^1$H NMR $\delta_{(DMSO)}$ 10.33 (1H, s), 7.41 (2H, d), 7.35-7.20 (3H, m), 6.76 (1H, d), 4.79 (1H, t), 4.39-4.29 (2H, m), 4.28-4.16 (1H, m), 3.50-3.31 (2H, m), 1.12 (3H, d).

EXAMPLE 127

N-(2-(Benzylthio)-6-{[(1R)-2-hydroxy-1-methylethyl]amino}pyrimidin-4-yl)-2-chlorobenzenesulfonamide

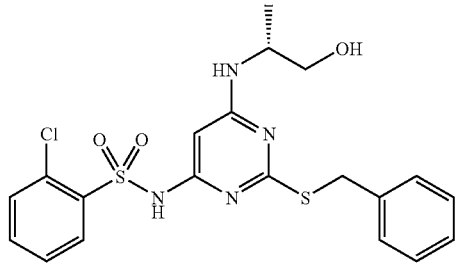

2-Chlorophenylmethanesulfonyl chloride (0.17 g) was added to a solution of the subtitle product of Example 3 step ii) (66 mg) in pyridine (2 ml) and N,N-dimethylaminopyridine (24 mg). The reaction mixture was stirred for 18 h. The volatiles were removed under reduced pressure and the residue diluted in THF (5 ml) and treated with 2M hydrochloric acid (5 ml) for 5 min. The solvent was evaporated and the residue partitioned between DCM and treated with saturated sodium bicarbonate to pH neutral. The organic layer was washed with H$_2$O and brine. The organics were dried (MgSO$_4$) and concentrated to yield a solid. This material was purified by column chromatography (20% EtOAc/DCM) to yield the title compound as an orange solid. Yield: 19 mg.

MS APCI(+ve) 464 [M+H]$^+$ $^1$H NMR $\delta_{(DMSO)}$ 10.88 (1H, s), 8.07 (1H, d), 7.66 (2H, m), 7.56 (1H, m), 7.27 (5H, m), 6.45 (1H, bd), 6.09 (1H, s), 5.91 (1H, s), 4.24 (2H, q), 3.85 (1H, bt), 3.30 (2H, m), 1.02 (3H, d).

EXAMPLE 128

N-(2-[(3,4-Difluorobenzyl)thio]-6-{[(1R)-2-hydroxy-1-methylethyl]amino}pyrimidin-4-yl)methanesulfonamide

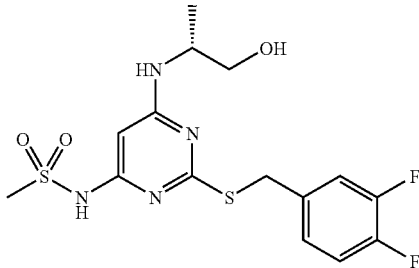

The title compound was prepared by the method of Example 27 using the subtitle product of step iii) (0.3 g) and methanesulfonyl chloride (0.16 ml). Yield: 77 mg.

MS APCI(+ve) 405 [M+H]$^+$ $^1$H NMR $\delta_{(DMSO)}$ 7.51 (1H, m), 7.33 (2H, m), 5.78 (1H, s), 4.70 (1H, bs), 4.30 (2H, q), 3.95 (1H, bs), 3.33 (2H, m), 3.20 (3H, s), 1.05 (3H, d).

The intermediates for the above compound were prepared as follows:

i)
6-Amino-2-[(3,4-difluorobenzyl)thio]pyrimidin-4-ol

The subtitle compound was prepared according to the procedure of Example 1 step 1) treating 4-amino-6-hydroxy-2-mercaptopyrimidine monohydrate (2.0 g) with 3,4-difluorobenzyl bromide (2.66 g) to afford the subtitle compound as a white solid. Yield: 3.35 g. $^1$H NMR. $\delta_{(DMSO)}$ 7.54 (1H, m), 7.32 (2H, m), 6.58 (2H, bs), 4.96 (1H, bs), 4.29 (2H, s).

ii) 6-Chloro-2-[(3,4-difluorobenzyl)thio]pyrimidin-4-amine

The subtitle compound was prepared from the product of step i) (3.35 g) according to the procedure of Example 1 step ii) to afford the subtitle product as a green foam which was used directly in the subsequent step.

MS: APCI(+ve) 368 [M+H]$^+$ iii) N-((1R)-2-{[tert-Butyl(dimethyl)silyl]oxy}-1-methylethyl)-2-[(3,4-difluorobenzyl)-thio]pyrimidine-4,6-diamine N,N-Diisopropylethylamine (4.9 ml) was added to a solution of (R)-alaninol (5.0 ml) and the subtitle product of step ii) and stirred at 120° C. for 7 days before partitioning between H$_2$O and DCM. The organics were washed with H$_2$O, brine, dried (MgSO$_4$) and concentrated in vacuo to afford a residue which was purified by column chromatography (8:1 EtOAc/iso-hexane). The residue was treated with imidazole (0.29 g) and a solution of ten-butyldimethylsilyl chloride (0.63 g) in DMF (1.5 ml) and stirring maintained for 18 h. The reaction mixture was partitioned between EtOAc and H$_2$O and the organics recovered, dried (MgSO$_4$) and concentrated in vacuo. The residue was purified by column chromatography (6:4 Et$_2$O/iso-hexane) to afford the subtitle compound as an orange gum. Yield: 0.61 g.

MS: APCI(+ve) 441 [M+H]$^+$

EXAMPLE 129

N-(2-(Benzylthio)-6-{[(1R)-2-hydroxy-1-methylethyl]amino}pyrimidin-4-yl)-1,2,3,4-tetrahydroisoquinoline-7-sulfonamide

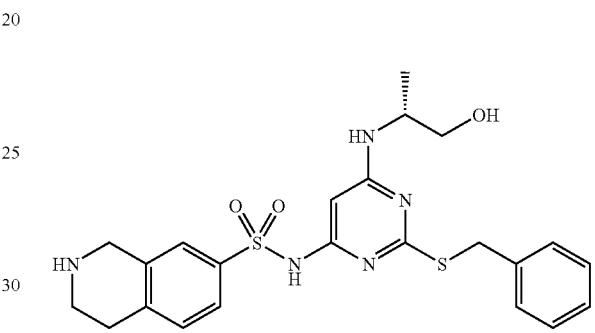

The title compound was prepared by the method of Example 127 using the subtitle product of Example 3 step ii) (0.2 g) and 2-(trifluoroacetyl)-1,2,3,4-tetrahydroisoquinoline-7-sulfonyl chloride (0.49 g). Yield: 84 mg.

MS APCI(+ve) 486 [M+H]$^+$ $^1$H NMR $\delta_{(DMSO/D2O)}$ 7.59 (1H, d) 7.55 (1H, s), 7.27 (6H, m), 5.65 (1H, s), 4.17 (2H, t), 4.01 (2H, s), 3.81 (1H, bs), 3.37 (1H, m), 3.24 (1H, m), 3.09 (2H, t), 2.84 (2H, t), 1.03 (3H, d).

EXAMPLE 130

5-{[(2-(Benzylthio)-6-{[(1R)-2-hydroxy-1-methylethyl]amino}pyrimidin-4-yl)amino]sulfonyl}-2-furoic acid

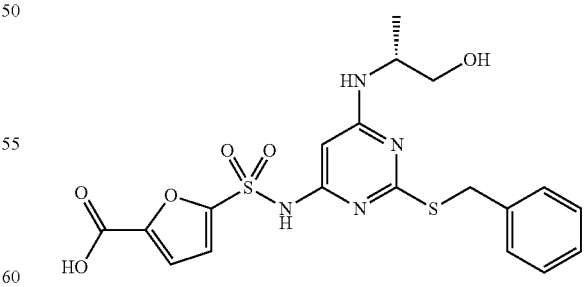

Hydrogen chloride (2 ml, 4M in dioxan) was added to the subtitle product of step ii) (30 mg) and stirred for 2 h. The volatiles were removed in vacuo and the residue purified by reverse phase HPLC (gradient 95% to 50% 0.02M ammonium hydroxide/acetonitrile) to yield the title compound as a white solid. Yield: 20 mg.

MS APCI(+ve) 436 [M+H]$^+$ $^1$H NMR δ$_{(DMSO)}$ 7.40 (2H, d), 7.30 (3H, m), 6.97 (1H, d), 6.91 (1H, d), 5.85 (1H, s), 4.34 (2H, q), 4.02 (1H, bs), 3.39 (1H, m), 3.30 (1H, m), 1.07 (3H, d).

The intermediates for this compound were prepared as follows:

i) Methyl 5-[({2-(benzylthio)-6-[((1R)-2-{[tert-butyl(dimethyl)silyl]oxy}-1-methylethyl)amino]pyrimidin-4-yl}amino)sulfonyl]-2-furoate Methyl 5-(chlorosulfonyl)-2-furoate (0.54 g) was added to the solution of the subtitle product of Example 3 step ii) (0.5 g) in pyridine (15 ml) and N,N-dimethylaminopyridine (0.15 g). The reaction mixture was stirred for 18 h. A further aliquot of the sulfonyl chloride (0.27 g) was added and stirring maintained for a further 18 h. The solvent was evaporated and the residue purified by column chromatography (25% EtOAc/iso-hexane) to yield the subtitle compound as a yellow glass. Yield: 0.24 g.

$^1$H NMR δ$_{(DMSO)}$ 7.38 (7H, m), 7.09 (1H, bs), 5.95 (1H, s), 4.42 (2H, s), 4.26 (1H, bs), 3.87 (3H, s), 3.54 (2H, bm), 1.12 (3H, d), 0.85 (9H, s), 0.01 (6H, m).

ii) 5-[({2-(Benzylthio)-6-[((1R)-2-{[tert-butyl(dimethyl)silyl]oxy}-1-methylethyl)amino]pyrimidin-4-yl}amino)sulfonyl]-2-furoic acid Lithium hydroxide (33 mg) was added to a solution of the subtitle product of step i) (0.23 g) in THF/H$_2$O (1 ml/1 ml) and stirring maintained for 1 h. The THF was removed in vacuo and the residue neutralised with AcOH before extracting with EtOAc. The organics were then washed with H$_2$O, dried (MgSO$_4$) and concentrated in vacuo. The residue was purified by reverse phase HPLC (gradient 95% to 20% 0.02M ammonium hydroxide/acetonitrile) to yield the title compound as an off-white solid. Yield: 0.14 g.

$^1$H NMR δ$_{(DMSO)}$ 7.13 (6H, m), 6.84 (2H, d), 5.72 (1H, s), 4.26 (2H, s), 3.93 (1H, bs), 3.58 (1H, m), 3.34 (1H, m), 1.07 (3H, d), 0.84 (9H, s), 0.00 (6H, s).

EXAMPLE 131

N-(2-(Benzylthio)-6-{[(1R)-2-hydroxy-1-methylethyl]amino}pyrimidin-4-yl)-5-(piperazin-1-ylcarbonyl)furan-2-sulfonamide

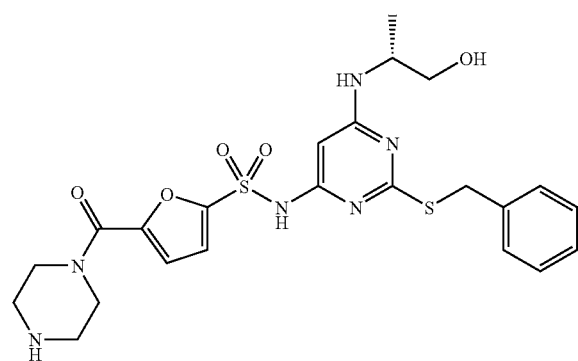

Hydrogen chloride (2 ml, 4M in dioxan) was added to the subtitle product of step i) (0.12 g) and stirred for 2 h. The volatiles were removed in vacuo and the residue purified by reverse phase HPLC (gradient 95% to 50% 0.02M ammonium hydroxide/acetonitrile) to yield the title compound as a white solid. Yield: 68 mg.

MS APCI(+ve) 533 [M+H]$^+$ $^1$H NMR δ$_{(DMSO)}$ 7.35 (2H, d), 7.24 (3H, m), 7.02 (1H, d), 6.86 (1H, d), 5.68 (1H, s), 4.21 (2H, t), 3.84 (1H, bs), 3.73 (4H, bs), 3.38 (1H, m), 3.25 (1H, m), 3.01 (4H, bs), 1.05 (3H, d).

The intermediates for this compound were prepared as follows:

i) tert-Butyl 4-[({2-(benzylthio)-6-[((1R)-2-{[tert-butyl(dimethyl)silyl]oxy}-1-methyl-ethyl)amino]-pyrimidin-4-yl}amino)sulfonyl]piperazine-1-carboxylate tert-Butylpiperazine-1-carboxylate (45 mg), N-hydroxybenzotriazole (33 mg), and then dicyclohexylcarbodiimide (50 mg) were added to a solution of the subtitle product of Example 130 step (0.14 g) in DCM (5 ml). After 1 h the reaction was filtered and washed well with DCM. The combined filtrates were washed with brine, dried (MgSO$_4$) and concentrated in vacuo. The residue was purified by column chromatography (40% EtOAc/iso-hexane) to yield the subtitle compound as a white solid. Yield: 0.17 g.

MS APCI(+ve) 747 [M+H]$^+$

EXAMPLE 132

5-{[(2-(Benzylthio)-6-{[(1R)-2-hydroxy-1-methylethyl]amino}pyrimidin-4-yl)amino]sulfonyl}-N,N-dimethyl-2-furamide

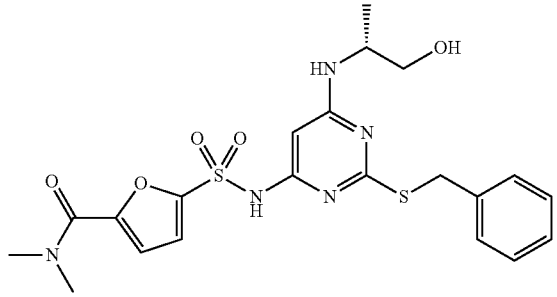

2M Hydrochloric acid (10 ml) was added to a solution of the subtitle product of step i) (0.20 g) in THF (10 ml) and stirred for 3 h. The volatiles were removed in vacuo and the residue was extracted with DCM. The organics were washed with brine, dried (MgSO$_4$) and concentrated in vacuo. The residue was purified by reverse phase HPLC (gradient 95% to 50% 0.02M ammonium hydroxide/acetonitrile) to yield the title compound as a white solid. Yield: 31 mg.

MS APCI(–ve) 490 [M–H]$^-$ $^1$H NMR δ$_{(DMSO)}$ 7.39 (2H, d), 7.28 (3H, m), 7.05 (2H, bs), 5.93 (1H, bs), 4.78 (1H, bs), 4.35 (2H, bs), 4.13 (1H, bs), 3.40 (2H, m), 3.09 (3H, bs), 2.95 (3H, bs), 1.07 (3H, d).

The intermediates for this compound were prepared as follows:

i) 5-[({2-(Benzylthio)-6-[((1R)-2-{[tert-butyl(dimethyl)silyl]oxy}-1-methylethyl)amino]-pyrimidin-4-yl}amino)sulfonyl]-N,N-dimethyl-2-furamide A solution of the subtitle product of Example 130 step i) (0.37 g) in 40% aqueous dimethylamine (4.21 ml) was stirred for 18 h. The volatiles were removed in vacuo and the residue extracted with EtOAc. The organics were washed with brine, dried (MgSO₄) and concentrated in vacuo. The residue purified by column chromatography (50% EtOAc/iso-hexane) to yield the subtitle compound as a yellow gum. Yield: 0.14 g.
MS APCI(+ve) 606 [M+H]⁺

EXAMPLE 133

N-(2-[(3-Chloro-2-fluorobenzyl)thio]-6-{[(1R)-2-hydroxy-1-methylethyl]amino}pyrimidin-4-yl)-cis-3,5-dimethylpiperazine-1-sulfonamide

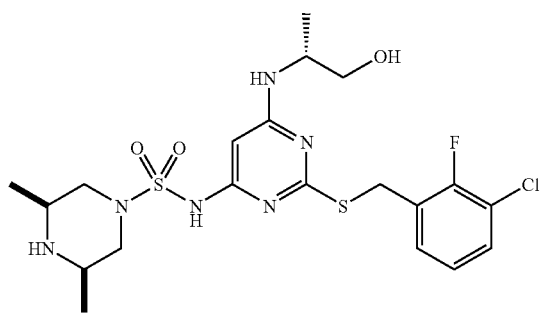

The title compound was prepared as a white solid by the method of Example 39 using the subtitle product of step ii) (0.37 g), and (R)-alaninol (1 ml). Yield: 6 mg.
MS APCI(+ve) 519 [M+H]⁺
¹H NMR δ$_{(DMSO)}$ 7.59 (1H, t), 7.47 (1H, p), 7.15 (1H, s), 5.80 (1H, s), 4.67 (1H, t), 4.35 (2H, s), 3.90 (1H, bs), 3.57 (2H, s), 3.38 (4H, m), 2.24 (2H, t), 1.04 (3H, d), 0.94 (6H, d).

The intermediates for this compound were prepared as follows:

i) cis-3,5-dimethylpiperazine-1-sulfonamide

A solution of cis-2,6-dimethylpiperazine (5.0 g) and sulfamide (10.0 g) in 1,4-dioxane (100 ml) was stirred for 72 h at 110° C. The volatiles were removed in vacuo and the residue suspended in EtOAc. The filtrate was evaporated to a yellow solid (4.3 g). 1 g of this material was dissolved in methanol and applied to an SCX cartridge (10 g). The cartridge was washed with 50% aqueous methanol (200 ml) before the subtitle product was eluted with 5% ammonium hydroxide solution/methanol (200 ml). The solvent was removed under reduced pressure to yield the subtitle compound as a yellow solid. Yield: 0.46 g.
MS APCI(+ve) 194 [M+H]⁺ ii) N-(6-chloro-2-[(3-chloro-2-fluorobenzyl)thio]-pyrimidin-4-yl)-cis-3,5-dimethyl-piperazine-1-sulfonamide 60% Sodium hydride (0.19 g) was added to a stirred solution of the subtitle product of step i) (0.45 g) in DMF (4.2 ml) at 0° C. The cooling bath was removed for 15 min before recooling to 0° C. and addition of a solution of the subtitle product of Example 31 step (0.76 g) in DMF (2 ml). After stirring at room temperature for 3 h the mixture was acidified with 2M hydrochloric acid to pH 4 and the volatiles were removed in vacuo. The residue was dissolved in methanol and applied to an SCX cartridge (10 g). The cartridge was washed with methanol (200 ml) before the subtitle product was eluted with 10% triethylamine/methanol (300 ml). The solvent was removed under reduced pressure and the residue triturated from Et₂O to yield the subtitle compound as a yellow solid. Yield: 0.37 g.
MS APCI(+ve) 480/482/484 [M+H]⁺

EXAMPLE 134

N-(2-[(3-Chloro-2-fluorobenzyl)thio]-6-{[(1R)-2-hydroxy-1-methylethyl]amino}pyrimidin-4-yl)-4-ethylpiperazine-1-sulfonamide

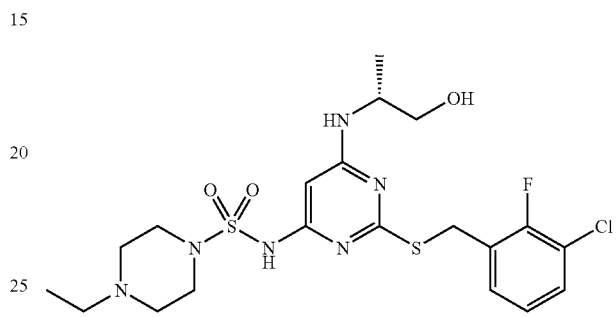

A solution of the subtitle product of step ii) (1.92 g) in (R)-alaninol (5 ml) was heated at 80° C. for 72 h. The reaction mixture was then diluted in methanol and purified by reverse phase HPLC (gradient 95% to 60% 0.02M ammonium hydroxide/acetonitrile) to yield the title compound as a yellow glass. Yield: 90 mg.
MS APCI(+ve) 519 [M+H]⁺
¹H NMR δ$_{(DMSO)}$ 7.59 (1H, t), 7.47 (1H, t), 7.16 (2H, bt), 5.86 (1H, s), 4.69 (1H, bm), 4.36 (2H, t), 3.91 (1H, vbs), 3.38 (2H, m), 3.12 (4H, bs), 2.28 (6H, m), 1.05 (3H, d), 0.96 (3H, t).

The intermediates for this compound were prepared as follows:

i) 4-Ethylpiperazine-1-sulfonamide

A solution of N-ethylpiperazine (5.0 g) and sulfamide (10.0 g) in 1,4-dioxane (100 ml) was stirred for 72 h at 110° C. The volatiles were removed in vacuo and 5 g of the residue was dissolved in methanol and applied to an SCX cartridge (70 g). The cartridge was washed with 50% aqueous methanol (200 ml) before the subtitle product was eluted with 10% triethylamine/methanol (100 ml) The solvent was removed under reduced pressure to yield the subtitle compound as a pale beige solid. Yield: 3.0 g.
MS APCI(-ve) 192 [M-H]⁺ ii) N-{6-Chloro-2-[(3-chloro-2-fluorobenzyl)thio]pyrimidin-4-yl}-4-ethylpiperazine-1-sulfonamide The subtitle compound was prepared as an orange gum by the method of Example 133 step ii) using the subtitle product of step i) (3.0 g), 60% sodium hydride (1.24 g) and the subtitle product of Example 31 step iii) (5.0 g). Yield: 0.73 g.
MS APCI(+ve) 480 [M+H]⁺

EXAMPLE 135

N-{2-[(3-Chloro-2-fluorobenzyl)thio]-6-[(2-hydroxy-1,1-dimethylethyl)amino]-pyrimidin-4-yl}-cis-3,5-dimethylpiperazine-1-sulfonamide

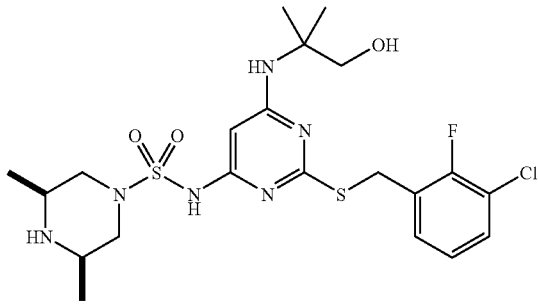

A solution of the subtitle product of step i) (0.26 g) in 2-amino-2-methylpropanol (1 ml) was heated at 90° C. for 3.5 h and then 55° C. for 72 h. The reaction mixture was then diluted in EtOAc and washed with H₂O, dried (Na₂SO₄) and concentrated in vacuo. The residue was diluted in trifluoroacetic acid (2 ml) and stirred for 15 min before removal of the volatiles in vacuo and azeotroping the residue with toluene (2×). The crude material and purified by reverse phase HPLC (gradient 95% to 50% 0.02M ammonium hydroxide/acetonitrile) to yield the title compound as a solid. Yield: 48 mg.

MS APCI(+ve) 533 [M+H]⁺

¹H NMR δ$_{(DMSO)}$ 7.58 (1H, t), 7.47 (1H, t), 7.17 (1H, t), 5.88 (1H, s), 4.36 (2H, s), 3.46 (4H, m), 2.73 (2H, bs), 2.30 (2H, t), 1.21 (6H, s), 0.97 (6H, d).

The intermediates for this compound were prepared as follows:

i) N-{6-Chloro-2-[(3-chloro-2-fluorobenzyl)thio]pyrimidin-4-yl}-cis-3,5-dimethyl-N-{[2-(trimethylsilyl)ethoxy]methyl}piperazine-1-sulfonamide The subtitle compound was prepared as a yellow gum by the method of Example 39 step using the subtitle product of Example 133 step i) (2.6 g), the subtitle product of Example 31 step iii) (4.35 g), 60% sodium hydride (0.99 g) and 2-(trimethylsilyl)ethoxymethyl chloride (2.38 ml). Yield: 3.4 g.

MS APCI(+ve) 610 [M+H]⁺

EXAMPLE 136

N-{6-{[(1R)-2-Hydroxy-1-methylethyl]amino}-2-(R,S)-[(1-phenylethyl)thio]pyrimidin-4-yl}methanesulfonamide

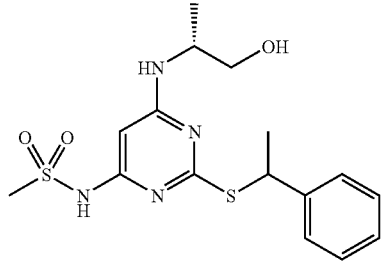

Methanesulfonyl chloride (0.16 ml) was added to a stirred solution of the subtitle product of step ii) (0.29 g) and N,N-diisopropylethylamine (0.36 ml) in DCM (5 ml). After stirring for 18 h the volatiles were removed under reduced pressure and the residue diluted in THF (8 ml) and treated with 1M sodium hydroxide solution (4.2 ml). After 6 h 2M hydrochloric acid was added to pH 1 and stirring maintained for 3 days. The reaction mixture was then neutralised with saturated sodium bicarbonate solution and the product extracted with DCM. The organics were washed with H₂O, dried (Na₂SO₄) and concentrated in vacuo. The residue was purified by reverse phase HPLC (gradient 95% to 25% 0.02M ammonium hydroxide/acetonitrile) to yield the title compound as a white solid. Yield: 90 mg.

MS APCI(+ve) 383 [M+H]⁺

¹H NMR δ$_{(DMSO)}$ 7.45 (2H, d), 7.33 (2H, t), 7.24 (1H, m), 5.77 (1H, bs), 4.93 (1H, q), 4.71 (1H, bs), 3.41 (1H, m), 3.30 (1H, m), 3.23 (3H, bs), 1.67 (3H, dd), 1.07 (3H, dd).

The intermediates for the title compound were prepared as follows:

i) 6-Amino-2-[(1-phenylethyl)thio]pyrimidin-4-ol

The subtitle compound was prepared according to the procedure of Example 1 step i) treating 4-amino-6-hydroxy-2-mercaptopyrimidine monohydrate (5.0 g) with ☐-methylbenzyl bromide (5.74 g) to afford the subtitle compound which was used directly in the subsequent step.

MS APCI(+ve) 352 [M+H]⁺ ii) N-((1R)-2-{[tert-butyl(dimethyl)silyl]oxy}-1-methylethyl)-2-(R,S)-[(1-phenylethyl)thio]-pyrimidine-4,6-diamine The subtitle compound was prepared from the product of step i) according to the procedure of Example 1 step ii) to afford the subtitle product as a green foam which was then diluted in (R)-alaninol (12.2 ml), N,N-diisopropylethylamine (11.8 ml) and NMP (16 ml) and stirred at 130° C. for 3 days before partitioning between H₂O and DCM. The organics were washed with H₂O, dried (MgSO₄) and concentrated in vacuo to afford a residue which was purified by column chromatography (8:2 EtOAc/iso-hexane). The residue was treated with imidazole (2.7 g) and a solution of tert-butyldimethylsilyl chloride (5.95 g) in DMF (30 ml) and stirring maintained for 18 h. The reaction mixture was partitioned between EtOAc and H₂O and the organics recovered, dried (MgSO₄) and concentrated in vacuo. The residue was purified by column chromatography (6:4 Et₂O/iso-hexane) to afford the subtitle compound as a gum. Yield: 1.3 g.

MS: APCI(+ve) 419 [M+H]⁺

EXAMPLE 137

N-{6-{[(1R)-2-hydroxy-1-methylethyl]amino}-2-[(2,3,4-trifluorobenzyl)thio]-pyrimidin-4-yl}methanesulfonamide

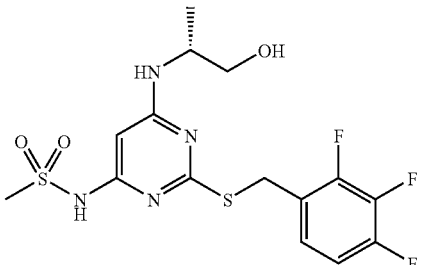

The title product was prepared from a solution of the product of Example 43 step iv) (4 ml) and quenching with 2,3,4- trifluorobenzyl bromide (0.5 g) using the method described for Example 43 to give the title compound as a white foam. Yield: 32 mg.

MS APCI(+ve) 423 [M+H]$^+$

EXAMPLE 138

N-[2-[[(3-Chloro-2-fluorophenyl)methyl]thio]-6-[(R)-(2-hydroxy-1-methylethyl)amino]-4-pyrimidinyl]-1-methyl-1H-imidazole-4-sulfonamide

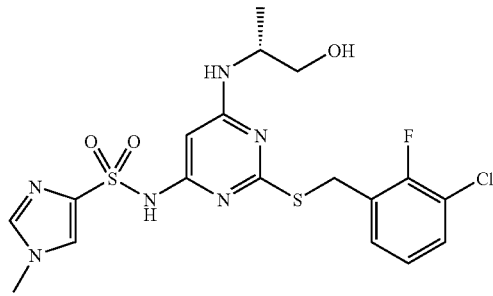

The title compound was prepared as a white solid by the method of Example 37 from the product of Example 27 step iii) (1.4 g) using 1-methyl-1H-imidazole-4-sulfonyl chloride (1.0 g). Purification was by column chromatography (DCM/methanol/AcOH 190:10:1). p Yield: 1.0 g.

MS APCI(+ve) 488 [M+H]$^+$ $^1$H NMR $\delta_{(DMSO)}$ 7.85 (1H, bs), 7.75 (1H, s), 7.50 (2H, m), 7.18 (1H, m), 5.91 (1H, m), 4.36 (2H, s), 3.60 (3H, s), 3.30 (2H, m), 1.10 (3H, d).

The invention claimed is:

1. A method for the treatment of a condition or disease selected from COPD, asthma, allergic rhinitis, and rheumatoid arthritis, comprising administering a compound of formula (1), or a pharmaceutically acceptable salt thereof, wherein:

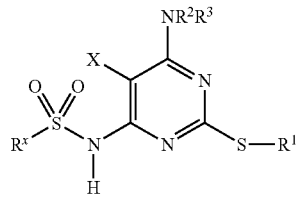

(1)

wherein $R^1$ is a group selected from $C_{3-7}$carbocyclyl, $C_{1-8}$alkyl, $C_{2-6}$alkenyl and $C_{2-6}$alkynyl; wherein the group is optionally substituted by 1, 2 or 3 substituents independently selected from fluoro, nitrile, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, phenyl or heteroaryl; wherein phenyl and heteroaryl are optionally substituted by 1, 2 or 3 substituents independently selected from halo, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, $C_{1-6}$alkyl and trifluoromethyl;

wherein $R^2$ is $C_{3-7}$carbocyclyl, optionally substituted by 1, 2 or 3 substituents independently selected from:

(a) fluoro, —OR$^4$, —NR$^5$R$^6$ —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$;

(b) a 3-8 membered ring optionally containing 1, 2 or 3 atoms selected from O, S, —NR$^8$ and whereby the ring is optionally substituted by $C_{1-3}$alkyl or fluoro; or (c) phenyl or heteroaryl, each of which is optionally substituted by 1, 2 or 3 substituents independently selected from halo, cyano, nitro, —OR$^4$, —NR$^5$R$^6$, —CONR$^5$R$^6$, —NR$^8$COR$^9$, —SO$_2$NR$^5$R$^6$, —NR$^8$SO$_2$R$^9$, $C_{1-6}$alkyl and trifluoromethyl;

or $R^2$ is a group selected from $C_{1-8}$alkyl, $C_{2-6}$alkenyl or $C_{2-6}$alkynyl wherein the group is substituted by 1, 2 or 3 substituents independently selected from hydroxy, amino, $C_{1-6}$alkoxy, $C_{1-6}$alkylamino, di($C_{1-6}$alkyl)amino, N—($C_{1-6}$alkyl)-N-(phenyl)amino, N—$C_{1-6}$alkylcarbamoyl, N,N -di($C_{1-6}$alkyl)carbamoyl, N—($C_{1-6}$alkyl)-N-(phenyl)carbamoyl, carboxy, phenoxycarbonyl, —NR$^8$COR$^9$, —SO$_2$R$^{10}$, —SO$_2$NR$^5$R$^6$ and —NR$^8$SO$_2$R$^9$;

wherein $R^3$ is hydrogen or independently $R^2$;

$R^4$ is hydrogen or a group selected from $C_{1-6}$alkyl and phenyl, wherein the group is optionally substituted by 1 or 2 substituents independently selected from halo, phenyl, —OR$^{11}$ and —NR$^{12}$R$^{13}$;

$R^5$ and $R^6$ are independently hydrogen or a group selected from $C_{1-6}$alkyl and phenyl wherein the group is optionally substituted by 1, 2 or 3 substituents independently selected from halo, phenyl, —OR$^{14}$, —NR$^{15}$R$^{16}$, —COOR$^{14}$, —CONR$^{15}$R$^{16}$, —NR$^{15}$COR$^{16}$, —SO2R$^{10}$, —SONR$^{15}$R$^{16}$, and NR$^{15}$SO$_2$R$^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring is optionally substituted by 1, 2 or 3 substituents independently selected from phenyl, —OR$^{14}$, —COOR$^{14}$, —NR$^{15}$R$^{16}$, —SO2R$^{10}$, —SONR$^{15}$R$^{16}$, NR$^{15}$SO$_2$R$^{16}$ or $C_{1-6}$alkyl (optionally substituted by 1 or 2 substituents independently selected from halo, —NR$^{15}$R$^{16}$ and —OR$^{17}$ groups);

$R^{10}$ is hydrogen or a group selected from $C_{1-6}$alkyl or phenyl, wherein the group is optionally substituted by 1, 2 or 3 substituents independently selected from halo, phenyl, —OR$^{17}$ and —NR$^{15}$R$^{16}$; and each of $R^7$, $R^8$, $R^9$, $R^{11}$, $R^{12}$, $R^{13}$, $R^{14}$, $R^{15}$, $R^{16}$, $R^{17}$ is independently hydrogen, $C_{1-6}$alkyl or phenyl;

X is hydrogen, halo, cyano, nitro, hydroxy, $C_{1-6}$alkoxy (optionally substituted by 1 or 2 substituents selected from halo, —OR$^{11}$ and —NR$^{12}$R$^{13}$), —NR$^5$R$^6$, —COOR$^7$, —NR$^8$COR$^9$, thio, $C_{1-6}$alkylthio(optionally substituted by 1 or 2 substituents selected from halo, —OR$^{17}$, —NR$^{15}$R$^{16}$), —SO$_2$R$^{10}$ or a group selected from $C_{3-7}$carbocyclyl, $C_{1-8}$alkyl, $C_{2-6}$alkenyl or $C_{2-6}$alkynyl, wherein the group is optionally substituted by 1, 2 or 3 substituents independently selected from halo, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$ and —NR$^8$SO$_2$R$^9$; and $R^x$ is trifluoromethyl, —NR$^5$R$^6$, phenyl, napthyl, monocyclic or bicyclic heteroaryl wherein a heterocyclic ring may be partially or fully saturated and one or more ring carbon atoms may form a carbonyl group, and wherein each phenyl or heteroaryl group is optionally substituted by 1, 2 or 3 substituents independently selected from halo, cyano, nitro, —OR$^4$, —NR$^5$R$^6$, —CONR$^5$R$^6$, —COR$^7$, —COOR⁷, —NR⁸COR⁹, —SR¹⁰, —SO₂R¹⁰, —SO₂NR⁵R⁶, —NR⁸SO₂R⁹, $C_{1-6}$alkyl or trifluoromethyl;

or $R^x$ is a group selected from $C_{3-7}$carbocyclyl, $C_{1-8}$alkyl, $C_{2-6}$alkenyl and $C_{2-6}$alkynyl whereby the group is optionally substituted by 1, 2 or 3 substituents independently selected from halo, —OR⁴, —NR⁵R⁶, —CONR⁵R⁶, —COR⁷, —COOR⁷, —NR⁸COR⁹, —SR¹⁰, —SO₂R¹⁰, —SO₂NR⁵ ᴿ⁶, —NR⁸SO₂R⁹, phenyl or heteroaryl; and wherein each phenyl or heteroaryl group is optionally substituted by 1, 2 or 3 substituents independently selected from halo, cyano, nitro, —OR⁴, —NR⁵R⁶, —CONR⁵R⁶, —COR⁷, —COOR⁷, —NR⁸COR⁹, —SR¹⁰, —SO₂R¹⁰, —SO₂NR⁵R⁶, —NR⁸SO₂R⁹, $C_{1-6}$alkyl or trifluoromethyl.

2. The method according to claim 1 wherein $R^1$ is benzyl optionally substituted by 1, 2 or 3 substituents independently selected from fluoro, chloro, bromo, methoxy, methyl and trifluoromethyl.

3. The method according to claim 1 wherein $R^3$ is hydrogen.

4. The method according to claim 1 wherein X is hydrogen.

5. The method according to claim 1 wherein $R^x$ is methyl, 1-methylimidazolyl, 1,2-dimethylimidazolyl, N,N-dimethylamino, azetidinyl, pyrolidinyl, morpholinyl and piperidinyl.

6. The method according to claim 1 wherein the compound of formula (1) is selected from the group consisting of:

N-(2-[(3-Chloro-2-fluorobenzyl)thio]-6-{[(1R)-2-hydroxy-1-methylethyl]amino}-pyrimidin-4-yl)methanesulfonamide;

N-[2-[(3-Chloro-2-fluorobenzyl)thio]-6-[(2-hydroxy-1-methylethyl)amino]-4-pyrimidinyl]-4-morpholinesulfonamide;

N-[2-[[(3-Chloro-2-fluorophenyl)methyl]thio]-6-[(2-hydroxy-1-methylethyl)amino]-4-pyrimidinyl]-1,2-dimethyl-1H-imidazole-4-sulfonamide;

N-(2-[(2,3-Difluorobenzyl)thio]-6-{[(1R)-2-hydroxy-1-methylethyl]amino}pyrimidin-4-yl)piperidine-1-sulfonamide;

N-(2-[(2,3-Difluorobenzyl)thio]-6-{[(1R)-2-hydroxy-1-methylethyl]amino}pyrimidin-4-yl)pyrrolidine-1-sulfonamide;

N-(2-[(2,3-Difluorobenzyl)thio]-6-{[(1R)-2-hydroxy-1-methylethyl]amino}pyrimidin-4-yl)azetidine-1-sulfonamide;

N-{6-{[(1R)-2-Hydroxy-1-methylethyl]amino}-2-[(2,3,4-trifluorobenzyl)thio]-pyrimidin-4-yl}morpholine-4-sulfonamide;

N-(2-[(2,3-Difluorobenzyl)thio]-6-{[(1R)-2-hydroxy-1-methylethyl]amino}pyrimidin-4-yl)morpholine-4-sulfonamide;

N-(2-[(3-Chloro-2-fluorobenzyl)thio]-6-{[(1R)-2-hydroxy-1-methylethyl]amino}-pyrimidin-4-yl)azetidine-1-sulfonamide;

N-{6-{[(1R)-2-Hydroxy-1-methylethyl]amino}-2-[(2,3,4-trifluorobenzyl)thio]-pyrimidin-4-yl}azetidine-1-sulfonamide;

N-(2-[(3-Chloro-2-fluorobenzyl)thio]-6-{[(1R)-2-hydroxy-1-methylethyl]amino}-pyrimidin-4-yl)-N,N-dimethylsulfamide; and N-[2-[[(3-Chloro-2-fluorophenyl)methyl]thio]-6-[(R)-(2-hydroxy-1-methylethyl)amino]-4-pyrimidinyl]-1-methyl-1H-imidazole-4-sulfonamide;

or a pharmaceutically acceptable salt thereof.

7. The method according to claim 1 wherein $R^2$ is $C_{1-8}$alkyl optionally substituted by 1 or 2 hydroxy substituents.

8. The method according to claim 1 wherein the condition or disease is asthma.

9. The method according to claim 1 wherein the condition or disease is allergic rhinitis.

10. The method according to claim 1 wherein the condition or disease is COPD.

11. The method according to claim 1 wherein the condition or disease is rheumatoid arthritis.

* * * * *

UNITED STATES PATENT AND TRADEMARK OFFICE
CERTIFICATE OF CORRECTION

PATENT NO.        : 8,106,063 B2
APPLICATION NO.   : 12/508934
DATED             : January 31, 2012
INVENTOR(S)       : Mark Ebden Page 1 of 1

It is certified that error appears in the above-identified patent and that said Letters Patent is hereby corrected as shown below:

Col. 108, line 1, "-$NR^5R^6$" should read -- -$NR^5R^6$, --.

Col. 108, line 32, "-$SONR^{15}R^{16}$," should read -- -$SONR^{15}R^{16}$ --.

Col. 108, line 39, after "-$NR^{15}R^{16}$" insert -- -$CONR^{15}R^{16}$, -$NR^{15}COR^{16}$, --.

Col. 108, line 61, "napthyl," should read -- naphthyl, --.

Col. 108, line 67, "-$COR^7$" should read -- -$COR^7$, --.

Col. 109, line 9, "-$SO_2NR^{5R6}$" should read -- -$SO_2NR^5R^6$, -- .

Col. 109, line 24, "pyrolidinyl," should read -- pyrrolidinyl, --.

Col. 110, line 19, "N" should read -- N' --.

Signed and Sealed this
Ninth Day of October, 2012

David J. Kappos
*Director of the United States Patent and Trademark Office*